US011739324B2

(12) United States Patent
Collin et al.

(10) Patent No.: US 11,739,324 B2
(45) Date of Patent: Aug. 29, 2023

(54) ANTISENSE OLIGONUCLEOTIDES RESCUE ABERRANT SPLICING OF ABCA4

(71) Applicant: Stichting Katholieke Universiteit, Nijmegen (NL)

(72) Inventors: Robert Wilhelmus Johanna Collin, Venlo (NL); Alejandro Garanto Iglesias, Nijmegen (NL); Franciscus Peter Maria Cremers, Malden (NL)

(73) Assignee: Stichting Katholieke Universiteit, Nijmegen (NL)

( * ) Notice: Subject to any disclaimer, the term of this patent is extended or adjusted under 35 U.S.C. 154(b) by 1089 days.

(21) Appl. No.: 16/451,101

(22) Filed: Jun. 25, 2019

(65) Prior Publication Data
US 2020/0407718 A1 Dec. 31, 2020

(51) Int. Cl.
*C12N 15/113* (2010.01)
*A61K 9/00* (2006.01)

(52) U.S. Cl.
CPC .......... *C12N 15/113* (2013.01); *A61K 9/0048* (2013.01); *C12N 2310/11* (2013.01); *C12N 2310/315* (2013.01); *C12N 2310/321* (2013.01); *C12N 2320/32* (2013.01)

(58) Field of Classification Search
CPC .............. C12N 15/113; C12N 2310/11; C12N 2310/315; C12N 2310/321; C12N 2320/32; A61K 9/0048
See application file for complete search history.

(56) References Cited

U.S. PATENT DOCUMENTS

| 10,017,811 B2 * | 7/2018 | Leamon ............... C12Q 1/6874 |
| 2006/0154886 A1 * | 7/2006 | Weihe .................. C07K 14/705 536/23.5 |
| 2013/0245099 A1 * | 9/2013 | Collard ............. A61K 31/7115 435/375 |

FOREIGN PATENT DOCUMENTS

| WO | WO2013/081755 A1 | 6/2013 |
| WO | WO2013/173637 A1 | 11/2013 |
| WO | WO2015/004133 A1 | 1/2015 |
| WO | WO2016/201272 A1 | 12/2016 |
| WO | WO2017/087900 A1 | 5/2017 |
| WO | WO2018/109011 A1 | 6/2018 |

OTHER PUBLICATIONS

Riccardo Sangermano: "Unravelling the missing heritability in ABCA4-associated Stargardt disease", Doctoral Thesis, (Jun. 28, 2018), pp. 1-259.
Jana Zernant et al: Analysis of the ABCA4 Gene by Next-Generation Sequencing, Investigative Opthalmology & Visual Science, vol. 52, No. 11, (Oct. 31, 2011), p. 8479.
Jana Zernant et al: Extremely hypomorphic and severe deep intronic variants in the ABCA4 locus result in varying Stargardt disease phenotypes, Molecular Case Studies, vol. 4, No. 4, (May 30, 2018), p. a002733.
Albert Silvia et al: Identification and Rescue of Splice Defects Caused by Two Neighboring Deep-Intronic ABCA4 Mutations Underlying Stargardt Disease, American Society of Human Genetics, Chicago, IL, US, vol. 102, No. 4, (Mar. 8, 2018), pp. 517-527.

* cited by examiner

*Primary Examiner* — J. E. Angell
(74) *Attorney, Agent, or Firm* — N.V. Nederlandsch Octrooibureau

(57) ABSTRACT

The present invention relates to the field of medicine. In particular, it relates to novel antisense oligonucleotides that may be used in the treatment, prevention and/or delay of Stargardt disease

19 Claims, 4 Drawing Sheets

Specification includes a Sequence Listing.

SEQUENCE LISTING

<160> NUMBER OF SEQ ID NOS: 30

<210> SEQ ID NO 1
<211> LENGTH: 128312
<212> TYPE: DNA
<213> ORGANISM: Homo sapiens

<400> SEQUENCE: 1
aggacacagc gtccggagcc agaggcgctc ttaacggcgt ttatgtcctt tgctgtctga        60

```
ggggcctcag ctctgaccaa tctggtcttc gtgtggtcat tagcatgggc ttcgtgagac    120
agatacagct tttgctctgg aagaactgga ccctgcggaa aaggcaaaag gtaacagtta    180
ctgtctgtgg tttaaaaatg aggtgtggag caaataaaca ggttggaagt gtggggtggg    240
gtggtggggt agggtggtgg ggcagggtgg ggggttgtga gcagtcagtg ggcttgtcgc    300
cgattagcac tgaagcagtg tttagctgga cggccttttct gtgggcccct ctgacagtgc    360
ccttcccagg aagatgtgtt tctctgtcct cagccacatg aaaatctttt gcctaccgtg    420
cctgtcaatc cattgcctgc ccgcccctcc cccacccccc gttttacacc tgcctgtcca    480
gtctaccgct ctctagggca tccacgctga gcagtgggaa gaactttaag ccctgaagag    540
caggccaaag gcaagcaaga accccctcga acagcttccc agcttagtga ggcccttattt    600 cattgattct ctgaggcaca ttgttttttc acatgttagc atttctgaaa ttgggatgca    660
gctcacgatc aagtcacagt ttaactggac acattatttt tctttcttag tggtgcagaa    720
aagtaacagt gtgtcttaca attgactgcg tcctagattc tgtgagatgc aatacgttat    780
taaccatcac gcacatttcc tgaactcttt caatgagcag acaccagcct gggttagact    840
ggagccctaa aagcacgaca cagattccac cctggactgg cttctgttct gcctgggaaa    900
acccaaagta cgtttggaga ccaagagcaa cataaagtag cataggtgga atagtccatg    960
agaagtgcga gcaaaaggtg ccggagatca gagaacacca agactgtact tgtaaatgac    1020
aactggcttt gtgcaatttt ttctgggaaa ggataaggag tgactataga actgtaaaga    1080
aagaatgcac tttgctacag ccttgcagag ttgtgcaaat gccgatgact aaaggagctg    1140
aaagaggaag gaggggataa gggatggggg ctggtaggg gtgagattag gaccctggga    1200
gctgcaagcc actggagaga tcaggaggaa agggagggag acctgcttta ggcgagaaga    1260
gaacagtatt tgttccaaat ctcggttcag aataagttca tgtaggtgat ggggccaact    1320
ggaacaggtg aaggcctatg aatgagtgtc tcagttaggg tctccttaga gtttaatatg    1380
aaaaggtgtt agctaagtac agagctggta cctgagagag taaaaggaaa ctctaaggta    1440
tcatggaggt agcaattgca ggacacagct cccaccccta gggctgagag aaccaaggga    1500
agagacagga attattaaga cttggagcat agatgagagg tctgtggagc tgacattagg    1560
acttgggagg aaggcgtgca tggaggctgc tgctggatct ctgaacctga cctcgggtct    1620
ggacccctga ggagaaagcc ctggcaggtt ggtgcatgtg gggccgaggg acaatagctt    1680
aacaaccagc ataaaagaga gcagcatggg acacgcttca accatgcgca tggatggctc    1740
caaaacctgt gtgtggctgg cccaggacgc agggaggctg caggggggaag agacaagtta    1800 aacctgactt gtctgggaag caccattgtc ctcaggtcac tttcctctgt caagcctggt    1860
gctgaagtta tctgttgtct ccaggggcca agtattaaga gtaatcagaa actcagtcct    1920
ttcttctagg agcttcccctt cttgcatgaa aatcctgata aaactggaaa aaaaaacctc    1980
atgattaaat ttttcatgt attcattctt tccttctatc aaaaaataat ctccaggcac    2040
cgtgctaggt tcattggtat acaatggcaa caagacctcc cagcccctgc ctatgtgagg    2100
catctgtgga ctgcggagga aaatccaata tgccattgtt ctctcttttcc cataagaaat    2160 tacaattctc agttcatttt attctcactg tgctctttgt gacccctcaaa gggggtcaca    2220 tgataacagg actgtagctg ctggcctaaa atgagcccat tcctgtggcg ctcatgtcgc    2280
tgtgacagag aataaccctg ttttcagaat gctctggtgc cctccctctc aatctggcct    2340
ttcgctggca tgggtgggcg actcctgctc agggactctg ccttctccac agtgtgctcc    2400
cagggagatg gagccactcg ggctgagggc cttggccagg gcacctccca gggctgggcc    2460
```

```
tggtctgggc tggcgttcac tggatgccat cctgatggcc tggaaattga gatttctgtc    2520
tggcacgcct cccgatggct ccccacctgc taccacattc caggagcttc caggatgtct    2580
gggtaagaca gaggcacccc caacagattc agtagctctg agagggatct gtggctcctt    2640
cctaagcttg cggttcttct ggaaacttct gcctctagaa gatggtccct ctaagaaaag    2700
tacaaccacc cagcccataa ttcagctccc aggttttccc tcaaacctcc atgtctcctg    2760
taagcagagc aagagtaaaa tcagatacca aatttcctca ttcctcagct cccaatccct    2820
aagggcataa gatgaaaatc ttcagatctc tgctttcctc cctcttttt tcttcctctg    2880 ttaacatttg tcaagtgtta ctaagtgtct ggcactgtac taagtgcatc acctccctga    2940
actctccgaa cagttccacg agagaggcct ctctgtgatc cccccggtac tgatgaggtc    3000
actgaggctc cagagaagga ttagtaactg gtggggttgg acctgggatt cacacccatg    3060
ctgcgtgacc caggacaggc aggcatggcc gttacaccac actgaccccc gtggatcgag    3120
atctatccaa tagtctggtc actgatatca ctaagataga gtggccatat aatttatcat    3180
ccaatcaggg cagttttgca agtgaaaggg agcactatta ataattgcac tgggacaata    3240
aatgtaaacc aacactggac ctggaaaact gggacgtgtg tttgccctat accaaggtaa    3300
gctagacaca gccactgcct tcatggagtt cagaaccagg caggggcggc tcccacgtat    3360
aattactgtg cagcacaacg tggagaccgt ggagtagaag gaaacacgga tgggaggtga    3420
ggaggaggtc tgtgagctca gaggaggcac cggggctgga gagggtgaga gaagacttcc    3480
caaggagttc atcctgataa cgtgcattcc caatgacgag cgctctctcc actgcacaag    3540
acaagtatac atctgcccgt gttggctgtg gacctggcgc tgtgtcaggg agggtttatg    3600
aagatcacta ggtgggtctc ttggtgtcat cccttcatcc cagcttctgg gttaggatgg    3660
atatctgtgg gggggcctga ggactcatga aagtggggcg ctaatcatgt tttggacacc    3720 acacctgga gcacctggga cagctgtggc ctttgtcctg ggttcagcat caagccgagg    3780
atgtggcaag taaagagagg ctgggcacca actccagtgt acccaggctc cgggtcatgt    3840
ttgtccaggc taagaattct gtcctggttc tcagtgcaga aggaagaatc atggggctca    3900
ttttaggcct tggctgcctt ctgttaaatt gaaaacagag caggaaggaa gaaaatttaa    3960
caggctcagt tctaaaacaa caagcacaac tgtgcccttg ccagaaaccc ctcctcccca    4020
tgttgattga atggtaaaga gaggagggga ggtgagaggg agagagagag agaggaagag    4080
agagagaaag gaaagaaagg aaagaagaag aaagaaagaa aaggaaagaa agaaagaaag    4140
aaagaaagaa agaaagaaag aaagaaagaa agaaagaaag agaaagaaag aaaggaggga    4200
gggagggaag gggaaagaa aagaaagaa aagaaaaaa agaaggaaat accagtttgg    4260
gaaaaaagaa ttttccacca gcccttctga gccttgctg ggcttaatta aagttacaga    4320
catgtgtaaa gggcagggta gggggagtct gagctgctga gaaaacatgt ttttaattat    4380
actgtggaat ttctccctgg ggtatgcctg tacgcagtta agcgtcaagg acagggatgc    4440
cgctctgggg aggggaagct gagcatgatt ttggaagccg gcagaagagg ctattgtgaa    4500
aaccagacct gtcaggctag gaaaagaatg gctggtggtc tttgaccagg gagtgacgcg    4560
tgaaatgcag caaccgcccc cgccccccgc caaaaacaaa cacactctca cagagttaga    4620
acaacagtga cctctcaaca aatatttttc aaagattacc aaccaaccat tacctagagc    4680
agcggttctc aaccttggct gcacggtgga actacctgag cgtgttaaa aagaagaacc    4740 ctgatgtccc atgccccaag attctgatgt agttgatctg gggtatgatc tgagacccg    4800
```

```
gcatgttttc agcctgcagc cacatgagaa gtgctgacct aatcaacagg ggtgatgatt    4860 tgagggcgg ggactatagg caaaaaaaaa cagcctaatt caaggatgag aagagggcac     4920
aggtgaggtg ggaacagtcc tagggccaga caaagaagga agggagaaag gaggtgctga    4980
tccctcccct actcctgaga ggaggccttt aagtcaccgt gccttgtgga gaccagattc    5040
ttcaaaaata caagaatgag tgagtgaggg agtgggtgga tgccaggaga gtgcgtgaca    5100
agccttgcaa gggaggatga caatgcacta gcttggtttg gaaattttac ccctggaaca    5160
ggcaggccaa gctggctggt cccctccctg atacacagcc ctccctcttt atatatggag    5220
caggggacgg tgtgtggctg gtttcttagc aagcaccatg gttccaagtt ggcaactggg    5280
gagttctgaa tccaaaaagg agggagatga acgtaagtgg agggcaggcc tacaaggttg    5340
cagataagct taattctgtc tccttactct tctgcctttg caacaaccct gtgatcttgc    5400
gacaaccctg taaggcaata acaaatggct catgtttatt gagtgttacc tcatgccata    5460
ttgtgctttc gtgtttaaca caattgtctc atttcaccct cacgactgct ctggaggta    5520 ggtcctggta tcacatccat ttcacagatg agaccatttg gcacggaaga gttgagtggg    5580
ctgcccaagg tcacatagct aagatggaac aggctggata ggaaccccag taacttgacc    5640
tcagagtaac cttctcttaa ccctgagtgt acactgtagg aaaaatgagc agtcccattt    5700
cagagaggac aaaactgaga ctcagaggtt aagcaagccc caagtggtt gttaacccag     5760 atcttcccac taactcccaa atcagcatca gtgtttaacg taccagacct ctcccagata    5820
gatgttgccg catggaagac agccgatcta cgtgatagaa agccaatatt gcaagcagtc    5880
gtctaaagga gtcaaatgtg ttggatttga actggatgtc tcatttcttt ggtgaagaca    5940
ctggaaacaa cttccaggtt tcatcaattg ctcctatcac tcaacgttgc tatcttactg    6000
aacttgttcc ccagccttac ccactgatgg aatgatccag aatggaagac aagcaccaa     6060 tgtacatgac cctggggag gctgtttctt aaatctacag actgttggtg acctgagccc     6120
catgtcacca aaggctttcc tggagaagcc tcctagacca gtcttgacaa aggctcactc    6180
attccgtgga tatttattgg gcacctatta tgagttctgc cccatgtggg gtgctggaat    6240
cacagtagtg acaacgacag atgaggttcc tgtcctcagg aagcttactg cccttgaggg    6300
cttcacttac ttggaggagt gatgaacctg aagtgcggtg tgtgttaaga agcggaagtc    6360
cagggccagg cgcggtggct cacgcctgta atcccagcac tttgggaggc tgaggcaggc    6420
ggatcaccag gtcaggagat cgagaccatc ctggctaaca tggtgaaacc ccgtctctac    6480
taaaaataca aaaaattag ccgggcatgg tggtgggcac ctgcagtccc agctactcag     6540
gaggctgagg caggagagtg gcgtgaacct gggaggcaga gcttgcagtg agccaagatc    6600
gtgccactgc actccagcct gggcaacaga gtgagactcc gtctcaaaaa gaaaaaaaaa    6660
agtgcctcac ggagagtcta ttcttttctt cccatattgt gtgtgtgtgt gcgcgcttcc    6720
tccaacacat cctccctata tatttttga gtaaaacatc ttgtaaaaag ttacagctac     6780
ataatcacca cctgtccta aatagttttt gcttttctt tcttcaatgc acgatcattt      6840
tcccccatca atttattttt tagtttctta taatcttgtt gccagtaggc tgtttttta     6900 aaagcagaac atggtttgtt cttactagca ggaaaggagc attattgag cctctgctat     6960 ggtgtctttt atttgctga gagcctattt acatttcttt gagaggaaaa caacaagggg    7020
ttacatgaaa gaccatgtga atagccccta gctgatctat taaacttgct attccccggc   7080
cagctgcttc agatctccctt cagatcttat gtgtttcctt cctaaggtcc ctggagtaag  7140
ggttgcatag acctattcta ctctccaact cacatgtccc tctccctctt cctctccata   7200
```

```
attccacatc tccaaccccc acccctatgt gcaatgccac agggtgtgga ctgccacagc    7260
cactggatct gcttttggaa tcaagagtcc ttaagctcca aatggaaccg aaatttaaat    7320
accaactttc aaccatatgt taacatcagc agcctcttcc aatgtaaaaa cccatggcag    7380
tgtgccctgc tttgtttctt taagcaatag aaacttgaag gaagcatgtt ggtaggccag    7440 attttttgttg gctttgcaat ggatcacagt catttattca ctcattcatt cactgattca    7500
ttaaatgacc acatttgcaa gggcaaggta atggggaggg ccagaaagga cactggcccc    7560
agaaacagga ggctggattt tggttctgat gctgccactg ctgatgtgac actgcacagg    7620
tcacctgcct cctctgagcc tctttcctta actgcagagt gagtggctac agagaaatct    7680
ttactacctg ttagatcagc attacctggg agcttgttag aaatgcaagc tctggtgggg    7740
ccatactgaa cccaaatctg cattcatgtg catagtgaca gctaaaatgc actgaagcag    7800
atgatcttga tgatccttta tgaaagtctc atgctaatgc agttttctaa aatagaggca    7860
gagtggaacc cagatggaca caaaatctgg ttgatataat aaaacaaggt agagggtgta    7920
tggtggggag ggggtaaagg aaggaaactg tttaggtaaa gataccacaa ccaaagtcct    7980
actgcacaca tgggatctga ggagggctgt gtctgctctg gttacgtttt ctataatctc    8040
ttagcaccac tgaactttct ctcttttttgt tttgtttttc cagattcgct ttgtggtgga    8100
actcgtgtgg cctttatctt tatttctggt cttgatctgg ttaaggaatg ccaacccact    8160
ctacagccat catgaatgta agcatagcag ggtagcttgg gcaagccctg aagagacttt    8220
ggtctgggcc ttttgtctag aaagatcttg gggtgggagt gtggggatca gatctgctta    8280
tcatcatttc atgtctatga tgcatgtaac agatttatca atgttacaca aattataatt    8340
tttaaaaagt ctttagagac agggtctcac tctgttgccg aggctggagt acagtgttag    8400
gaccatggca cactgcagct tctatctctt gggctcaagt gatcctcctg cctgggcttc    8460
caaagtgctg gaattatagg catgagccac tgctcccagc taattttttt gtttttttgtg    8520 gagacagagt cactacattg cccgggctgg tcttgaactc ctggcctcaa gtgatcctcc    8580
cacctcagcg ttctaaagca ctgggattac aagcatgagc caccttgtcc agcccaaatt    8640 ttcatgttttt aatcctacac attctaagca aatacttgtg tgtagttact aagggactgt    8700 gcacttatttt ttgtttgctt tgttgttgct agttttttatt ttttttatacc taaactctct    8760 cgttttaaag agaacagatt tgtagatgag ttctcgaaaa tatttcagga atcaatatag    8820
agaatatgtt atacatggtg ccagagaaaa atgaggacaa gagatgctat acaatcgtac    8880
tgaagaaaaa ttttatttct tggacccctg aggtgtctgc agacctgaaa ggaacctagt    8940
gagagcctct tttacactct gccctgtgg gaaagccttc acctggtttc cggccctcta    9000
tgtggtgaat gtggaagcct caagcgttat gcaaatctgc ccagtcctct attcttgatc    9060
ttcaccttct cgttcatgag tttcaggccc cagttctgaa tcagcctcct gtccatcaga    9120
ctcttcttta cctctccccg aggagcccat aacctgcagc cctactgcat gcttgggta    9180 ggtgctcagt tcaccgtggt tgaaggaata gacgagcgtc tgctcaagca gcagcagcaa    9240
ctgcgtggag tcttcttgaa ctaacactcc tatgcccctc tcggcacaaa atgacgtgtc    9300
cccccttgct tccccttcac atttccaccc atgcctatta caacatccgt ctgtctcccc    9360
actacaccgg gagcttgaga gaagaggcca tgtctctagc acccagcaca gggactggca    9420
cacatgagat gctcctgctt cttaaatgct gagaatgaag gaggacatca gaggggcccg    9480
ggccccttcc caaaaaggcc aactcctagg tctgcatcct gcttggtctc catgactaat    9540
```

```
cccgtcttgt cctcatttttc tgttttaaag gccatttccc caacaaggcg atgccctcag    9600
caggaatgct gccgtggctc cagggatct  tctgcaatgt gaacaatccc tgttttcaaa    9660
gccccacccc aggagaatct cctggaattg tgtcaaacta taacaactcc atgtaagtgt    9720
tgagatccct accatgcagg ggaggaagtt gcacacccct tcacgtgctg aaatgcacac    9780
gtgcgtgcac ggagcatgga gcactgagtg ttcttgtggc tttgctgagc ccctaacctc    9840
ttaggagcag agcaggtttc ctctctggaa cattctgtta actgtcaggg cacttgggga    9900
gaaatctcca agctaaggcc acgtgcacaa aatttcttgg tccttatatc cccagaatgt    9960
gacctggagt ctgatggcag cccgctgcag agatgtgtcc actgccttct ggtcattgac   10020
ctgcttgggt ggagtgaatc attgtaggag aaaaactcag ttccctcacc ctgatcaacc   10080
tggacagatc tctcttcctt taaaagcttt cttggacatc taagggctag aaaaatgtc    10140
agggagcatt gggaaggtaa atgaagtcag gtttacaaag tcaagtttac ttcttgggag   10200
aaaaatacaa tttccaaatc ctctgttata attgccatcg gcccctgga gtggtgagat    10260
ctcggaatat ggctcgggtg cagtggctct tcactgtggg cctgcaggct attctgaaaa   10320
gctgatgaaa accaatgacc cctcttccaa gaaaaatggc cacataccaa acattacact   10380
gtacatctga tttcagggaa ttgtagatgc caggttagta gcctcaggtc tagggtcaaa   10440
attcaagtcg aatcccacag gaagagggtc tgccttcgga attccctttc agagcattgg   10500
gagaacatca tgggagcata ttctagagac agaggcttag ggtgtggaca gggccatccc   10560
tcacccactg tgctgacctt aagcagcacc ttgtgcagcc catacctgaa ggccaccagc   10620
aaaggcctgt tggggagcag gctttacccg acctgtataa acaccaggct aggtgaaaac   10680
tgagatacct ggttacttta gttttttcct tgggggagct cagtatgatt cttccaggag   10740
aagcctgctt ttagactaaa aagaaaaaaa gtttgatagg tcaacctaat gattggaggt   10800
ggccttcccc actgtgaaca aactatggct gcatgtgccc tacaatggca gagttagta    10860
gttgtgatag agactgtatg atctgtaagc ctgtaatttt tatgtttgct gaccctgga    10920
ttaccagatg atagaagagg aaacatctgt cttcctagca aagtcaagga agtggcattt   10980
agcaggactc atattgctgc aagcactgcc ttgcagtttt agtttacaac tgcactttca   11040
gcttaagaaa cacctgccca tccagagaga tcgtgtgggg tcacatggtg ggatcaggga   11100
ggcctgaaga cagctcagtg gaggctgcat ggagctttgg tgggaacggc cctggcagtg   11160
tctatagatg ttattgcgga aaactgaggg gtgggagttg gagaagggg  ctccagactc   11220
tagctgtact tggcatttga acccggaaag ttgggtttca tgttttgcac tcacattatg   11280
agtgaaatat tggcttattc aaggttcttt tgcttgcaag gcacggaaac ccattcaagc   11340
aatcttaaac cccagaagga aatctatgat ttggatacta gacattctca cagagccaag   11400
ggcagcaagg cggggctcag gagaggcagg ccaagacctg gagagctgtc aggagctgct   11460
tcctcaactc tcttccatct gggcctgcca gccctggcct ctgtatctac tccattcacc   11520
tctctccatg gaccagtctc ccctgctcct caatgcctgg gctgccattg ttcatgcaat   11580
tcacaatacc tcggcctggg caatcagaag ctcatctctg aacaccatcc aaattcctgg   11640
gaacaaatcg ggttgaccca gctttattct ccctgtccca tcagccttgg cagaggcgtg   11700
catgtgcatg cgtgccaatg tgtgtgtgca gggaggtcct tgtggatgaa gcatggctgt   11760
cagagcctac ctgcgtgaat gggtggaagg gcaggtctca gagaattggg taaaaactgg   11820
ataaaccctc cagtgatatc caccaatgtc acctgttta  aggcttctct gggcaagaga   11880
cacacagagc atgggaccga gaggcgagca gaccctgcca aaactgggag actgaataga   11940
```

```
tcgctcacca tccttgtcag ttagcctata tgtacaagga agtaaaatta tctctttctc   12000
ctgccttggc agtattgtaa ggatactcaa tgtagtagct aggccagaca catagtatct   12060
ttaaatatag catgagatgg ccaagcacgg tggctcatgc ctgtaatccc agcactttgg   12120
gaggctgagg cgggtggatc acgaggtcag gagatcgaga ccatcctggc taacacgatg   12180
aagccccgtc tctactaaaa atataaaaaa ttagctgggt gtggtggcgg gcgcctgtag   12240
tcccagctac tcgggaggct gaggcaggag aatagcgtga acccgggggg cagagcttgc   12300
agtgagccga gatcacgcca ctgcactcca gcctgggtga cagagcgaga taaaaaaaaa   12360
aaatagcatg agatattatt actgttataa aaataacagc tatttcctta ttaatgaggc   12420
tttgtcctta cagcttggca agggtatatc gagattttca agaactcctc atgaatgcac   12480
cagagagcca gcaccttggc cgtatttgga cagagctaca catcttgtcc caattcatgg   12540
acaccctccg gactcacccg gagagaattg caggtaagca tgactgcagt gctctcaagc   12600
atcatttccc tcacctatgg agagactgaa gatataggaa agaacaggga gagttggtga   12660
aaaatatact agcggaggca ggaagggatg gggtctggag gcggcttgaa catcaccttg   12720
gtgaagatgc ctcttcctcc acagaagcct ggaaggtagg aagttgggaa ggaaggcagg   12780
aaaggtctca tccacgttaa gtctagagac agaaagaatg ctaagagaga tggcactatg   12840
ggaagtatga ggctaggtca agggctagaa gcaggggaga cgagtttaca gagtttcgta   12900
aagatataga gcaactctca cagagttcta gagcgagagc taaccaggaa catgaagcag   12960
caaggccaac tatcattaag gagccaggga ggtcagagat catgtattat catgacataa   13020
atatgcataa ttgtactatt tctcccagta atatttagca cccaggcccc gaggcagagc   13080
aagtggagag tgggtgatgc agggctgggg gtgtgtatgg aggcaccaca gaaggtcaac   13140
aggcagcggg ctgaaggcag ggactggact acatgcatca agtccaggct gcacgaggaa   13200
ggatgagaag gcagatgagc acggaaatgg actgggggaa atgaagaggc aagggaatag   13260
aagtctcagt gggtgccatg accctgttta agtgattgag aaaatgaaca agatgaaaag   13320
gttaatggct gtggtcagaa agtgaaatat gtgaattcag gatttcgaag gtagggtggg   13380
tgatgactgg cccccagatg cggccatggt gaagtggggc aaaggtgcag gtgcatggtg   13440
aggggaagga ggaaatggga ggtgatgatg ttggccccac acggacacca cggttgtgca   13500
ggaagatggc aggagctggg caccagggtg ggagccacct ggagtcagga agagtgaaga   13560
gaaaggatga agaggctccc tctcctgtgt ctctcctccc caggagaaga acaagaaaca   13620
atccgaaagt aataacacca atgtgccttt acaaagtgtg agtgggtgtt gtgtgctgtc   13680
acgtgtgtag taggctcctc tgtggatggc tagagggact ggacatggcc actggatccc   13740
acttgcaaga gcagaggaaa agagtggtcg tgaggaagta aagcccccca aaatccaggg   13800
gttgctgcag cttttgggtgt ggagcgtgcc ctctgaggaa aggctgctct gggggagatt   13860
gcccaggaaa cggggctcag aggccacgaa agcagctgtt aggggcttct gggagatgtg   13920
tgctcctagg attagggagt tgactctaag gatgacctta gaggttaaca gggatgagaa   13980
aggggtcacc aagggtcta ccaggggaat gggagaggct gtattgatag aacagcttct   14040
gctgcaggtt ccaaacaaga aatgtgggag aatggttgaa atcagcccg ggggcacctt   14100 cccgtgcatg cgtgcagctc cttcaacatt cagtcgacct tcagtgcctc ctgtgagcca   14160
ggcactgggc tagtctctgg gggtggagag atgagtcagg caaatgccag ccctcagagg   14220
gctcacaggg cagaaggtga gagatgagtg agcagaaaat gaccacagcg cgtgtggggc   14280
```

```
ccagtggagg gaaggagggg attcaggagc acaggagagt caacagggga aacttctccg    14340
aggagaatct gatcctcctc ccatctggcc accttctgaa gccctctctc cccatccaag    14400
tgagaaagga caggcgtatg accagattgg tgtatgaaga tgctgaatta cgttctcatt    14460
gtttcaaact agtaaaccat agattttatg tagtaacttc tacaaactgc attacaaaca    14520
ctccattctt tgttgccctg ggtagaagtt tattttagtg agcccaagtt tgaggaacct    14580
tatatggtat gagtacaatt accattttaa tagtaagaaa tcccccttcc cctgtgtacc    14640
aaccagaagg tgttttttc ctaatttaaa caaacagatg cagacgtggg ctgtccagct    14700
cctggcggga tgacatacct catgcatcca gtgggtttga tgatgaggca gacatttcac    14760
ttaagtgcct gatcatcaga ttgagtcctg ctggaggaa gtgtgaagga agtaatttca    14820
aaccacagtt tctctgtggc ttttacaatg tggatatgag aaccaaaatc actacttctt    14880
aaccccagag caggactgat tttgaattgg tatgcaggcg gttccttctg caggcttcgg    14940
gctgtgagaa gtccctaaca gagcaaatct ggggacaagg gctcaggaaa ggttggccac    15000
ggcccctag gaatgggggc tctgcaagat ccctggcctt agaggctgtg agagggaaca    15060
ggggtccatc cccaagtaag ggacacggtt tttgaggaaa tcccaggcca gggcctgaag    15120
ggcactgtca ggaacacagg ctgtttcagt ctgttgagat tcaccgggc gctgctcact    15180
gtgagcacgg actcctcagg ccaatgtggc agaagagccc acctttgaaa gcgagcgggt    15240
gggggtggcg gggctggtgc tggtgcgtgc ttctgcacag ccacctggga aggtatgccg    15300
ctggttgacc caggcagagg ttttctttca tggcaaacct gcagtactgc attctcagca    15360
gggaggatta atggtaaaag accaggcatg gagccccctt ccctctccct cgaagcaagc    15420
tctgtggtct ctcaatcatc tttaaaacac cttcttcccg ggagcctcct acattctcct    15480
ggcttccctc ccaccccac cctcagctcc tggggcctca gcagcccac ccccaagcct    15540
ctaatcttcc cagggaaggg aacaagaaga accacatttt aaacgaaatt tattttcctt    15600
tcctcaggct cccagttcac atttctccct caggagtcta gggaagcttc tgtctggtat    15660
cggcctcctc ttcacctggg cccccgccct cctcaggtgt accagaagcc agcacactcc    15720
cccttccccc ccagagccac agcagccctg tctcctgggt ggtcttgtgt gccaagcctg    15780
ggcaacatca ctcccagctt ttcttgtttt gccccttctc cccagcaaga tatttgtatg    15840
taaggtcagg tgagtgagtt aaagaataac gaagagataa acagtcaaat ggagtcctga    15900
ctgtcaggtc aagacaacag ttatttactg aatgcctcat gtcattcaac agacatttat    15960
tgagactctg attggatgtc agtctttaat gctgggtgtc agagagaggt gacttcaagg    16020
gcttgcatct gtgcacccag cattgctagg tacaatgagg agtataataa aagcaggagc    16080
catagccccc aactctcaag agatctccca tgtgtgtatg tctgcatatg cgtgcgtgtg    16140
catgtgtgcg catgtgtgca tgtgtgtgtg catgtgtgtg catgcgtgtg tgtgtgcgtg    16200
tgttggggat ggtgttggtg gagtgagagt gtacaaggct gtgtatgaag gggtaattgg    16260
gaaaagaaca atggagctgg cacccaggga caggaggaaa agcaggaggg ctgggtttgg    16320
aagacagccg gatttatgtt tttgaagagg gaagactaga atataaggga gcagcccttc    16380
tcagagccct cctcctccct tcgggccctg tgtccagctt tccccaaagt ccttggatct    16440
ttcctatgca aaggggagtg acagtgggca ccactctcag ggaacccatt actgtgagag    16500
aagccactgt gccactgtgt ggtcgaactt caagaccggc ttcccctgcc ccagctgcat    16560
ggacaggcct gtggggttgg cgcaagaccc ttccagagga aactagctgc aacataaatc    16620
cggatatggt gctgttcagg gaaaggcaca acctggggat gagaagggtg gctgtccagc    16680
```

```
acacagggc aggcctcttg gccactgggg gaggggagaa tttggagagg aagaggatgg    16740
gatgccgtgg aattgggacc aggaaagaat ggggacatgt gatggttaaa gctagttaga    16800
gaagaactgg gagataaaca gtcacccatg cccctgaagc actcggggtg aagagattgg    16860
cattttcacg caccccagtg ctttcccttt gtgttgaagt ccttcgtag acatccaggc      16920 ccataaggct cttctctggc cagagcctca tgaactatag cactagcagg gttgaggcca    16980
agcattggcc ctggaagcca gccgaggagg agggtgcttg tgtgaatctc ccaggaggggg    17040 taagaattat attaattcga tcataataag catttattga gtgctgtttt gaggcctggg     17100
agctaagcac ttcacattcc ttaccccgca tcaacaatcc tatgaggtag atgtggaaaa    17160
tgcagacacg gggacaggct caatcacttg ccccaaggtc accttaactg ttaggtgttc    17220
tttatgcctc cttataaaga aaccctgctt cccacaggtg ttgagaggag ctggagggag    17280
cttgactagg gctcatcagg caagcccgg catgtgcctg gctctcctct ttctacctgg      17340
agcttttcct gcccttaatg gccccaactc atttctctta gtccatgtca gtgccctgag    17400
catctcagcc caagctgaga tgatagaaac acccagaggg gtcctctacc ctgtgacagc    17460
tgcggtgtgg gaagagcacg tgtctcctcc aatcctagac cagagtttct cagcctcagc    17520
atcactgaca cttggggcta gataatcctt tgtgtggggg agggaggagt gtcttgggcc    17580
ttgcaggatg tttagcagca tctctggcct ctacccacca gcacctcccc agttgtgaca    17640
cccagaaatg tctttagatc ttgccaaata tttccaggag gatgaaattc ccctgtttca    17700 gttcccagc cccacctcaa tgagaagcac tgtcctagac caaccccaca agcatctga      17760 cacccccatc cagccctggc taacttttc caccttctta ctaaattggg cccagctgct     17820
tcagcagtca atgtgttggg ggcagcccac tggcaagagc ctcacctcta ggggctccca    17880 gagacccaa gaacagaacc ttcctctgag agttgagtta caagtgtttc caatcgactc     17940
tggctgtttt ccttttttg acccattcc ccttcaacac cctgttcttt ctcttattca      18000
tatgtaggaa gaggaatacg aataagggat atcttgaaag atgaagaaac actgacacta    18060
tttctcatta aaaacatcgg cctgtctgac tcagtggtct accttctgat caactctcaa    18120
gtccgtccag agcaggtagg gggatgtcac tggccagtgg tccctggagg ggagggaagc    18180
acccagcctg agaaaggcaa gaaatatatt ggcttttttc ttctttcttc cttgtgttca    18240
cattcagaat ccatcactta atgccttgta tttagaaaaa aaccggggga tcacttgaga    18300
tcgtgatcat tttcaacata ggattcgaag ctgtacacat cctggtgacc ttaaaacatc    18360
tcaggttttt ataactggaa ggaaccttag agatcatggg gcacaacctt ctctttatag    18420
atgaggaaac agaaatctat tcatttatta ctcaaatatt tagggacagt tgtaggtact    18480
agaacacagt gtgaaccaga caggcaaaac cccaggccag ggagcttcca ttccagtggg    18540
gccacaggcg atgctcaggt aagcagagac tccgctgtgt gacttctggc tgtgatgggt    18600
gctgcaagga aaatccggta gagtcgaggg ttagagaggg acggaggggc aggtttaagg    18660
gggatgctca ggaaggcctt cctgaggagg tggtatttga gcagagttgt ctgtcagcca    18720
cacagtaagt gagaggggag ttccgggctt ggaagctgcc agcacagtgc tggcaagtgc    18780
tggggtggcg tcccgaggct acagaacctg agatgctgca gaagagccca cttctgcttt    18840
cctggaccac ttccttctca gcaccaggca aactccttct tctatcccct ggcacatttc    18900
tgacctgtgt atacgccccc aatttatcta accccttaa ataatctcct ctatttatgc     18960
agagcattct taccactaac tcacgacttg cacatccctt agctccctta ctcctcacaa    19020
```

```
caatcctgag atgggtcaga gaaggaggct tgcgcgtctg gtgatggggt gatttgtgca    19080
cagttacagg gctagaaatt gtcagagcca gatggaatcc aggtcctctc aatcctaatc    19140
cagtgtttct tacttcagtc ctgtggctct caaagcccag agaccagcag catcagcgat    19200
gcctgggagc ttgttaggaa tgcaaattat cagggcccac tccaggtgaa ctgggtccaa    19260
agccctggga taaggcctag caatctgtgc ttcacaagcc ctccaggtga ttccgcaggc    19320
tcaggtgtga gagctgcagc tgtcctctgg gccttctggg ctccccgccc agcttcttca    19380
gtgtgatgaa cacagcgaga atgctagatc tgcagcagct gatatcccag acaccctccc    19440
gactccctcc tggctgggtc tgatcctcct ccagactcca ggagagaacg agacataaac    19500
agaacttcag agcctgtgtt aaccctgaga tcaaggtctg cacagggtgc tgtctgagtc    19560
cagaggagtg agggacccca ccccacctgg tcagcaccag ctcctggaag caggttctca    19620
cactggttcc ctgcacaatg aaggagctca tacctgcttt tctggcttct cagaccctga    19680
ggttttcacc gaaactagac aaggggaacc taggtcagc ctggaggcag ggtgagcttg    19740
gcgcctgcag tgcccaggcc ctgggtggtg cggctccggc caggccctgt ttagcttcct    19800
ctcccacccc cacagagggg gtgctgtcgg caccgattgc tcattttccc ctttgctttc    19860
tcttcagctc gtaaaactca agtcctgaca atgccttgat gacttccagt tggtaataaa    19920
agggagatga agataaggac aggaatttcg gggaaatttc tttccagttc cttactaatg    19980
tgacatttag atctctagta ctgtgcttct ggcatcagtg ccaaggcctt tcatgttgga    20040
gaatggaggc cggggtcacc aggttgtgcc tttatttcat gttgctggct ctgatgagct    20100
gatgctctgc tgattagcaa acgctgagcc atctgcgctt cgcagaggca cgttccagcc    20160
aacccggccc tccctgccca cttccagga tgctttgcct tgtgggctca cctgtcttct    20220
agctcctgat ctgtatctcc acctccatcc agttccgggg ctccttatca gcactgttcc    20280
cagaactgtc catcacgatg gcaacgttct ctctgggcgc tgtccaacat gggagctcgc    20340
ctctgtgttg tcactcatgc tcattgaaca tggatttgtg tcctttacca tcaggactgg    20400 ataccctcc tggtcctttc tgcctggggt cttagcacag ctcagaagga acctcaccat    20460
tccctctctc catctaggga attagaagat gacaggggca cagttctctg gctcacccc    20520 agcccagtaa actcctggac atgcttcaag gcccagctca gatgttgcct cctcagtgaa    20580
ataatttata aacccaccct tctttgtcct gccttctccc tcttccctac tcactggaga    20640
gttaacaggt gatggttaag ctctgggttc aaatctcaca aggccacaca cttagctatg    20700
tgacttcagg caagttaatt aaccactctg tgcctctcgt ttcctcattt gtaaaatgga    20760
aatagtaaaa gtgcctacca gcatggcagt tgaagttaaa agaaataata tatgtgaaca    20820 cttgaaggg cgcctgacac atagtaaact ctcagtaaat actagctgct tttagtggct    20880
attcttaaca caccctcttc agtgctctgg tttcactatg ttttatgggt ccctgagatc    20940
gaaagtgtcc acaccgactc atggtcagct gtaacctgtg cctcgtgtgg ggaccaggct    21000
gccatgtgta gtctggacag tgtaggaggt ggcagagctc aggcctgttc tgccctccag    21060
cccagagagc cacgtcgtta gatgtcatgg gagactgtgg tgccccggga atctcacgaa    21120
tttgcccacg gtactcagtg tctgtccaat gctatgggag tccaggactc taggagccag    21180
ttaaggtgct gggtggccac aggtccctgg ccaaggtcca ggcctctccc ctgccacctg    21240
atcctcgaga ggccatcacg agggttgtac ttcaagaacc actatccttg agctacctag    21300
gagctgcaga atgtgcactc tgcagggctt agggcctgca gacaagatag atgcagggtg    21360
tctagttaaa ttcgaacttc agataaacaa caaataattt tttcaaataa ttgtgttcta    21420
```

```
ttcggtccct atttgggaca tatttgtact aaaaagtatt catttatctg aaattcagat   21480
tcgactgggc atctggtgct tttgtttgct aaatccaaga gcaaatttgt tctagctact   21540
tctcaacccc accttcagag aggaagcctt gatggtactg taacatcatg ctgtaagaag   21600
gggatcsctt gaattgtaaa tggcactctg ataagatgag gtatggggat tgtattggtt   21660
tcctgttgct gctgtcataa attaccacaa acttagtggc ttcaaacaac acagatgcat   21720
tatcttacag ttctggaggt cacaagtctg aaagttaggg catcagcagg actgcattcc   21780
ttactgcgga gttctagaga aaaatccatt ttcctgcctc cttcagcctc cagagacacg   21840
ccacattctt tggctagtgg tctgcttcca tctccaaggc cagtggggc ttatcaagtc    21900 tttctcacat cacatgactc tgtttcttct gcctccctct tctacattta agggacctt    21960 gtgattacac aggggcccac ctagaaaagc caaaataatc tccttatttt aaaatcagct   22020
aatcagtggc tttaatccca tctgcgatct taattcctgt cgccatgtaa cacaaggtat   22080
tcccaggttc tgtgggttag gacgtgggtg tcttcctac cacagggcag tttctagtgt    22140
tgcctcttct ccctgcagtt cgctcatgga gtccggacc tggcgctgaa ggacatcgcc    22200
tgcagcgagg ccctcctgga gcgcttcatc atcttcagcc agagacgcgg ggcaaagacg   22260
gtgcgctatg ccctgtgctc cctctcccag ggcaccctac agtggataga agacactctg   22320
tatgccaacg tggacttctt caagctcttc cgtgtggtaa gggagggtt tggctgctcg     22380 ccaattgcaa ggtgattcct ggggtagcag agcctcacga attgaccttg gggagggcgt   22440
gagcctggtg ttctggacaa tccttgcaaa agctccaggc tcccagggct caaaaaatca   22500
caactgatag tatttctaga acagtggccc agggacccag aagtcactat gaggttcacc   22560
attaggtatg tggctgtggc atgtttgtgt ccactctaaa tgtggggata atcccctta    22620 cctcctctaa cagagtggta aaggaaggag gaggcctggt ttgactccct gacctgctat   22680
ttcctagcca ggtgatcatg gtaagatatt gaaccttttc tggtcccagt actcatctat   22740
aaaacaaata taatactttta cagagtggta ggaattatac aagaaaagta tacgcaaaac   22800
atttcataaa ttttaataaa tgatggcccc atgcttcttc ctctggaaat ggtctcaacc   22860
tcaatggttg gtgtttctag agagaaaaaa cgacagagaa agtttcatag tctcaaaaat   22920
ttggaaagcc ctgatctagc tcaacccttt gttctagaac tgcatcccag acagactgct   22980
tgggacctga aaatatctcc tcctttgcta gaaggataag atgagaagga attagataaa   23040
ggaggtgtag agcagaggtt ttcacactgc aaagtgcata aaaccatca gagggccggg    23100 cgcagtggct cacgcctgta atcccagcac tttgggaggc cgaggcgggc ggatcatgag   23160
gtcaggagat agagaccatc ctggctaaca cggtgaaacc ccgtctctac taaaaaacac   23220
acacacacaa aaattagcca ggtgtggtgg cgggcgcctg taatcccagc tactgaggag   23280
gctgaggccg gagaatggcg tgaacccggg aggcggagct tgcagtgagc cgagattgcg   23340
ccactgcact ccagcctggg tgacagagca agactccgtc tcaataaaaa caaacaaaca   23400
aacaaaccaa aaaaacccat cagagaagtt ggtaaaagat gcaagtgcta aatccccacc   23460
cccaatcact gtgattcaga agaaccaggc caggcccaga atctatcctg ttaccttagg   23520
cgattctgat gaagaccatt gtaggccaca cttcagaaa cactcaaaat tagaatcctt    23580
cagagaaggt ggcatatata atatttctag catggaatta tgtttttttt cttttgccta   23640
cattttaatt tctagaactg tgttgtaggg aatgtcagtc actaagaact tgattgagga   23700
actgtgtttt gtctgtttca tgactgctct ctcaagtccc aggaaactca ctttcagctt   23760
```

```
gtcttaaaaa gcaagctgaa ggcttttaaa aatgaagcaa catgaaataa gacaccgcag    23820
tttctggcac ggtccacgct taatccccett caatgtgtga cttteegtgg aaagttactc    23880 tacgattttc ccagctcgtc agggtggggc cccagagtga gtatgaaggg tcagagccta    23940
gggatgccac catcagtgag agcccaggac cccagaaaag gtctcttggc tcaccacact    24000
gtaggaaaaa taaaaagcaa tgtagtccaa atgtctctat ccaaagtttc aaaaagaact    24060
tgattttaga cacgctcctt gacttgtttt cagaatcaga cagaagagtg aggcaacaaa    24120
ggtcccttat tccaggcagc tgaataccag cacagccagg agtccagtgc tggtgtttgc    24180
agagccacca gaggctccct ctcaggtgtc cagggcccgc atgctttgta gaatgggcag    24240
aatgagcaat gtctgtgcac ctgggctttg caggcagggc ctgggtaccc aggttcgtgc    24300
aatcctctcg tcaccatgaa gggagcagca tcattcttcc cttcttgaag caccttggcc    24360
accagtatag gtaaatttac ctcccaggac atgaccattg attctgggat gtcaatgcca    24420
gagatagtag ggtaaatcgg cacctgggta aaactttcca ttggagacta gaaccaaaac    24480
tcaggacact ggcttccaaa tgtttcttta tcagacaaga aagaccaagt cttttccttac    24540 gtcttcacat gctgccttgg caaatgctag cattcacaaa ccctgggcta ccttgacctg    24600
tcacccttgc agacctcaga cgggtcctgg gggcttgctt tctcggtttc tgtatgcagg    24660
cactcaaacc tgcatcaggc acctgtgaag ggccgggcac tgtgctgagg ccaaggctcc    24720
aaatgtgaac cttccaccct cactgaactc acagccagac cagagacaag caaacaggac    24780
atttcacagc agtgcagcct agaaagggcc aacaccagca gcatttgtcc ccccgagcgg    24840
tagcttttag aagcttcccc agtgattcaa tgtgtcctac aaatgcctgg cccccactcc    24900
cagagattct gagtcagctg cctagggtg cagccttgac ttcactgtgt taaaaagctt    24960
cccagataag tccaatgtcc ggccaagatt gagaatcact gacctagagt ttaatttacc    25020
acctcagtct ctatagacca cgcataataa tagtacccca cacacctctg agggtccaaa    25080
gaactttcat ttgatcaccc atgagaccac cgtggtgtgg agatgctttc tctctcctgt    25140
tctcttaaca aagctggtga gcgacagagc ctgcagtgga ccgggagatg gcccagagga    25200
gaaagctctg ccgtagtcgg cctcagttaa ccacggagca ccaccccctac ctgctctcct    25260 ctcactcctg cttccgtctc ggtggagaaa gatccaaccg aagcaggaca catctagtct    25320
tctggtgcct ttaaaatgta cttttccatt tgacaaatgg attacactaa aaacaaaaat    25380
ttacaaaaaa aaaaaaaaa cctgaaagaa attgcaggca ttaaaatggg actttgcctt    25440
tattgctcct gggcccatcc tatttgggtt tttagaaaaa caagcctgag gcaggcccag    25500
aaaggctcag ggcagaccct ccgatcctct gaaaggagca tcaggcaggc aggggttgct    25560
ccggggccag ggaaggggcc ccgctgggac gcggctgtta ttgcagctgg ttggcgcgca    25620
gccatgctta gctgcagtgc gggaatgctg ggccttctgt tctgggctgt ttctcatacg    25680
cacgtaggcc agtgtataaa taaggtttta ttaaatgcca aatgagttct cattaacaaa    25740
gaaagaggga aaatctcagt aaaccaccgt gacggcatct acccactttg agtcaggagc    25800
tgggggtgtg agtgcaacct ccgagacaag ggaacctgtg gagcccagag aatcggaggg    25860
gggcgctggg gttagcaccg actgagacca gctgtgtttt ctctcggttc cttggagatc    25920
agaagtgagt gttgtcatct tcaaacaatc caaaggcagt acccatggcc ttactacatc    25980
cctcccacac catcccaccc atcccgcgcg gtacactcac acgctcattt gcacactatc    26040
gcacacgctc acttgcgtgc gcacacacag attggtgacc taggtggact gggagagaaa    26100
taagagccaa atgactggat tttctccaag gaaatttatt aatagcccct cttggtttca    26160
```

```
cctgaaggag cttgtcttca cctgcggcct ttgcaggctt aacgccccca gcttgaaacc   26220
cagaagctca gacttgggcc caaggtatta ttagtgccaa cactacctga aatgtttcgc   26280
acctcataaa aatggtgtgt cagtttcggg tgagaggttg ggacgcttcc catctgattt   26340
ggcccaaggc atgcatgccc ctccttctcc ttcccctcct cctcccccct ttccccctac   26400
catccttcct gttttctctc caactctggt gcacagcttt gaaatcttgc tgagaagcaa   26460
atctgtccct tctgctttga atgtttattt gtggaagttc ggcaggggaa ccgaggcggg   26520
tgccaagacc tgccatgctg ctgggaagtc tgagtctccc tcccttcccc ctcctaaatg   26580
cttgttgata gagaaaagtc agcctcctcg gcatttgggc tcacggtttt cctttgaaaa   26640
tgcttccagt gtggcatgat tcagctttct tttctgtccc ccaaccactg ctctgttgtc   26700 attttttactt ttctgattgc attttatccg tgtctctttg actacggggt ggctggacgt   26760
tgagttccag gaagaaaagg gcccaatctt ggggttctga ctacatgcgc ccatcaatgt   26820
cctgtttcat tcttggctct ggctcccctga attcctgagt cactggggag aagcgtgggt   26880
ggaccgcccc ctacccagtg agagttgcca cagttgctgc tctcctgggt cattggttgc   26940
agattgttaa acttcaccta tgcatttcaa ctttcgggtg atattgcta cgtcaagtgt   27000 ctgggaaagc ccccacagct acaggatttt acagtgaggt cccactaatg acttgatgtc   27060
atgacttcct cattctttcc aatttctccc acttctccat aagggttttg ggaaggggag   27120
aagagaaagg agtgattcct gagtgccagt accagggaac agcagggctg ttgggaggaa   27180
acaaaactaa atcaggaagg ttttgttgt tgttttgg gggttttatg aaaatattca   27240
agccacagca aatatatttg atttatagca ttagtatttt ttctgcctgc atctacaaaa   27300
atctttacct attaccatca aaatatcctc tgggtgaatg gatttcaaca aagaagaaat   27360
aaaaatgaaa tagaagagag gcccccttcgt gcacattgag cctactggct ggattgtcac   27420
ttgcctgcct tgatgtcttt tcagctccag gcaggcagta ggccagggct tattttcatg   27480
acagatcaga tgttctttta tggatttaca aagaaagaaa tactgagaag tcaaaactga   27540
agtcacttaa gacaagagca ggcccctggg aaggctgcca ttgaggataa tgagtcctgg   27600
ggtcctggcc tttgttcagt aaatacgcac taggcgccta caatgtgtgc accaatgtgt   27660
gaggcgtcag gttctctcca gggtcagttg gttttaagaa aggttttggc ttctgatatg   27720
ttttatctct acagaacagt agctcttaac cttttcttatg ggttaggatt accttcgaga   27780
atctgactac agctctagac ctgttcccta aagaaaacta agttcacagg gacacacagg   27840
atggggctca tggagcagct gaagccagac cccaggttaa tagcctttac attaaaatgt   27900
ttttctacct accactaata tgcattcttt agtaagcggt ctcaatatac accgattctt   27960
ccttaactct gtttatgaag tattcagcat cctccctgcc cccttcagca tcctccctgc   28020
ccctgagcac aggatccaat ggcgtgagga ccacaggcct gggcagctgc tgggcatac   28080 aggcatctct tagtggctga gagactgggc cctggctcta tgttggctcc taacttgctg   28140
ccatttaaag gaaatcttag cctcccatcc gtaaaatcga gaaataaga cttgtcctac   28200 acagctcatg aaatagtaat gaaattcaca ttagagaaga gatggaaaaa cactttgaac   28260
aaaaagcatt ttgctcttat aaaagcacag cctcttttga gaggcccttt gctccccatt   28320
tctccttctt cagacccccc cagactagga gaaggtctgt ctcatggagt gacctttggg   28380
ctgcctctag attccaagct cagttttgct ttcattaacc acagatactg ggacggacag   28440
aaaaagacct agtttctgtt gagccaaaga gtctcataac ttgtctgttc acatacccaa   28500
```

```
gagcccaccc tctagttgag acactcagtt ccctctcatt ctgggagact gcatgtctct   28560
gtgacctcct ggtagagacc gtttgacatg tcccccaacc ccccagtgat tgagtctgaa   28620
ttctccactg atgacgcatt tcctagcact cagggtgtcc cctcctggtt gccccctcac   28680
cactgaagcc cgcttcctcc cttttcattt gatgcttaac aactgtcagt ttgcaagaaa   28740
catgcttcaa atccacattc tcccagttgc ctagcaacaa cttccctccc ggataaatgt   28800
gggtttcctg tagctcagcc caggactgaa cacagcagca cacacttctg tccactgctt   28860
caactgcttt tcacctctgg tctgcatgcc ttcaagactg cagctcatcc ctcccttcag   28920
aaccttccat agcctgcaga ggccatgtct gccccaaaaa gacacattga acctgaggct   28980
acttatttac ccttgtgtta ggtatatcct caacttagaa attaatactg tttccagatt   29040
gtcttctttg aatcacagaa agtaaaacaa caaaacattc aatgcttaag acatttcatg   29100
tgcggttggg tgacatctgt ttgatgaaca catttgatcc aaagcatcag aaatactatg   29160
ccaacaagac ttttttaggag gtgataaaca tgtctgttct accttaagaa aaaaatatta   29220
cacagtccca agggagagac atggttttga tcccagacaa cccaagcaga gacctcttag   29280
ggccggaatc atcttggctg ctgcctagga ccttatatca atttcttaag cacaggatca   29340
aggcctaaag gccccttaga ctgacctcag ttagtagagg cagatccctt cacagcctta   29400
tcttccttag aggtctagtc tgaccttgaa cttcggctgg cagtgctgtc agttgtgatg   29460
tgtgacatgg aagagttatt tgttacttgg aaaattaaga gaacttattt ggcataggaa   29520
attgtgtgtg tgtgtgtgtg tgtgtgtgtg tgtgtgtgtg tgtgtgtgtg agatgatgtt   29580
tgccattttg atctgtgact ttttttttcca gaaatagttt ctcagttcca ttccaactaa   29640
acttacagtc tcttccggtt ctttgacaga acaattcat gtgaatttga acagataata   29700 gggaagggggg aaccaaaaga agaggagagc cctgggaaag ttattttata atttatggca   29760
acctcagtca ggcaactgtg aacaggtaca tatggagggc tccctcggga ctaggcagta   29820
ttcagagatg taaggtgtga ggaccggacc ctcatcattt accattccca ctaaaaagag   29880
ctgggaagga aattgtagct gtagcaccag gcacgtaact ggagcttagt aactatttgg   29940
tgaaggaata ttattaaatt attaacaaga tggaaaaaag ggtattaacc acacaaaaat   30000
acatctcaag ctattgtttc tctgttccct ttcccccaaa ttcctagtct tgctcttatc   30060
tggctgtctc tctagtcact cttttcttgct gactctcttc acgttccttt ctccacctgg   30120
aattcctggg ccctccccctt ttactgacag acactgtcct cactctcaca gtcatcagtt   30180
tgtctcttta caaacctcag ctcaagtgtc acttccccgt ccccaggtga aactgactgc   30240 tccctcccctg taagtcacca tgatgactgc tatatatagc cctcatggaa cctaaaacct   30300
caacagacac agtctctttc ctactctgtt atagtttatt tactcattaa ttaccacaac   30360
acgtattatt gagcacctac tgtgtaccat gcccagaaga taaaagacaa acaaaataaa   30420
acctattcct atgcttaatg agtttacagt ctagtggaga gatagataca ttaaaaaata   30480
acagcaaacc aaaataaaag tggtaaataa atgcactgag aaagacagga atagctagga   30540
ggggcaccta atccctaggg aaggaaagct ggaagagcat ggtgatgggg gaagaaggct   30600
ttctggagaa ggtgaggtag tttgaaatga gttgactctg gccagtaggg gtagagtgag   30660
aatggggtga gacagggtgg gttggtcatt ttgatccatt agtcctcaaa gtgataggac   30720
tagtggctaa ggactgcagg ctttacagaa gcctacaaaa ctatttgaga tttgaagttt   30780
tttttttttt ttaattggct ccaaaagaaa atgaaaaaac tttagaatta taatgaatga   30840
atattaaatg aatatttaag gaaggtaatt ttattcaact tcattgttaa atttagttaa   30900
```

```
aacaagccct tgagtttcat tcaacactgt tttatcatac cgttgatgag agaaaacaaa    30960
actgattcct ggccagggcc actgtcagcg tggggtttgc acatctttcc catgtctgct    31020
tgggttagct ccaggtactc ctgtttcccc cacatcccca agatgtgccc attagtggaa    31080
acggtgtgtc tgcatgattc caacgtgagt gagtgtgggt gtgggagtga gtgcccctgc    31140
catgggaggg catcctgtcc aggttagatt cctaccttgt gccctgagct gctgggatgg    31200
aatccagcca cccatgactc tgaactgaaa taattgggtg aataattatc ttacttttta    31260
attaatcttt gaaaatgtat gtatagttca catgtatttc aatatttaat attagaagta    31320
ttttagtctt tattttgaag tttggtgatt tattgtaacc agaaacaagc tatagaaact    31380
taattttggg ccaagtgcag tggctcacac ctataatccc agcattttgg gaggccgagg    31440
cagacgcatc acttgaggtc cggagttcaa gatcagcctg ccaacatgg taaaaccctg     31500 tctctactaa aaaatacaaa aattagccag atgtggtggg cacctgtagt cccagctact    31560
tgggtggctg aagcaggaga atcacttgaa cccgggaggc ggagcagtga gcagagatcg    31620
tgccactgca ctcccaccta ggcgacagtg tgacactcca tctcaaaaaa aaaaaaaat     31680 agaaaagaaa gaaacttaat tctggtttat atcaattagc ctgtggtaaa attggtttca    31740
ttatagccat ttcacttagt tgaagtttcc aataacctgt ggatgaatta agtgaggatt    31800
tactatattc ataaaatctt aaattccaaa gcctgtttgc agttcaggtt tttccacttt    31860
acaaacactt ctaagtattc acaatgattg cttaaaattc ataccagata aatcattaaa    31920
taagttgttc aaagtcaaat aatttcataa gtaaaaatta ggagctttta gaaaactata    31980
cctacataga cctagaccta tagatagaca gagatctgaa tagatatgga cacagatgct    32040
ttccaaagtg ttcatgtgat gtgtggtgga gttttcaagac cagagtgtgc ctggggcctg   32100
cagaagtaaa ggagagggga tggagagaag attgtccaca tggccatggg caatctccca    32160
cccacactca agtgaggaag acaggaaaca aattcagaaa gaagagaaaa taatcaaaac    32220
tgatgggagc ttgtgactga tttacttatg cgcagcctcc ctggagacat gagtgtggct    32280
gttccttagg ttgtgcctct gggctcctac cccctcttag atgccttcct attatctagg    32340
acctggttgc tttttgtctg catagcttct ttggattcca gtctttgatg ccagcttcct    32400
cctaaagtag cctttcagat gtcccttggt taccctctgc tatctaaggg ctcatcctac    32460
cccacactca ttcccagcac caatttctgg atctccaggc tggagattta gacaatggga    32520
tgggaagaac ccatgatggg tcccagacag aaagtggtgc cagccacaga aagggcacac    32580
aggcacagaa gttggtttgg ggtaagacga tgtggtcagt tcagaacacg ctggatctag    32640
gcagatgccc agcagacagt tggatatgta agtctgaagc tctggggaga ggtctaggtt    32700
ggaggtacag atttagaagt catcaacaaa aaggtagcag attaaatgat aaaggaaatg    32760
agactatccg gggagtgtgc agagtgagag gagcaaggga ggcccttggg aacctcagca    32820
cttcagggga aggtagaggt acagttgctg gtggaaagg cagagaagta gcaaagcaaa     32880
ccaggcaaaa gcagtgtcac agacgaccag ggaggaaaag gacatgatca aaatgttgag    32940
aaaagcagag aggtttgaaa atacaagaag caaaaatgtc cactagactt aaaaaccagg    33000
agaaaactgg ggggttcttg ataaagcatc ttagtaggat ggtgagggta gaagccaggg   33060
aagtgttggt gaggaagtga agtcactgat tacggactat gcttaaaaga atgtgggaat    33120
gaagggtgga agagagaaat tagactgtag ctagggagac ataagcgatc agaggtagat    33180
tctttctctc ctgtgggaga atcttgcacg tatacacagc atgacgacag tgatggaagg    33240
```

```
gctggcgaag cctcagggag actcttggag gtaaacccca tgaagggagg actttgtttc    33300
attcactgcc gtgtccccag cacctggcac aatagcagac actcaataca tatttgtcaa    33360
atgtgggatt ttatcattta gaaactgcac ctggctgtga gtaacaaaag tcagagaaac    33420
cgtgggtttc attttctcc ccaggcagag tctggagctg ggtcctccaa gaggggtttg     33480
gagcaccaca ggtttcctca agaccccag gctgccctgt gtttccctcc ttcatcccca     33540
gcatatgcct gtcatctggt gacctccaaa cacctgtgct gcctcctcca gcacatccat    33600
gttgcaggca gggaccaggc aaagggcaga ggggcctact tcaaaagacc atttccagaa    33660 acccatcct atgacttctc ctggtgtctt ggttaccatt gtgccatagg ctcaccctgt     33720
atgcatggga ggctgggcca ggcattatga cttttagcaa tattgcatag ataagcatca    33780
atctttgtca ctgtgacgaa gcctagtcac tcagtgctag gcaaggttaa tggaatgggt    33840
tggtgtgtgc attattcttg aggtctttct tatgcttcat gttatacatt tattaggacg    33900
tttaggcaac aggggataa aaatgaagag gagatgcatg ctatgatctg aatgtttgca     33960 tcctcccaa aattcatatg ttgaaatctt catccccaag atgatggcat taggaggtgg     34020
ggcctttcgg aggcaattag gtcatgactg ggattagtgc ccttgtaaaa ccccagaaag    34080
ccagcttgcc gcttccacca tatgaagaca cagagagaag atgccatcta cgaatcagga    34140
aatgagcccg caccatgcaa taaacctgct ggagccttga tcttagactt cccagctgcc    34200
agatctgtgg gaaatagatt tctgttgttt acccagctta tggtattttg ttgtagcagc    34260
cagagtgaac taagacagtg ctgatctcgt attcttggag ggaaccctta gtctttaggg    34320
aaagcaaagc caccatttgg ggcagggtgt tctccaagtg ctgccacata tgctgatgtg    34380
gttaaactgc aaactatggt aaaaatgtgg aggtctgtgg aattgtcaat caggaaaaag    34440
atataaaaag aagttaaagt cttcgtgctt ctggaaggat atgtgccaaa ttgttaacat    34500
tgattatcct tgggtagaga tgtggggaag tttgcagaga cagttttgcc ttgtacttta    34560
tataagtaaa cagctactac ttcgttgtct taaaaaaaaa aaacagccta tgtgctcttc    34620
atgtgactca gaactaccta ggcaatacga ttaattgaat tagtaaaatt gagtgattat    34680
gaattttcag gaagtcatta atttaccact tctttattac atccacttct aacaggactt    34740 caatatagg gaatttgact tcaagataaa aagaccaaat ttatttaccc ttttaaaaaa     34800
agacaactta aaagcagact tgtcttacag aaccttcctt agttggacat cgatgagtgt    34860
acagaaaatg caatggataa aaagcttggt gatacaaaga taaaaagtgg ggtcctgtcc    34920
ttaatgaaca taccatttca tggagtatca ggtgtataaa caattataat caatctgctt    34980
gttattctga taagatcatt tactcacaca tcaaatactg agtgcccacc acatgcccag    35040
catacctaga agtcatccag tatgattct gtctacatgg agcatagagt cttacagggg     35100
agatagatga caagtaaaca ccagaataat taccaatggt gaagagcaca aggaaggaaa    35160
cagaactcct aaagagagcg tggctgggca ggggtgagca agaggcatag aaaaagggc     35220 atctaaatct acttgggagg aagctgtttc tcacataggt catcatgtta ggaatgagac    35280
ttgagggatg agtagaagtt tgccaggcaa agaaggaatg ggggggaata gagagcagag    35340
ctaggggcag gagacagctg acgtgtgagc agacataaaa agaagtccac tgtggcagca    35400
gagaagcagg agagaaggca agtgagggag ccaggcacca gctcacagag gtcatgtgtg    35460
tcaaaacgta gtaatggcct tctccttctgg agacagtagg gagccatgga agatgtttga   35520
gcagggaaag cgacatgact ggattggcct gttgggtaac tcagaccaca atgcattgga    35580
agggaggggg ctagaggcaa ggggactggc aagaaggcca gtcctttttc tatgcctatt    35640
```

```
ttgatgaaat attctagaag ggaagtgaac aaaggtagtc ctagagagga agaacaaaac    35700
agataggata cttccttagt atttgctcat tcgacaattt atttttgcat atacactaaa    35760
acctttttta ttattaaaac gttttattgt aggaaaaaag tatgaaagta gagtgaataa    35820
taaaatgagc tcccatggat ctatcaccca gcttcaacta ttatcaatat ttggctgttc    35880
ttgttttaac tgttctccac cttttttttcc tgaagttttt ttgaagcaaa tcacagacaa    35940
catatcattt caccatatgt acttccctct gtatctctaa catgtaagaa cttgttttaa    36000
caaaatcacc atgctatgat catacccaac aaaatttatc ataatgtctt aataatacct    36060
aatacccatt tcatgtccac tttcccccaa ttgctacagc tggtttgttc agatcagaat    36120
caaaatccac ctgtggccat tttactgcta tgtctctcag gtctcttttc atctctaata    36180
atctcagggg agacaggagg gaggacgggc aggacttggg gctaacttgc ttatcgacac    36240
acagttttgc ctacttgctt cctcccttca cacccactct tcttctcagc cccacccttg    36300
tatgaaaaaa acagaaatta aagtgctttg cccagcaccc actgaagcta tttcgaagga    36360
gtttgaagag tactcccggc aagacaaatg cctcggtcca gtgctcaggt caaagagggg    36420
agacgcttct cagtgatgtg gtgtcaatag cagcttagtt gttctttcct ctggaaaatt    36480
ctacccatct gctttgtaac tcccatacct aacaaggcct tttatttcac aattagaaaa    36540
taagcctgaa atatgaatgc tgcctgagtg tacctacatt tattctagag tttcagggtc    36600
aaaaagaata caaggacctc tgcatctaca gccaagagga gaggggcaaa gacacacagc    36660
tacaaatgag aacctggctg gtcaaagcct aactccacct gtttgtcagc actgatgcaa    36720
gttaggtcag cccaatgatc atttaggaga actgtgctgg caaataaaaa gcagaggctt    36780
ttggtcccca gatacttgga tgagaattac aagtccagct ggttaaaagg cacatgccca    36840
gtgctcactt cacacctact caggaagcac acttgagttg gaaaaccact gtctttacac    36900
ttagaactca gtcctacatg actcctctag gatcagtgat tccatcagtt ttgaaacatg    36960
aagcatgaag tcaaacagga catgaccttg gtttccagaa accagatgt tcacatcagt    37020 ctctggagct tggaggcagc acacctgggg acttccacat cccctgccga ggtggcaaaa    37080
gcaggagcag tggtgagttc acatgggctg gggtttcctg aacactgctg gcaattggag    37140
aatctgcaag ggaacttctc cgactcctac cagcagctgc tttaaaataa aggtgatgta    37200
gctggtcaaa tcctccatga gagagcagtg ttgaatggag gaagagacac aacctgtctg    37260
aaaatggcac aaaggaagaa agatgtaaac aatgacgaga agactgcagt gtctacaaag    37320
ctccgaggta aacagatggg caccccaggc ccgcagcact tccttcagtc tctgccagct    37380
gcactctgtt ttccttcctc caggaatctt gtttggtgtc actaaaacag caattagaat    37440
cactttgaaa tagtgatagt atttaatata actatgaaac tatctgtgat tgacaagtgc    37500
agcaaggagt cttggaatga gagcctttat tttttcaatt aaataaaaga gttttttgtt    37560
tctaaaagta atcttgcaga aaagatcctg cgatcagaaa gaaggagggg gggagttttc    37620
aaacatatag gagatcagac tgtgcctatg tgtgtatata cctacaaaca tatatatatt    37680
taaaaaattg ttttactgtc aattacagct tcccacactc ctagacagcc gttctcaagg    37740
tatcaatctg agatcttggg gaggaatatt atctgatatg tcaccaagaa ttcaagaggt    37800
gagtagcctg atggtagtaa ttataatttc attatgtctt tccaccattt accccactta    37860
tgtcaaataa tttaattgta tttcaaacct gttcaaggaa aagtacattt gatctttcca    37920
tctagcaatt tcaaagcacc tgttcacatc ccaaattatc tgtgctctta agtaagaggc    37980
```

-continued

```
agaaagaaag gaaccaccct tctgatttca catcaaaaaa gaaatgccac tggcaataag    38040
caacttgcct ggtgtggcat aaatcatcag aagacttaca gttgaatcta agtcttttca    38100
gtactgaggt ggttcattat tctgttacag tcttaaaatt cacataaata tatactgcca    38160
ataataatag catacacctt tatagcttac aggcactctt cttctaagtg ttttacctat    38220
gttggcttat ttcatcataa agaaaacaat ggacttttgt gttgttttgt aaaagatgc     38280
gcacattta attaacatct gattgcacaa gtctcctccc atatagaaat ggattcttcc     38340
acgcaataga taagaggtgc tggggatatg atgatgaaca cacagatttg gtcatgaccc    38400
tgtgggaaag agagatggga aaaaacaat tctcttcaag tgtgatgagt gttacgaaag     38460
ggagggaaaa gttgaaacag gtttttttcc aaacttttct ccctccatta ttcgcagctg    38520
acttgggctc caccaacctg gaaaactgca tggttggaat ctgtctttat aaaacgcatc    38580
tcaacctggg ccgagtatgc acactgatgt gggaaagtta gagaagagcc cattgtacta    38640
atgctcacct gctacagtgg gagtctctgt taaacagtct tttcttcata gcattaaaaa    38700
aatttatatc actacaataa ggttgaaatt gatagagaat gtacaaacaa tccccaaagt    38760
atatcaacac tcttagttct gagtagaagt tccagaaggc ttcttgactg tctagatagc    38820
aagtctaatc atttgtgaac taagttaaag cagaaggccc agtttatatg aattggtatt    38880
acaccatttg acctgagaac agccccttca tctctgagtg ctttgactaa atgagcaaca    38940
taataatagt aataaccct tacaagatgt cataagactc actgttgttg aagcaatttg     39000
agattttgac tttattgaag catagatggt gattataggc atgactcact gtgtggattc    39060
tccctgggct catcagtttc agagggcaag tgttggcatg tggacaaaga gagggatgac    39120
acgtaaacat ggcttattgc aatggggaaa tattttcagt ctcactgatt gaatcctaat    39180
ggttttataa attccccagt accactgaaa gcaaagcaag taatcaggtg tgttttagga    39240
ataaagcag cattattta atttcgtatt ttcccctaaa gcaaagccaa atggcattat      39300
gggagccaag ctactggcag ctccaccagc cttctcctga gttctcggca ttacagatct    39360
accctcaaag gatgaggcca gcaagcacca cagggtgccc acatggagaa gagaaggcca    39420
ccaacctcct cttagctggc acagaattga aaaagtgttt ttccaggaat ggatacttca    39480
tctgttctgt atttgctaga atttaaaac gcacacacag acacacacag gcgtgcacac      39540
acacacgcac acacacgca gaaaaccaca aaccacacat ttcaaggaaa tggaagaatt     39600
cattggtaaa attaagctaa taagattatt ttccaaatat aagaaactaa atttagact     39660
atttagccaa agaaatttgc tctgatcttg cttttctaca acagaatcat tccccaatca    39720
ttttatttcc ctcttttct ccccagtatc cccatcttgg tgggacaaca gaacccaaga    39780
actggcttaa cagtaaaata ttttctgcat tgcccaagg acacattccc aacgaattca      39840
aataaaggag actagaagaa gagaggctat actacagtgc tctaggggtc actctgtgat    39900
ttgttgttgt tgttgttgtt gttttgagac ggagtattgc tcagtcgccc aggctggagt    39960
gcagtggcac gatgtctact cactgtaagc tctgccccc aggttcacgc cattctcctg     40020
cctcagcctc ccgaatagct gggagtacag gggcccgcca ccatgtccgg ctaatttttt    40080
tgtatttta atagagacgg ggtttcacca tgttcgccag gatggtctcg atctcctgac     40140
ctcgtgatcc gcccgcctcg gcctcccaaa gtgctaggat tacaggcatg agccactgcg    40200
cccggccact ctgtgatttt ctttaaggct catcctagta ttctcctagt ccctaagtag    40260
atggcagtag gttttgtttt tgttttttcg cagctggatt aaggattgct gagaatatat    40320
ggatgttttc ttttaaatgt ggaagtcaaa ccaaacgttg gagcattggc ctcacagcag    40380
```

```
attatgactc tagctgcctt aaaataacct gaagactttg ccttgcccta gtttatccat    40440
cggccgagta tgcaggactt gctgtgggtg accaggcccc tcatgcagaa tggtggtcca    40500 gagacccttta caaagctgat gggcatcctg tctgacctcc tgtgtggcta ccccgaggga    40560
ggtggctctc gggtgctctc cttcaactgg tatgaagaca ataactataa ggcctttctg    40620
gggattgact ccacaaggaa ggatcctatc tattcttatg acagaagaac aagtaagttt    40680
tctgagtcct gcttataaat tggcctctca tgttggttaa gttgatggtt taacacttct    40740
aggtgaaacc aaacctgggg ttgcatctgt cttgtcttgc tgagtggcct taggtaaaga    40800
gacttctccc agaaagtcca cttccccttg cagaaagggg gcattgctta taagcaattc    40860
tggacatgaa ccacagaaag aactgaggcc cacttggaaa gggaacagag gggccatttc    40920
ccactgatgt aattgaacta gggctaagtt caagaggaag agaatgatcc gcaaggaagc    40980
aacccagagt tccaggtgaa gctcaggtca gaagggccct ggcaagtaaa cacggctgtg    41040
ggatgctttt acaaacacaa tatcgtgaaa atctatgtgt gtagtactga attacattcc    41100
aaatggcaaa ttcctggcaa atcatcttcc ccacctttca ctattttttt ttttttggtc    41160
ttctatgggg taaaggagga tggggtgggg aagaaatgta actggctgcc cctctagtta    41220
aaaactgaaa agaggcagca agggacatgc caaaagtagt tggactctaa gatagctaca    41280
cacaacaaag cagctaagca gctaattgaa gggaaattac tgaggctcaa gctgagattc    41340
caagcggggg ccttgtttgg cctctcagtc cctttcatct gagaaaggcc tcagttccta    41400
gcagtaatca gaggcaggct tctcagcctc cttctcctaa agcagaataa accacagggc    41460
aagtcgcatc ctttgtttct ctgatgaggc cattactgag agtcactgtg gcattttgct    41520
actaatgatg agcttgttat tggtggggta cagcctatta atttaggtta ttcatcaaat    41580
cctccagcat ggagttgaat gagacatgtg atgtggatac actaatgact atattgagtt    41640
acaagcaatg gggagtttct gtaaaatctg tcccttgtct cctggcagca tccttttgta    41700
atgcattgat ccagagcctg gagtcaaatc ctttaaccaa aatcgcttgg agggcggcaa    41760
agcctttgct gatgggaaaa atcctgtaca ctcctgattc acctgcagca cgaaggatac    41820
tgaagaatgt aagatcccag ctgggcttgc cttgtgtacc ctggacctcc cagaagtgtg    41880
tgtgtgtgtg tgtgtgtgtg agagagatgt gccttcctgg tagcacatct catgtttgtt    41940
ttttgctaag tggactcttg cgtttcctcc cccatccaca gtcatcactg gaatgctttg    42000
cttcagtgcc cctgcctggg ccctccccctc tctactgcag cctacaatga ggttttcttt    42060
cccattgctt gaattatatc cctaatggaa gggttcacaa ttctctgaat cctggctact    42120
cagataaaga cagggaggaa gggaggaagg gtattttctc ccaggggtc caaatctagc     42180 tttaacgagg gaggttctga gaaaataata tcatcaatat tacatggact tctgagatac    42240
taagaaatta gattctgtca gcccaggaag ttgggagatg gtgaattgtt ctgggaaata    42300
gcaatagact gagaaaataa aaacacttcc ttgaaaagcc tttccctaac actaagtgat    42360
aggggcagaa aagacacaac caaaagttct ctctcacttt tctctctgtt cgtgtctctg    42420
tcttgatctc tgtctggttt taggccaact caacttttga agaactggaa cacgttagga    42480
agttggtcaa agcctgggaa gaagtagggc cccagatctg gtacttcttt gacaacagca    42540
cacagatgaa catgatcaga gtaaggggggg ttggaggatg ggaggggag gggaggagga    42600 agcggtgggg gcaagaaagt tccacttgtt tccttttccc aggaaagagt taatcgctat    42660
tggagttaga tcaaaataca acaagcaggc cccaaaggcc ttcattccaa gcagtcacca    42720
```

```
agtggggtca ctgactttgg atgagaaata tgtttcttga attctgggag aagtctaaaa   42780
gctgccacaa gaccagtggc ttcctggagt ttcctacttt tatgaattca ctcaagggcc   42840
tcaaattcaa agaggcatct ccccaagggg ccagctctgt aactccaaag atggtggaat   42900
gtgtttgtct ggtctcattt tcagctttgc aaaatgaaga caagagttct atatatcagg   42960
gacactcaaa agaaaacaaa aatatccata agcaaagaa agctttttat acaccatatt    43020
caatgacccc catctggccc ctcctttgcc cctacacatc ttccctctat tctagagacc   43080
catggacttg gggaaatggg atatagatag gtatgtttca tagtggaaca agctcaccag   43140
ctcttcaggg agccttagca tctctatcct caatcactaa aaattagaaa tggctgaaga   43200
acaagaccaa agatcctatg gaatttctaa gcagagcagt gactgtattt cttcttccca   43260
aggatacccct ggggaaccca acagtaaaag acttttttgaa taggcagctt ggtgaagaag  43320
gtattactgc tgaagccatc ctaaacttcc tctacaaggg ccctcgggaa agccaggctg   43380
acgacatggc caacttcgac tggagggaca tatttaacat cactgatcgc accctccgcc   43440
tggtcaatca atacctggag gtaaggggct gcaagcccca cagtgggccc cttgaagata   43500
gccccatgag tggggccaga gctcccttag caagtcaagt ggtcttgaat ttaagctttc   43560
attttcccca ctgaagaaac aagaatccct acatcccctg tacagttctc attctctaac   43620
agcttatcca tacttaaaac ttatctatgc tgaaaacggt ttcctcttca catctcctac   43680
ttctcatgct gggcacctcc tcctgtagcc cccctttaagc atctgtgtct gtcctcaacc   43740
ctcttctgtc tgacattgct tgagtggcca tctatggcca gtgtcccctc aacccccacag  43800
tccattgctt gctggacact cctgccctca agttctacaa gcacatcagc ctcaacatgt   43860
cccctccaaa aactgtatgt tctccttgcc catagaacat atccttctcc tatatttcct   43920
atcctaatta acgtcctcag catttgcccg aattctcaag tgagggattt cagggtcatc   43980
cctaattttc cttcttcacc ctccacacag tagctgtcac ttactgagtg ttactttatg   44040
ccaagtactg tgccaactgc ttttacacac atatgcttca tttaattctc acagctccat   44100
gaggcttgca ccattatcat tgccaatttg cagatgagaa gccagggctt aaagaggtta   44160
aataagatcc cacgcatgac cattaagagg agcgaacagg atccagctct gggggtgcct   44220
gagttcagag cctgcctttc tgatttctct taccaagctt tgtctcctct ccctcctaaa   44280
tatctctcaa ctctgcctct tgcattccag gctctgag gactagaggc cttgtcatct    44340
ctgcgccagc ccattccaag ggcttccttc ctggaatcca gggtccagcc tctgttggcc   44400
caggcatttc tctacactgg caccagagtt acattccgca cacctgctta cgttgctctc   44460
tcacttaaaa tcttaatgac tcgaccccca aataacacag gtcccttcca aatctgtcct   44520
accccacctt cccagccctt gctcaactct gctacctggc cctttcacgc ctacaggcat   44580
tcccattcca tgacctcttg ggattctacc ctttgcaaat gctgttttca ttgcccattt   44640
attagagcgc ttttggtcac aagcttttg cttaaccaaa aagaaagcat ttattggtgg    44700
acataaataa tgaagttcag gaggatccaa gagttggaag ccaccatgag acccctgtgt   44760
ccttccacct cacttttcta ctcgcctctg ctcagcttca tctctggcca ggccctctcc   44820
tctgctgatg ccctagctgc ttacagccct tagcagtcat ctatacacca aaaatccctt   44880
tcccatagca gaagcaatgc tcctagagag tttccctgtt ggtctggctc ctgtacccac   44940
ccctgtgtac tctgattggg aggcctgggt cagctgccca ccatgggggcc atttctatga  45000
gcaggattac tgtgaagtgg aggaagatgt ttccccaaaa gaagaaacac aaggtagaaa   45060
agtgtatgtc caccaatgcc tgaaatgact gtcccttttcc tcatctgctg agcttctact   45120
```

```
cattcattct tgagactca gcactcagct cttaaatgtc acttctgctt tgatggaggt   45180
ttagtcattc actcctctgt gcttcctggc cctctcttca cacctctctc agaccccact   45240
cccagataga ttagagttgg ctgttgacat gtccatctct ggctgggcag ctaaactgga   45300
gttatttaga atcagggagc acatgtcagt cattttcaaa ttctcaacct catactccca   45360
gtaaatgact ccatctaagg gtggaccact cttgcccatg ggccaggtct gggtctgtgt   45420
catctagaac tgttggaagg taggggcttc tgtgagcagt aggagaggga ataaactcga   45480
gggccctcgg gagcatgccc tcttgtctca gacttgtgag tcctgaggat aacaaactag   45540
tgaagaaaag cctcgttcta tctgtcacct ggtgctcttg aggactttct gttgccctgg   45600
tgccaccaca attttccaga gtgtgtgacc ctcgctctcc aaactctgga agtggcagcc   45660
gaggctcccc agtggccttt cagaaggtgc cagtcatgac agcagcacca aactgcaggc   45720
aactactaag cgatcaccaa cttgtctgaa gataagaatg accttgaatg catttttataa   45780 aacaggattt ttttttttaat ttttagattt tctttcttta ttttaccttta agttctggga   45840 tacaagtgca gaatgtgtag gtttgttaca taggtatatg tgtgccatgg tggtttgctg   45900
cacttgtcaa cccatcatct aggttttaag ccccacatgc attagctatt tgtcctaatg   45960
ctctccctcg cctcgcccct accccacccc aacaggctcc ggtgtgtgat gttccctcc   46020 ctgtgtccat gtgttctcat tgttcagctt ccacttacaa gtgagaacat gtggtgttta   46080
gttttctgtt cctgtgttag tttgctgagg atgatggctt ccagcttctt ccatgtccct   46140
gcaaaggaca tgatctcatt ccttttatg gctgcatagt attctatggt gtatatgtac   46200
catattttcc ttatccagcc tatcactgat gggcatttgg attggttcca tgtctttgca   46260
attgtaaaca tacatgtgca tgtatttta tagtagaatg atttatattc ctttggttat   46320
atacccagta atgggattgc ctggtcaaat tgtatttctg gttctagatc cttgaggaat   46380
cacactatct tccacaatgg ttgaactaat ttacattccc accaacagtg taaaagcctt   46440
cctatttctc aacagcctca ccagcatcta ttgtttcttg acatttttaat aatcaccatt   46500 ctgactggca tgagatgata gatacccatt tgtcagatgg gtagattaca aaaattttct   46560
ctcattctgc aggttgcctg ttcacgctaa tgatagtttc ttttgctgtg cagaagctct   46620
ttagcctaat tagatccatt tttcaatttt ggcttttgtt gcaattgctt ttggtgtttt   46680
agtcatgaag tctttgccca tgcgtatgtc ctgagtggta ttgcctaggc tttcttctag   46740
ttttcatgat tttagatttt acatttaagt ctttaatcca gcttgagtta attttttgtat   46800 aaggtgtaag gaagggatcc agtttaagtt ttctacatat ggctagccag ttttcccaac   46860
accatttatt aaatagggaa tccttcccc attgcttgtg tgtgtcaggt ttggcaaaga   46920
tcaggtggtt gtagatgtgt ggtgctattt ctgaagcctc tgttctgttc cattggtcta   46980
tgtgtctgtt tacaaaacag attcttaagc atcaacccag atcgactggc tcagaatttc   47040
cagggaagag gcctggttat ctgcatgttt acagacctat tagatttgtg ggacctgcag   47100
ttcccttgta cagttagtta ctcaattaac atctccctcc tctcatggtg cctctacctg   47160
ctaagccctt attcccagcc aggcccacca ccatccaccc actgctgtta taacataagc   47220
aggacctgtg cgagggggtg tggacggagg agagaggctc tgttgcttca tttgtgcagc   47280
atggagttca gtggttctca caatgttttt gcaaagtata taaagaatac tccttgtcta   47340
cttgacattc gtatcgtgac ataaatgtct tgttttccag aaggattatt ttttccaagc   47400
agcttgttcc taatgcagcc ccaggcacca aacagatact taaaatatat taattgctta   47460
```

-continued

| | | |
|---|---|---|
| aatggttaag aaattcagtct ctggacccac actgcctggg ttcaaattcc tattatctgt | 47520 |
| gcccagtttc caagtctata aaatagggat attaatagca cttacctaat aggctcgtta | 47580 |
| tgagaattaa atgagctaat tcatgcaaag cactgacata tagtaagcac ttaataaata | 47640 |
| ttagcttttt aacaaaatac aagccaaaaa acactgctta ggagaggaaa tgatgttagt | 47700 |
| gcctcctgta aataggccca gcctccaagc tggtgctcct ctaggaatca caacgctgca | 47760 |
| aatcacatcc tccggggccg ccaggacttc acgagggcct ctgagcagag ggtatgatg | 47820 |
| ggagcagaag cccagcagct gtgatgatgt ggtttctgat cttcctgccc ttggggtggg | 47880 |
| ggaggaggaa agcaagggc aatgaacaga aaggagaaga tagcggggag gaaatgtgtg | 47940 |
| aggaagaaac acatcactgt ggcttgtcct ggattttct gcttctgttc tcgtgttttg | 48000 |
| ggaagtctgg aggagacttg aaaatcattc atgtccccac cctgaggatg gcttagtagc | 48060 |
| agagaggcca tgaaaactct ttgctgatgg ctctgaaagc aaggatgttg cttcactggg | 48120 |
| ctgctgaagg cctgcctggg ggttctgagc agagagtaca ggcccctccc aggagggcgg | 48180 |
| cctaaccacc atgctggcat ttctgtggac catggtctgc tgtctcagac cccctccaca | 48240 |
| ataggtctg caatctcatt caccccataa atacattctg tctttcctct gatcccctcc | 48300 |
| cattagcagg gggaaataaa tggaagtcag acggcccagt tagaaggcag gcagtggagt | 48360 |
| aggaaaatag atgatggtgg tttggggagc ctcacatcac tcatggggag acattcattc | 48420 |
| ccatgggcct tccaatcacc cttttctcca aatctaagga cacaggacaa atgggtcctc | 48480 |
| atacaggcaa atatcttaaa ctggtatgtg tattcattta tagttctaat ttatatgtgt | 48540 |
| ctttattcac atatattttg cttctggaga aaagctcaat tagaaaaatt aatacattat | 48600 |
| tcttcttatt gcccttcagc taaaacaagc atacacaccc ctcccctttg gatttttgt | 48660 |
| ttagcaaaag gttaggcctg gcacagatga aatactattc agagttcaca gtgtatttc | 48720 |
| atttcataat atatttgatt ttcaggtctt gaatttcaca tcaggaagct gatataggaa | 48780 |
| gctgaattca gccagatttt aatacgaaaa tacctctgat caaggcataa aattgtactt | 48840 |
| taaccagtaa ccactgtatt tctctaagct gtgaaaaaac atgcattcat taactgcttt | 48900 |
| ttcctctgct gtcaacacag tcaatacatg tgcataactc cttattgtct acatggtgat | 48960 |
| tatcttgctg atgaattctc aaaggccaga gatttggact atttttctc tgtaaccttg | 49020 |
| catgttcctg gccacatgcc accaccaccc aaacagaatg tacgcaggga atgtattttt | 49080 |
| caggataacc taagaaaaaa taggattaag aagataaagc tgctgatcat gtaatgtact | 49140 |
| ttagactcag atatataaat atttgtgaat tatctgtcct atttcttct tctattaatt | 49200 |
| cattgactct agatgtgcat tggaaggcta gggagaaatc aggggatcgt gagaaagagc | 49260 |
| acagaagtct gcatcacaca aacaatatta tttcaagagc catgaactag atcctaagca | 49320 |
| actcataggc aatgacctca tttcatacct ctagtctcta agaaacatat aactggcctg | 49380 |
| aggaaggaaa atgtgggcaa ggggtagacc ggggtcatgg gtggaggtcc aaatagtaat | 49440 |
| caatggagct cataggtgg actgatattg aagctgctat gagccagcca catgctgggc | 49500 |
| actgttacat gtcatctcat gcaatactcc caattacctg cctagtaagc ataattgtca | 49560 |
| ttttatagaa ttaaaacag actcaaagag gttgacagtc taatgtaaca caacagctaa | 49620 |
| atgggggatc tggaattata atccagagct gcctggctct gatgagaaag ctctttctgc | 49680 |
| tgtcatatgc agcccacatt aataggggc tcagaaagta ttctctggat aaattatata | 49740 |
| atgaatccaa tgaaggaaga cattatttta taatatgcag cataataggc actattatga | 49800 |
| ttggatttc ctgcttgaaa gtagctagat tagagtagga aaccaaaaag atgtgaattc | 49860 |

```
attcagtcat tcatgcattt gcatggattg agctacctac atttgaataa atgctgttaa   49920
tccctgattc cttggaagct cacattggag agataagcat gtcattaaat aatgccataa   49980
tagtggtatc tcagaggact agcagaacat aattcaatct dacagagtag aaacagattg   50040
tacaaatcca attcaaaaca tcataaatcc tctaagcact gtcaattctt cctccaaatt   50100
atctctgaaa ttcctccttc tttcccattt atggcctcca tttacagaag cgtgtactgt   50160
ctctcttagc tgtttgccag gccgccagtc tcttgctgtt cagctctcaa ctgcttccag   50220
caagatcttt ctaaaatccc aggcttgcca agacttagcg cccacagctc cacagtgact   50280
cctcattgct gttaaggtaa aggccttccc agtctagccc ttcatgcttc ttccatgttc   50340
tatgggactg ccccaggctt cccacctggt accactgagc cttccatcc ttcccccact   50400
cgactgccag gtcaacaccc acacccacgc ttcaggactc aggtcctatg tttcgggcct   50460
tcttctgtgc accattccct tccctgtagc ccttgatcat gatttgttta tacgcctccg   50520
caccttcatg gccctgaacc cctcaagggc cgaaactgcc ttacttttct ttttgacttc   50580
ccaacttacc ttagtggagc tgtagtcaca tagaatagac gctcataaat gcttctctgg   50640
gctgtaaagg ttgaattttc cagctaagca aggaagaaag acaatttcag gcaggaggaa   50700
gggcataagc aaagtgcaga gatgtgaagc tcaagagaaa tggatgggct gggcagaggt   50760
gtggctgcag catcagggga gaagaagtag tgcctggagt cagcaggcac ggcttgcaaa   50820
agcttcacct ataggtgaaa ggacaccatc tcttgcacca ataggctctg tgattggagg   50880
caactttgct gttttactgc cagaaaactg aggatgataa cccaaactgc agttcaagtg   50940
gcattcactg gtgtggctga atgggtgtt tgtggccaga atgtggtctg attggtcagt   51000
gcccagctct gttgattagc agatgttttg aatatagtag catccatgtg cccaagttgt   51060
tgggatgatt caacaagaaa ctttaagagc tcaagtgccc tgcagttgtc agccaggtga   51120
ttctcttcct ttggacccag ttagacgcag gcattacctc gtggctttgc cccagtgtga   51180
atctttgtcc tccaacttga tcttttttatt tgtttcatta ttgtatttaa gttgtttatt   51240
ttagagacag acatttttta acagctgtgc atttcctgtc cctttgtttt ccagtcgtca   51300
tgtgtttcct tactctctgt gggtgaacgt ttcagatgtc tgtttgcggt gcccagcgtg   51360
caagataaaa tttattgcag tgccttcggc ctctaactca ccattccaac caattcagat   51420
agcccaaggc tgttttatcc agtggatttt tccatgtagt gggaaataaa tcttgaatgt   51480
tactgtttag attagccagg aaactcattc tgggatgttt gcccacatcc attggcattt   51540
ctcaaaagga accccaggtg tctaccttga caccagcagg gccacttgag ccctccgctg   51600
gcattcatcg cccgctttgt tctcagcctg agtttaggag ttacagatgt gagaggcggg   51660
attatacagc caacatctct aagcgggcag tggctcccctt accctcgaag acctcactcc   51720
tagcacgtcc tggatgtatt cgtcaaaata tgtcctctta tgccacgtca gcacagggtt   51780
gctccccact ttgatcatca agtttaaaca aaaggaaaga ttttcttttct ttctctgcct   51840
ctactggaca tcatttccca cctaacagat aatttaatgt atctgttact gaatgtgttt   51900
gaattacaga cagagaggtc acagttaaag aaggaagcct gctgctactg cagcttgtcc   51960
tcccaaggag gtgtttgatt tagctgtgta aacaaatgac tgcattctcc agaggtcctg   52020
aacacagctg cctgcgctgg agagggctca aacctcttcc gccagggtga actctgcttc   52080
ctggtgagtg ccagcaaaac aaccaacaaa gagctgtagg acttgtgtgg acttcaaatg   52140
gtggtggtcc tgccacttgg gctcagccac agcagttagg aaactaaagg ggaggaggaa   52200
```

```
agcccttttcc ttgctttatt gtcattggct gtcatagggc attacaatgg ttctctttga    52260
gattctgagc tccggctata acatttgccc agaatctgcc tctgaggcct taagacactg    52320
tgttttattt cagcaaagat gcccttttgac tccttttccc actagtggtg ctaggtttga   52380
gcaccttaca ctggcccctt acaatagcca gttcttgtct acctacattc ttccctaaca    52440
ttcatgattg catagttact cttagtgtag aagcagacag cttttacaca tagactccat    52500
ggccgtagcc tcatagaacc tactatattc taacttgcaa gctaatcaga ccaaatatat    52560
caaaatcaaa aacctctgct gagagtttat tcattcatct ctgtctccca aacgtactta    52620
tgtacatacg tgcactaata tacatgtcca ttagccaaga ttttgatttc agggatcaaa    52680
gcaagtacca atagggaatg aggtcacttg ctgcatggca ggtggcttcc ccatgagaat    52740
gcaaggccac ctcatgactc atacttcaga gggtgaccca ggaacttctg attcatgtcc    52800
aaagcagctt ctacaattgc tctaccttga tctagggaag atgtggggag gatgacattc    52860
gggattagct ttataaggcc ttcctgtggg cagagttgtc tgactttcac ctagtgatca    52920
acaagcagct agcaagcatc agtgtgtgag gccccacgcc ctctcagctc ccctactgcc    52980
cacctgggac atgggctttg gcatctgtcc atagcattgt tctaaccaaa tgaggtgtta    53040
tggatcagct caggatggga tatgttccca gacatattat ttaaagaaaa tagctcccta    53100
cctcccctga taaacagctg ccatggctaa aaggtaacct ggctggggct taaaagtctg    53160
ttgactttca agatattttg caaaaacagt cataaaaatg gtatttatca gatcctaact    53220
atttgtgaga cggtttggta taccatagtg gttaaaaaca caggctcttt ccagaggagg    53280
tttactttgc ttagtcgtgt ctcctaagtg aacttggacc tcataaggtt gttgtgagaa    53340
tgaaatgggt gaatatgagt aaagtccttg gaccagtttt ggccgtatag taagccttca    53400
gcaagcatct gctttattc ctacagggag gcaattgtaa gcccttcaca aacagcgtct    53460
aatgtgatcc ttagaacaaa cctatgagat agggcatatc tcaattttgt aggtagggaa    53520
acagaagcca cacaattagg aaatggcaac agatctgtta gactcttaaa cactatgcta    53580
caccaatttg caaggcaagg aagacaaagc acctttgaaa atgggtcaga tgttttaggg    53640
taaatgaacg tttgagaatc ttttaagttt ttttccccc agagattatc aaggtatcat    53700
tgtaggggga tgcatcagga acatgactga tgaatcagct gcctgataaa ccagccagga    53760
tggagcccac gtcatcacag cagtcagcaa tgccactgaa aaacatcagc tgcttattcc    53820
cgtatagatt tcccttaag acatgaaaag ggagttcaaa gagaatgggc cagatatctc    53880
tgagagtcat attactaaaa tatatttatt tttactagct ttttttgtttt aagaggtata   53940 ctgtcattag cactgtagca aaaattcacg ttttattaat ttctcctagt ttatcatgtg    54000
attctagggt aggatgcaga gttatattca aaatacacaa atcaactcaa ctcagtaaac    54060
atatatcgag gccctatcat gacaaaatgc tattctagag accacggcga acaagccacg    54120
gccccagcct caaagaatgt actatctttg gaactgtgct ggccaataca gtaaccagca    54180
gccacgcagg gctatttaaa tttaaattaa ttaaaagtaa aaacacaatg cctcagatgc    54240
attagccaca ttttaagtgt tcaatagata tttgtggctc ctgcctgcca tattggacag    54300
ggcagatata gaacaattcc atcactgcag aaagttctac tgaacaatgc tgctctggag    54360
cagaagatct tcttgttcag ggatgttaca cccccgcttg tggctagagt gtggcttatc    54420
ctcagagcaa ggatagggga accatggcac tctgcaggct cagcactgaa gacacggatg    54480
caggctctgc ttctgaccta gattgacctt gggcaaggcc ctttgctcct ctgatcccaa    54540
tttcttcacc agccaagtaa gaacatcaga ccacaagccc tctagggctc tgtccaaatg    54600
```

```
ccccatgact gagtgaactg gtagaacatt ctatgtgtgt gtcacaacat gaagagcaaa    54660
gactttcatc tccccaaata attttgtttt tcgttttagg aattaaattt cagattcact    54720
ctaattgcca atactaaaat tctctatatg cagttctaaa cttgacaaac caataaaaaa    54780
agattatttg actacttatc tttgtacaac attgaggtct ccctaaagca aatttaaatg    54840
catattttaa aaatgtattc tagcagttca gttcagaagc cccctggccc aagcatcaca    54900
ctgtcaatcc tttgtcctca agcagcatgg ttgggtgggt taagtactga caaacactgg    54960
gtgtcaggcc catggtcagg gactgtgcta acagtctaca tattagatgc cacctacccc    55020
caccctcaac agacccaaac tatttatcca atagcaaacc ttgcattatt tctgtccaga    55080
agaaacaaac atttattgac aacttttggt gtgtgacctg tttaagtcct acatctcatt    55140
taaggactgg tcaatgttag gctaggcaat gcctgtttgt gagagaatca ctgcctaaag    55200
aaaattctcc atttccctta gctctatggt gggtgactac acatactggt atttcttaaa    55260
gaaataccaa ttccatttcc ttttaacata attattaata tctcattagc atggtgtcac    55320
tgaagcctgg gcccaaagaa ataccaattc catatcattt taagatcatt attaatatct    55380
catcagcgtg gtgtcactta agcctgggcc ctttagaatt tttcatgtac ctgtgttcct    55440
ctgcccatat cagctggaac actaatagtt ttcttccttt ttatctagaa gactgagaac    55500
attacatggg acctgcccc aggggcatgga ggctgaggtg ggacagttta gttcaggagg    55560
cccaagaagt gttgggtgtg cagccccttg ttcaaacaca gcctctgaat cgccagaggc    55620
ttccggtgca tactctgagg cgcaggtggg actcggagt gagaggtttc ggcgaatgaa    55680
ttgggattgc ctacttcttc ccagtgcagt ggagcttggt tctgtggtca ggtccttacg    55740
ccctgtctgc ctttctcgtt tctttatttc tcgggtagta gttgtggaat caaatgacct    55800
ggggtttgat acctactcta ccacgcctct gggggagtca ctcagactcg ttgaacctaa    55860
gttccggggc tgccaagtga ggataagtag taattgctga tccacctact tgacaagata    55920
gtagtgaggg ccctgagcgc caggctgtgg atccagcctt tcccacggtt cctggtgtgg    55980
caggaagaac tctaggcctg aaggtgaaat tggggaggga gtcccagctc tgccactgtc    56040
tctctgggtg acctcaggca ggtctcctca aaaaaataag atactttata aagctcagtt    56100
tcctcttcag taaaatgagg attccaggta actcacagat agtttgtggg gatgaatctg    56160
ttccttaaag cctgcagtac atcaataacc cagtcttcct gcttgctttc cccctctcc    56220 actaccagtg atcatagtct gatcccatag gtgatatccc agctcaaaac cctacattag    56280
cttctgtggc tgtttaaggc ctgcccagaa ctcccctggt cttagcactg aaagcacgtg    56340
tccggggaag ccctgcattg gtcgttcata ctactgagtc ccgcagggca aaccgtccgg    56400 tcccacccctc ctttctagtg ctgctgtcac actcacctcc cttcacccta cactccttc    56460 tgtgccttgc aattacctag ggagtttttt acaagatatg gatgccctgg ccctgccact    56520
agagattctg atttaattgc ttggggtagg gcctggcata ggtatctttt aaagctccgc    56580
agtggttcta aagcacagcc acagatggga accactgatc tattcttgta ggtccccaga    56640
tacctcatgt gctgttccct gtgcctgagc tgacctttcc cccactttcc tctcctcggc    56700
taattcctgc ttatcctcct actcaggagg ctcttcctcc aggcagcctt ccctgatccc    56760
tccaggaaga cttagctgcg tccctccgct gggcttcccc aatacactgg gcttgctttc    56820
attagaacct gatccttcca cattatggtt gttggtttgc tccaatcctc ccctcatta    56880 gctctcaact ttcttttcagg aagagatgtt tatctttcct tcttgtattc ctagagtcga    56940
```

```
ccaggctctg gcacattgca gattctcagt atgcattcag ggaacaactt aatcaagaca    57000
agaccatctg acttcttgtg agttacatgc taagaaagaa atgtcgacac caatagccct    57060
cacaatgata ggaacaggag gttaaagaaa aggaaataga tgcaaatagc aatataagtg    57120
ctttaacaaa tctatacagg aggacaacca tcatattcaa attttcaaac attcttagtt    57180
ctgctctttt gtgggtaatg gttttttttt ttcctcttcc aggagaagaa aagaggcata    57240
ttatagaaat tcctcctccc ccagcattac ttgtcacaga attgtaattg gaagtgattt    57300
ccctgactaa gttatttggg ctgtctgtta ttttctctct tcctccttgc tcttccctca    57360
gctggccatc ctgtgtgttt ggagagagcc agaaaggttc aaggctagga atgtttctct    57420 ctctcttaa agctctttaa tcgtcaggct ttctgatctt caaagcaggc tgtagccagt    57480
gtgaccccac tccctcgcct ccccatgctg gagagtaaaa gcctggagta ttttgtcat    57540 tttgaagact tgcatatttg gacagccttg gacatctgga aagtgtggtc ctcactagct    57600
ctgcagggat aagagcacgt cagcacttcc aagctctctg gcgcccctac atctggacac    57660
gttgaaaaat taacaccaga ctctggagtt aagcaaacat taagtttata ggcctccttg    57720
catttgacca tttcctggga cagcagccct tatcctgtga cttctgtgt gtagagttga    57780 gtctttgcag ttggtcctcc tcacactctc tcaactttgt gactctctgc agtgcttggt    57840
cctggataag tttgaaagct acaatgatga aactcagctc acccaacgtg ccctctctct    57900
actggaggaa aacatgttct gggccggagt ggtattccct gacatgtatc cctggaccag    57960
ctctctacca ccccacgtga agtataagat ccgaatggac atagacgtgg tggagaaaac    58020
caataagatt aaagacaggt gatgtttcag gaagggctcg ctgcatttct ccaaagtcag    58080
tgggaaatta catttggtag agagaaaggg attgagactg gactcataaa tcaataaaat    58140
taagttaaat aagaaaaaat aagatatttt ataaagctca acaaagagtc cttgaatgaa    58200
agcaattaca gagtcacatt gtggctaata ttcaaaactg agatttaaac tgaggactag    58260
gaaatagaat tggatccttt tgaagcgttt aggagaaaga ttttaagaga atgagttccg    58320
agtcaccctg tggtcgggag gtgtgagtga gctatccaag cccgttccca tcctttgtcc    58380
ctctgtgtct tctcaggtat tgggattctg gtcccgagc tgatcccgtg gaagatttcc    58440
ggtacatctg gggcgggttt gcctatctgc aggacatggt tgaacagggg atcacaagga    58500
gccaggtgca ggcggaggct ccagttggaa tctacctcca gcagatgccc tacccctgct    58560
tcgtggacga ttcgtgagtc tgaagttcgc gatcctcctc catgacacgc taatgggggt    58620
gctggagtgg gctggggtgg gctggggtg ccctcaaggc ttccatgtct ttagagagag    58680
ccccagggac cagagccaaa ttggagagca tggagctctg actgaggaac ctgcttctcc    58740
caagctccag gcaggcacag atgagtcagt gcagtggtgg gaaagggaaa agagttgatg    58800
ttgtagctgg aaaagggaag gggaaaatta agcaaggaa agtgaggctg ggggagggga    58860
caaattcccc actatgtagt atgtttggta tgtggaaggg ttctggtcag aatgtttgcc    58920
caatgattgc cacatcagca ttcattttgg actctgtatg gccagtaggt ctggttcctg    58980
ggagccctgg aataatgcag ccccttccct aactaacatt tccatgatgt atgctcaatg    59040
acaaggcaga ggaatgtgtt ggatgagctc aggacctgcc tccctggaca ctcccatccc    59100
aggcctgtat atctgttgac caggaataag ccaagcaagc agcctactgt ttgactgaat    59160
atggatttgg ggggtggtag agaaagggcc ggggtggagg gttgggaggc tcatttgtca    59220
ttatagatgg ggtcagacac actaccaaaa cagcagcaga gatctacaat tgagttcacc    59280
taaaactcag tgtggacaca ggaaaccctc ttttaataac tgtccaatgg gttttccagc    59340
```

```
ctcagctcta cagaaaactt gagataacag tggccagtct gcagttagtt tgggttcgga    59400
caataggcag agctgggaaa tggagccagg ggcgaaagcc caggtccact ttaggatcag    59460
gacgggagtg gctggtgggg aagtgaggtg ggtgtgggga ggcaataggg agctgggtca    59520
tttggtatgg gagagtcctc tggtggctag tcccagaagt gcatgcttta cgaacatatg    59580
cttctctccc tagggccacc ttgagtgaaa ccctcccatg ctggaattgg gcccttcag     59640 tgacaacaca caacagtttt caatagataa taatcccaag ggctttacta gcacatgaaa    59700
cacagggaaa acgtgtaaag ttcacaagaa agtcgttcca gtgtatcaaa tctatcctgt    59760
ttgccaggtg gatataccag ggtctcctcc acctgtgcat ggctggtggt gggtccagtg    59820
gctgttggat aactgatgta ttgatggatc attcgccttc tgaaagtgcc aaactgatta    59880
gttattttgt gtgtctttt gtgtaactag ggtttgacct tccagggcag actgtgctgg     59940
ggcggctgac cccttgggga gccaagttat tgctcttacc accaccactt gcccttgtca    60000
gtcctccacc ctcttgggtt tcagtgtcag catgtagctg tctactcaga tcccatccac    60060
atcatcaagt ctgcagtttt ttccttgcaa ggccttacag ggaagatctt tgacatagag    60120
gatataattt tattgacaca ttttacttgc agagcattca cccgggctaa ccagaaagcc    60180
agcactctgc tataaacaaa aaataatgct tcagggctaa catggaatgt gttaaaagat    60240
tccagcccat taaatgtcca ggggaggttt tcctgttttc ctttccctcc atctgggctt    60300
tgttctcaac acattcattc aacaaacatt tattctgcct ctaccaggta cagagcactc    60360
tactattctg cttctctcct tttgctttag tttcatgatc atcctgaacc gctgtttccc    60420
tatcttcatg gtgctggcat ggatctactc tgtctccatg actgtgaaga gcatcgtctt    60480
ggagaaggag ttgcgactga aggagacctt gaaaaatcag ggtgtctcca atgcagtgat    60540
ttggtgtacc tggttcctgg acagcttctc catcatgtcg atgagcatct tcctcctgac    60600
gatattcatc atggtaagcc aaatggagaa ggcccagaaa atcttgaata ctttggttcc    60660 tttcccttt cctcctgttc atgtgcctgg attagtcatg tggccaccaa ggagagcgtg     60720
acatctagct tcccagccct ccttttagc caacgtggga gacactcaaa gagacgaaat     60780
ctcctgaagg agccactgta tcacagcatc ctcccatctc ccacttcctg cccagggtc     60840 catggtccac acagacttcc cagtcccatt ccgtgaccat ctggagaagc tgctattagc    60900
agagccctgc acagggtgat agtgtaatta aagtggtctt ctctttccaa acacagaaaa    60960
aatcagttca gggagtgttt tcctgggctt acaattttaa ctactggcta gagttgaaat    61020
ggggaaagcc ttttgccttt tcagtagcag taggggagga gatctggatt atttacttat    61080
catcatcatg gtcacctcct acatggcttc accaaaaaac attctgctgc ctgaaaaagc    61140
tccaacacct ctctctcttt taaaggatgg aatttggagt ccatccttcc tcagtgataa    61200
ggagttttta tagccacagg cagcatctat tggtctgtcc tctgcaaact tgcaactcct    61260
ctgagagcta gacttggaaa tgaaacatta ttttgcaatg cgctgctatc cttcattttt    61320
agctcctcca ccgtagatga tagtttgtac ttgttaaatg ataaggatat aaatttaggt    61380 catttttat atttattgg gtggaatttg gtataatttt tagacttcag gctttacagg     61440
ctcctgagat ggactgattg agcttgttct acttcttccc catcatgata ggaagtgctg    61500
taccacacta ggcagtgtgt gtagtgacca cagactggct gagtgtctcc catcccatgc    61560
tggcccatat ctggtaccca cctgatccac aaatgttcca tcagatcctg ttcaaacaac    61620
acatctccag ttaagccaaa tcttgccctt tctccttacg gtaaaatgta ctaaatctga    61680
```

```
aggttttgtc tttttaatgt tgctccatga tccagtgatc tgtggccttg gttatgctct    61740
gtgctagagt cctaacaaga caaatgctaa ggtagaggtc attctgctca acaacctga     61800 ccccacctgg atgtgggctt acatttgcaa agggcaccaa agttctaaga gatgagggga    61860
ggagctgagc cccttgtcct tatctaggtt tcccttgttc tttcccatcc ctcagtctgc    61920
ttctttcccc agtaccaaca tgtttgtgtc ctcagaatta aaggagtaaa aatgtgtaaa    61980
catctgacta gcaacagcca tgagattttg cctggcttgt tgataagcag cattgagatc    62040
tgccctccta agaatgggcc attaggtctt caaagctttt acgatgtgag gtaaagaatg    62100
ttcaccagga gtttcatgca caaagggtt tctctttgtg ggaactagaa cattgttcca     62160
gtgatgacgg aaacagggct ttccatacca aaacagggtt ttcctttgaa tgactctccc    62220
acctttccct tgtctcttcc tccccacctc aacaacacag gaaagaagct ggaagcaggg    62280
acaatgggaa ggtcccttg ttactcgagc tattagaaac aaaaagaaaa gtggccatct     62340
gaggaagcca cagctggtga aactgtaggg tcacagagtg aattcacct ctggcttaag     62400 tcagtgaaaa gtcctagaag tttgtggtcc tagaagtcct aaaagtttat gggactttgt    62460
tttgagcaag gataagaaat tgatttcagg ctgggcgtgg tggctcacgc ctgtaaccct    62520
aatactttgg gagacagagg caggtggatc acttcaggtc aggagttcca gagcagtctg    62580
gccaacatgg cgaaaccctg cctctcctaa aaatacaaaa attagccagg tgcggtggca    62640
catgcctgta gtcccggcta ctcaggagac tgagcaagga gaatcccttg aacccaggag    62700
gtggaggtct cagtgagctg atatcatatc actgcactct agcctgggca acagagcaag    62760
actctgtcta aaaaaataaa taataaaaa agaaattgat ttcattcttc tgagaactgc     62820
aacaactacc ttaaagtgat tccatccaaa acccacatgt tcagccatgg acttgctttt    62880
atggagctgc gtgtgggtga cacacaaaat caggagctct gagtcctaat ttagacttt      62940 atttagattt cctcaaattt gggttccagt taagcgtggg tctcttctgt gccccgctcc    63000
cctttgccat ttgttttatc tgttcttcag tctgttctgt cagtacccac aggcaggaga    63060
gcagaaagga gaaatggcag ccacagcaga caaatggcac attcgttcca ctcagctctc    63120
gcatgcccat cacagataca gctcattggt ctcttttcta tgagaggaag ccagagctcc    63180
agggaactac tgccaactga tcagaactca tttaggacat ggacctattt gttcctttat    63240
gttcctggga agagcacagg atgaattcta tgtactcatt tacgtgttca gagagtaaag    63300
tgcctcatag gatgcctcca gcaaaagata accaagaagg tctaatacct ttgacaatct    63360
cagtttatcc tatagtgtaa ttggatagca gttcccctag caaaagttgc tagtttggtc    63420
ctatttccta catagccaaa gtgattgatt cattggttaa tgtgaaagtt actgagtact    63480
gccagcaggt tctaggaaat atatttgtgt gatattcatg gatggggagg atcaatccac    63540
ttccaagtga tttggattaa ttactggtat tttcacctgt gtgggtagca aacctcagaa    63600
aatcaagtat agatgacggc ataggacagg ccaggcccca ggcaaaatgt tgaagctcct    63660
ctggagttcc ctcccatctc cctctttgt tttccatata cctggtttat ccagggccct     63720
ggagatgctc caagaccccc tacccaggtc ttcctcccctt gtcccagcta tatttctcca   63780
tattaccact cttctcaccg aggatttgct tacttaacac ataataaata ctattaaaag    63840
agaaacttag gcacattaaa atgttagagt tgattccagc aaacagtgat tcacaggagg    63900
ctccagatca caagtggttc agggccccac tgaggggtag ggaagcaaga caaagaaaaa    63960
caaagcaaat atttgattgg ttcaagtgga aagtccctga ttacaggtta gtgggcagtt    64020
tgtgattagt taagtttctc taagttgggt tttggtttgc tgatgtagga acacagaatg    64080
```

```
ctggggccgt tcaacctaa tggtctccca attaattttt ttaacattac tgatgactgt    64140
taggagtcta atgtgctact cctcccaggg aaaatggcat tcctaggatt aaaggaactc    64200
agcacatgga gtgtgcgtag aaatttagac actaactgca ggctggtggg agagagccct    64260
ttagggcaga atgagaaggc gtccggccaa gggcaggagt tactgacgca tggcctcttg    64320
gtttcagcat ggaagaatcc tacattacag cgacccattc atcctcttcc tgttcttgtt    64380
ggctttctcc actgccacca tcatgctgtg ctttctgctc agcaccttct tctccaaggc    64440
cagtctggca gcagcctgta gtggtgtcat ctatttcacc ctctacctgc cacacatcct    64500
gtgcttcgcc tggcaggacc gcatgaccgc tgagctgaag aaggctgtgg tgaggccctt    64560
gggctggccc ctgtcctaca acacgtttcc ttggaagggt ccgtagcagt cctggaggcc    64620
cagcctgccc tctgagggg tccactttgc ctttgaccta aggttaaaaa gttcacgtga    64680
ggctaaaatg tacaggggca aaagtgggag cagtcctcac cccgagcgat gcaacagtga    64740
ctcctcacca cgcctgcttg attcatctgc cctggaaagt cattaaaaaa ccagttcaac    64800
tcatgggtcc ctttatttac tcacaagaga gagccagcag cccatttcac tagttttcct    64860
ttcctactct tgagaagaa tcagaaggga gggagcttgc cactttacta tctgtctaaa    64920
gagatgtttc cattaattaa aggttttgt tttgcttcaa aaaaacttga attggagtat    64980
ttccacaagt atcttaaca tgctctacca atgtttgcag aaagaagtgc agaaatgaga    65040
ctgtccacag agtcaggctc gctggccagg agaggactcc cgaagctgac ttctgatggc    65100
ctgagaaact tcctagttca caattccag acccagacaa agagcactgt cttttctcta    65160
attgtttca aatgggccat ttccaccctc taatcagcct ctggccctgg agggtgcagt    65220
tccccttgtc ctccggagtc tccctgtctc tgtgctgtag agtcaagaag ggacaaccac    65280
ctgccctcac tgggaaaga cagaaagtct gacttgttct cacgactcac acttattagg    65340
ctccagaggt gtcagggcat ctgccttca tttcttaggt taaataagaa atcaattgct    65400
gccattgta gtacccaatt ttctaaaatg atcacaatgg ataagtggca agaaatcctt    65460
atgactcatc tgtgggcaga gttgggctat tttggtaatc cttgagtagg cagatggaat    65520
ttgaggccat cttcttgggt acatagatca ctaggaagct ataggtctag caactgtgga    65580
ttagggctgg gctgagaatt gtttcatgtt ttttgtgact gtatagctag agactctctt    65640
gtttgcagag agacactctg aactccccct ggccgtcaag ggaaagactg ccttcaccct    65700
cctgagctga ccttacactg agagacaatg gggaccctct tttggccctc ccctctacct    65760
cgagggcatc tgggtgctgt tgcattggat aaaaggcact gctctttttc tgtgccctc    65820
ccgcctcact gcagagctta ctgtctccgg tggcatttgg atttggcact gagtacctgg    65880
ttcgctttga agagcaaggc ctgggctgc agtggagcaa catcgggaac agtcccacgg    65940
aaggggacga attcagcttc ctgctgtcca tgcagatgat gctccttgat gctgctgtct    66000
atggcttact cgcttggtac cttgatcagg tgtttccagg taagcatcct cctctatagg    66060
gtaaaggtaa ttgagttctt cagatcccca gccctctcca ttcatctagt ttaaatttca    66120
tttcttccaa gctctttgtc agaaccagca tttgaagttt aaatctagaa gttaaaaatc    66180
caccagcaaa tcctactggc tctacttgag aaacaaatcc agaatctgat ctcttgtcac    66240
cacctccacc acaaccttcc caatgccagt ctcttccttc cactaccacc tcccatcagt    66300
ccattctgca cactgtattc agggagatcc tttcagaatc aaggtcatgt ggtgtcagcc    66360
ctctctgtca aatgcttgca ctggcttttc ctctctttca gagtaaaacc cagtgtctca    66420
```

| | | | | | |
|---|---|---|---|---|---|
| accctggcct | ccaagctgct | tcattatccg | gcctccaact | ctcttcttca | tcttacgatt 66480 |
| ttccctactc | ctccatgttc | ctctgctcca | gccacgtcgg | cctccttact | gactgtttaa 66540 |
| tacaccgagc | gcatttcctc | ttcagggcct | ttccacctgc | tgttctcatg | ccagaagcac 66600 |
| atttctctcc | ccacaacctg | caacccgccc | ctcatatctg | caggcttgct | tccttacttt 66660 |
| gttaaggtct | ctgttcaaat | gtcccattat | cacagggatc | tttccagact | gaagagatct 66720 |
| acataactat | ggctctgtaa | acaacattcc | tccagggttc | ctgtcccctt | acccttacttt 66780 |
| attttgggga | acattcttca | ccatctgata | caatgatgta | tcttatgcat | gtatttactg 66840 |
| actctctgcc | cttagtagaa | tatgagccca | gagagcatgc | atgtggtcta | ttttgttaac 66900 |
| tgtgacagtc | ccagtgccca | gaatagtgcc | tgaccttgg | tgggcactga | ataaatatct 66960 |
| aagtaatctg | tagcatggaa | atcagcttc | tgaaaattgg | ctgtttgcac | ggtcgtgtat 67020 |
| ttgcttggta | gaaaatcaaa | ttttccttca | aattagcatt | ttctggtaac | tagagctgcc 67080 |
| ccatcttcct | ctgagtggtc | tccaagtcag | ccaatagcct | tgtgctgtgg | cagccatgcc 67140 |
| tggctcttga | tgctgtagcc | aaaagcaggc | agggatggt | gaggctggtc | cagtccatgg 67200 |
| ggagggacaa | actcacagct | ctcagatcat | ctcagggcag | cctttgttgg | cagaaatagg 67260 |
| taggcagcca | ccctgaatag | gaggaaggct | tctagactgg | gtcaggaggc | ctgggtttgc 67320 |
| atcctagtgg | caagcgtgca | ttcatttact | agggctgcca | taacaaaata | ccactaactg 67380 |
| ggcagcttag | acaacagcca | tttatatctc | acagctctga | aggctggaag | tccaaaatca 67440 |
| aggtgttggc | agggccatgc | tccctctgaa | acctgtaggt | gcttgggcac | tccttgactt 67500 |
| gtagatgctt | cctgctgatc | cttcgtctgc | acatggcatt | ctgcctgtct | tacatggcca 67560 |
| tcttataagg | ataccaactg | gattggatta | ggtgcctacc | ttgctcccat | gtgacctcat 67620 |
| ctcaactaat | cacatctgca | atgacccgtgt | tcctaaacaa | ggccacatta | tgaggtacct 67680 |
| ggggttagca | ctctggtatc | ttttttcttg | acagcacttc | tgacaccaaa | tgtgtgtttt 67740 |
| ggttttttgt | tgttgttgtt | ttggcaccaa | ccaattctcc | tatattaatg | ggttgtccaa 67800 |
| gaattcaatt | gaattctgac | actatccaga | attcacacag | actccacggg | ttcagtccca 67860 |
| caaggcttcc | ccgtcttcag | atgccagctg | gaaatgtggt | gcccaggcta | cccacacttt 67920 |
| tgccaaaatc | ctgtacttac | aatcacagct | ttaaaatgaa | ggatgcagct | caggaactgc 67980 |
| cacatgaag | agaagcacag | tatggggtcg | ggggaagagt | ttctatgctc | tctctagacg 68040 |
| caccactctc | ccagcacctc | aaagtgttca | gcaacccaaa | agctctccaa | atcttgttgt 68100 |
| tcgagagttt | ttataaccct | atctccagct | ccatactccc | ccattggagg | ttgagggttg 68160 |
| ggactgaaag | ttccattctt | cacatgtgtg | gtgtttctgg | tgaccagtcc | ccagaaactg 68220 |
| cagctatctt | ggggctctac | cctgagtcac | atcattagca | taaactcaga | gtggtagag 68280 |
| gaagggcttt | attatgaata | aaaaagaca | ctcctttctg | ccaggaaatt | ccaagggttt 68340 |
| taggagatct | gtgccctgca | caggagctgg | ggacaaagac | caagtatatt | ttgtgttatg 68400 |
| ccacagaccc | caacatgtct | ttttggaggg | agaccaaatt | caacccatga | cagtgacttt 68460 |
| gaacaagaca | tttgaactta | gtctgttttt | tctatcctac | tagattgttg | gaaacagata 68520 |
| taatagatga | aaattagttg | attaaaaattg | aaatttgtgc | ataattcaaa | agttttattt 68580 |
| tagccaagct | aaagctttca | tttattcaac | agctatttac | tgagcagcac | ctgtgcatga 68640 |
| ggctcagcag | ggccaggttc | tgggaacaga | gcggtggaga | taaagatcca | gacctgcccc 68700 |
| gaggaataga | cagtccagtg | gcagcaaagg | ccatgaaaca | tacggcaact | cttaaaaaaa 68760 |
| gccgagacca | tgattttaca | aaatcaacat | tttgtaggga | gcagaacttt | caaagagaac 68820 |

```
tggactagaa atttgggagt ctttttcttg gaaccctggt agatccagta gaatgaggga    68880
tgggggtgta gggttaaaaa cactgacatt agaactggat tacctgtgtt ggaattccta    68940
catttctgtt tcactatctg tgacgggggg cagatggctg aatctcagtg tgcctctgtt    69000
tcctttctca caagaataat attactacct atctcctggg gttgttttga ggtttagatt    69060
atttaacaca tggaaagcac tcacagcaat gcctgccaca gaaagaatat ccagtacatc    69120
ttagtgatga tcaccattat tattatctga ctcctggaaa aggacttgat ttaattctct    69180
catgaaacgt tttcttggaa aactgatgtc aaccaagatt attggtcttg ctgttgctta    69240
taacacccca aaaacatgac tgtgtggata aaaatatgtt ggaaggggta gtctttctgg    69300
gagcctgaga atagccatgt aataataact gcaaatatct atagttacaa tttgaggttc    69360
aggtaaataa actctagatc ttatagaact gcggtaaggt aggataggga gactccttcg    69420
actttctctg tttatttgtc tctattttta ggagactatg gaaccccact tccttggtac    69480
tttcttctac aagagtcgta ttggcttggc ggtgaaggtg agtcctttaa aacacaaatc    69540
ttaatgtttg aaatcaactc cttgggctct gtgcaagatg tatatggatc acagaggtgg    69600
ccctctatgt aaacggtgtg attcctgatg agtcagctgc ctcctggggc tctgcccctt    69660
gatgggcatt gcagcgtctg ggggaccacc tttcacaagt tgctgggccc tgtgtgatca    69720
tgaatggctg atcatggatg aagccctggg tcctgtacac cttgtccagt agactaaatt    69780
gccctattta aaaaaggcca agccacttca gggttcaaag aacttttgca gcttttcagt    69840
ataaagcaga aatccaggga atcatgaagg aacctttgca ttcatctccc attgccttcc    69900
ttgtgccttt ttattcttct ctgccttttc aaaatataaa ttagtttatt ctcccaagat    69960
gaagactcct cctggggctg aggcagagct gttatcttca gggcaatacc tcagattctc    70020
ctggtgttga tctttcttag gggtggggaa aaaggctgaa agggcatttg cccacaacac    70080
atcttaggta aaaggcacct ttactactga accaaacagg aggcctagct agagaaagtt    70140
ctagaagcag ggaaaagcac agactctttt gtgaggtctg agaaagcaaa gaaattccag    70200
ggtgaaagcg ggggactccc ctagagctga agtactctcc catctgtttg ttgctcacct    70260
acctattctt tactttgtat tattgggcct gggccaggac ttatcctgca agcactgaga    70320
tggatgtttg ttttctctgg gggattagtc tttttttttc tttttttctt ttgtttttg     70380
cttttgtttt cactgggtca aacaaacaac actttaacag ctcaggattt tttcattgta    70440
ttgacttgtc tacctgtaaa cttgttaatt ttttactata ataaaattat catataataa    70500
atgaaaaatt tcaacacagg gcttgtgggc attttatttt tctctacaat cccaacagat    70560
actctgcctc ttaagaaaaa aagaaatcat aaggaaaata tgctccttca aaagtgaatc    70620
acaaatatgt ttgccaacgg aaggcaaata ttttcacct gtctcatagg ctggactgaa     70680
atggatttct aaaactctct aaaccagaa aagagctgag tgtctccacc caacctccct     70740
cctttcacag attaaaaaat aaaaaatgga gcccaggaga catccagtat cttcccctat    70800
tggtcacctg ggacaaaatc tggaacatgc acatgcattg cctggcagga actcattcca    70860
gtgattaaac tcttcaggag gatgtttcct cttgctattt cattacctat ttgtgcagtt    70920
tgatagctag taaagtgatc aaaggaactg tggggcatag attcaaaagt ccttcaggaa    70980
gcagaaatag aagaacagta ctagaggcag caggtccctg accagcaggc ccactacctg    71040
ctgctccagc acacatcctg cacattttca gagggtgggg gacagagggg ccctgggtgg    71100
ctgttgcatt gagaaatctc gccctgctcc tgtatgtgca cttgaggccg agagcccttg    71160
```

```
gatgcctggt gacagtggtt tcctcctgcc cctgccttcc tctctggcag actgactggc    71220
ccttctgctc ctcttcccct tccaggatgt cctgatatct tttaaacca aatgccaagt    71280 ttgccaaaaa gtgtctgttt gtgtgtgtgt gtgtgtgtgt gttcaatgcg tgtgtttata    71340
ccacacttca caatttgtcc aggcttgtat aataccatc accaggctca accctggtgt    71400
taattccaag atacttaaat gcccatctag gtgaatttct caggtaaacc atatattcaa    71460
gctgtagttt aagctggctg cccgtcatag cactttgaat agactttgtt tttgtttttg    71520 tttttttgaga cagagtctca ctctgtcggc caggctggag tgcagtggca ctatctcggc    71580
tcactgcaac ctccgcctcc cgggttcaag cgattctcct gcctcagcct cctaagtagc    71640
tgggattaca ggtgagcgcc accccacccg gctaattttt gtatttttag tagatacggg    71700
gtttcaccat gttggtcaga ctggtctcga actcctgacc tcatgatacg cctacattgg    71760
cctcccaaag tgctgggatt acaggcgtga gccaccacat ccggcccctg aatagacttt    71820
tactcaaggt tcaccatgac tttcacatgt tttgtattgg agtaaaatgt gccagtggtg    71880
ggctaaagaa aattaactca tttcaaattc aaacctggtt tcttaatttt ttttaaaatc    71940
acagtttctg aaactgtggg ctcctcatgg cacattgaga ggaggaggtg aaactctcca    72000
agtctgaagc tcctgttata aatcttcctc tggcaaagat tgtgtgatca ggcttgagta    72060
cctcacagtc ctagagcagg tcaaaggctg gctaggaaac tcatttgctc cctgtacctc    72120
tcccctcctt tcctgccttt gctcgttctc agctcccggt ggtagagtaa cactggcttc    72180
tgattggtgc agggtgttca accagagaag aaagagccct ggaaaagacc gagcccctaa    72240
cagaggaaac ggaggatcca gagcacccag aaggaataca cggtaaaacc ccgataaaga    72300
atacacagca gaggcgagga aaaggctcta agcactgcag agggccagag caaaacatct    72360
catggcaagg gtgaaagaa gcctaggaaa ctgactctct ctgtggacaa gtgttaaacc    72420
agatcccttc tcagaggtcc atctgcatgt gtgtggaatg aatggttcag cccagacatt    72480
agcgcatatt tcctggagaa agcaaatacc aactatgtag tgtgcctgtg cccttgttag    72540
gcaaatccca agtgagttgc acaaatgtgc tgacttccga ggatttagca agaacaataa    72600
ctttggtcac tgggacttaa agcggatatg agctataagg aaagacaaaa ataaatgctt    72660
ctgtgtccag ggggaaagag actccagggg agctgactac acttcactta cggcttacaa    72720
atctagaagg ccattcattg aaaccatcag aagcctttcc tgacagtgga agttacctaa    72780
taatccctaa actgacgacc cagatttaca agttttgttt tcctggcttt tgctgccctc    72840
atcttctctc ttaaactagt tctgtatttc tcccaaggct tttcattccc taagcatacg    72900
catttctctg tggccaaaat gctctgggtt tagacaggca gcacagcccc tgggctctgc    72960
ctgacagggc aggagagggt ctggccttta tccctccagc ccaccccagg gccatttca    73020 taaaactaaa gccagagacc tgcagcccct cccagagtta gactgcagta caccatgcct    73080
ctggcaagat cctcctccca cagtggaaag tctaagccaa atcaggaggc tggggactgg    73140
ttccacctca gttgcaggca aggccaggag gcacggatag aagaaacagt ggactttttc    73200
cccctaggga aagaaatgct tagagctaca gtattaagat gacaaattaa gctgtgccat    73260
atagggtgaa atgaagcagg gatagatggg aggtcaggga gaagtgagag cactcggtga    73320
gggtctgcac tggagggggc atgggaggaa gaaggagggg agtgggggttt gagggatggt    73380 gatgaggaag cgtggactgc cctacccacc tattggaaaa cctgggagtt ctgaggagca    73440
agaagccttg tcaaagtca actcaaagat tcaagccaag gtgactaaga aatggcggt    73500 ccagaaaagg tcatgggaga atctgaaggc agatgttgtt ttgggaagat gaagaaccta    73560
```

```
agccgcttcc agaaattcat gaggaaatgc cccgtggact gttggcaatg agggcctagg    73620
accaaggttg agcttggggc caactctccc tatagacagt gagtgcattc tgacaagcat    73680
gggctctggg ttcaaatccc aactctgcca ctcatgccta tgtgtcctta ataggacgct    73740
tgatgtctct gtgtctaagg tttcctggac tatggaaatg agcctaataa atgtctaccc    73800
cttaggacca ttgtaagagt acattgaggt aatttgtgta aagcagtcga agcagtgcct    73860
ggcatatagg aggtgctgta taaacgtttg atgctagtat tactattatt attctggagt    73920
cttccttgca acggtgatag ccgaagccac aggggcaggt gacgttatag gcagaataca    73980
agggcctgga gacagagccc tggggccatg taattaggca ttatgtttac atcatgttca    74040 tttttttttcc tccaagactc cttctttgaa cgtgagcatc cagggtgggt tcctggggta    74100
tgcgtgaaga atctggtaaa gattttgag ccctgtggcc ggccagctgt ggaccgtctg    74160
aacatcacct tctacgagaa ccagatcacc gcattcctgg ccacaatgg agctgggaaa    74220 accaccacct tgtgagtctt ccagcagaga agctggctgc catgctagcc tgtcatttcc    74280
tggcttagtc tttccctatc agcggctgtc tactcttttcc cacaaatttt agtgacaaat    74340
atttgcggcc ccaaaaatgt gtaaaagctt tctgcagtat tcaaagatca ctaatatgta    74400
ttctcttgat ggggaggtag aatacgttta ttgccccttt tgtgtgccgg ggaagtggac    74460
attcattcag agagttgaag tgactttcct gaagccacca agttgtcatg gctcagcggg    74520
ggcaaaagcc aggcaccaca gttgcctctt gtttctcaca ccttgagtct ttccccccat    74580
ctcaacagtc catggtggtg atcaagtcat ggccactgtc atcatgtgca tggaagctat    74640
agagtcctcc tatttccttt ctcttttctt ttctttttttt ttttttttt ttttgagata    74700 gtaaccatta cccatgctgg agggcagtgg tgcgatcttg gctcactgca acctccgcct    74760
cccaggatca agcgattctc ccacctcagc ctcccaagta ggtgggacta caggtgcata    74820
ccaccatgcc cagctaattt ttgtattttt tttttttttt tttttttta gtacagacag    74880 ggtttcacca tgttggccag gctggtctcg aactcctgac ctcaggtgat ctgcccgcct    74940
cagcttccca aagtgctggg attacaggcg tgagcgaccg caccaggccg agtcctgcta    75000
ttttcaagga acattccttt tcctaccaat cattaggcag gcttcaacat cagctgatga    75060
gggttagtgg tcgttctgga gaaagtgaaa aaagaatcag tctctagagg gcttgtgga    75120 gtaaccgcct ggtaacagaa ggtcaggca gggaaggcaa aggggctctg cgcggatctc    75180
tcagctccgc aggcgcccca ctctcctcca agggacccga gcgccatctg ctgagaggag    75240 aacacgccc gccatggttt cccaaggagc agcagacacg gacctcgcag ggggcagcga    75300
acccacgtga cacagtcttc aagtcctttg gagagcccca ggaaggaaca acagcgtgta    75360
caccctgtga tggaatgttc tctagggcgg ttcagtgtga atggaatgtg gggccggtgc    75420
cattctaatt ggttctgttt ccctctagtg gttgatcgcg gagatttcgg cttctccatc    75480
aggacaagtt cagatagcct gagatggtat cagaactcag ggacagagct gggtgtggcg    75540
gccctgcatc catctgcttt ctctccatgc taactgatat ggtcagagag ctggaagcaa    75600
attccaggac cccagggctc cgcaaaggca aacacattac ttcatcggct gctgacatgc    75660
aacttccccc aggggttaaa acaatgttta atactaacag taataatatt tttgagtttt    75720
actttatgct ggcgctgttc taatgttgta agtgtattaa ctcatttaag ccttacaaca    75780
acctaaggac atgggagtca tagttcccat ttaaaaaaaa aaaaaaaaaa agcccaccat    75840
tgctctgagg cttttttatgt tttggatcca aagctaatat tggtggtggt aattcccatg    75900
```

```
cctggcttcg atcaattaat cagcaaatgc ctaggactgc ttagggttct ggccttcatc   75960
aagaccttac ccgggctttta tgatgatgac acctggcttt tcaatagcca tgactgctca   76020
cccaggaggc aacgcctcga gtcatgcacc gaacaccttt tattgatcct ctccaacacc   76080
aggctccgtg atggctgagc tggggacacc tgtgactgca cgtgaacatt ttgaggctgg   76140
gaatcccaaa ggccctcggc gttggcctgg gagcaccatg aaacaagtag aagcagagaa   76200
ggatggcaga ggtggccctc tgcattaggg cctggatgta tacactggtg ctaaggggc   76260 cccacagcta atagggggttt gagtttgact dacagcccca ggcaggaatc tgtgagagtt   76320
ctcactgaac ctggtgtggg ggtggccctc ctaaggcatg ttgctaaagg ccatctcttc   76380
tgccactgac gcctgtgttc tgcaggtcca tcctgacggg tctgttgcca ccaacctctg   76440
ggactgtgct cgttggggga agggacattg aaaccagcct ggatgcagtc cggcagagcc   76500
ttggcatgtg tccacagcac aacatcctgt tccaccagta agcgacacag gaactgagac   76560
cgccccatcc cctctcctca cctctgcccc cagcacactt ctctagagcc cagctcaggg   76620
gtgccaggcc tgggcacagg cagagataca gactcttatt tggtttcccc tatgtttaaa   76680
gtcctttgtc ctacttgcag tgagaattgt ccctgagaat atgggactct gcctctgctg   76740
ctcagagctg agggctcctc cctcagaagg gtgaggctgc cttcgctctg acagagcagc   76800
tgatcgatcc ccgagcccct tgtgcagccc tgaagtactt cctctctggg accaaagaca   76860
ggagaaccat tgttcctttt tcctgttgaa gccacggcct gaaaggcaaa cttttcaggg   76920
ggcttttcag ttactttttt tccccaataa gatatctttt atttcttatc taagaagcta   76980
cgcatagtca ttgtgaaaga aaaaaagga agggaggaag gaagggagga aggaaggaag   77040
gaaggaagga aggaaagaag ggagggaggg aggggagaag gaagcgaggg agggagggag   77100
gggagaagga agggaacagg agggaggaa agggaagggg aaggaggaag gaaagggaag   77160
gagggaggaa gtaaatatag gtaaacaaaa aattgaaaat aaaagtcacc tgtaatttca   77220
ctactcagag ataaccgctg agttataaca ttggtatata atttttttaga actttctcct   77280 atacatgtat agatagataa acacatatac ttcaaaatga taaagaatag taaaactatg   77340
catacaattt tataacctga ctttttttc aaaaaaagg attgcttttt taaacataag   77400
atatcaggaa catctttcat gtcattacat attcttctat aaaataatat ttaatgttta   77460
cagattattc cattgtatgc atgaactatg taagccatcc tcttattaga tatttaagca   77520
gggtctgcta ttttttgtatt gtatcataaa caccaccaca gtgagcatct tgattgccaa   77580
atcaagaata cttgtcctca attatttctg taagatcagc tgctggaagt ggaagtgcta   77640
agccactgct tttctcgttg tcccatcctc ctagcctcac ggtggctgag cacatgctgt   77700
tctatgccca gctgaaagga aagtcccagg aggaggccca gctggagatg gaagccatgt   77760
tggaggacac aggcctccac cacaagcgga atgaagaggc tcaggaccta tcaggtgctc   77820
agagctggat ggagacaggg ccacagatgg caaatccatg gctccccagt gcacccagga   77880
ggcaggggag gcttggagca ggagagcttc taagggtggg aacacctctg tgaagttaca   77940
ccaaaaatct aagagcagcc cccagatcat tttccctgca gagcactgtc tcacagcagc   78000 ctgggttttta tttgtcctga gattgatgtg cttgaacagt cttcaaaggg tctgatccga   78060
ggaggtgagg gttgcccttt ctgcatttac aaagcctgaa cagtattagg gctttgaacg   78120
ctataaacat ctaagaggca gcaccaaacc actgctgggt taaggtaccc ccacaatgcc   78180
acttgccctg ggcctttctc ttcctcaccc tccacagccc cttaactctc ccgtccttct   78240
tgtgcctcca ggtggcatgc agagaaagct gtcggttgcc attgcctttg tgggagatgc   78300
```

```
caaggtggtg attctggacg aacccacctc tggggtggac ccttactcga gacgctcaat    78360
ctgggatctg ctcctgaagt atcgctcagg taacagctgc tgctcagtct cctgggctgg    78420
gctctcactg cagccctagc tgtggtcccc actctctcac ctgccatttt gtagctgagt    78480
acaggaacca caatgactac actcagaagg gggtttatca gtgacttggt gaatctaagt    78540
tccagctaaa gcctcctgag gttttttacaa atataaacag agaatcactg atgatgcaac    78600
ctacttccca aaatattttta gaaaattctc ttgacctgca gcccttctgt ctggaataat    78660
ggatgctact ctaggtgaat gtcttctctg accatgggga cccaggtcac ctgcaaacat    78720
acctagaagc tccatagctg tcagatgacc actcaggacc agtgtgaggg tgacctgctg    78780
ggcattcagt gctccagagg gtggccacag atggaagtgg ctcctctgtc atggcacctc    78840
tcagacaagg ggctcagatc agaagagaca gcaagcagag ctgagtgccc atagaggtaa    78900
cagcacggtt caaccccgtg gtcaagccag agctttcccc cttgctctac tcacacagcg    78960
ttgccccgtg cctttctctg agggtttgtc atcctgaaat cctcattgct attttctttc    79020
tttcttttct tttttttttt tttttttttt tgagacagaa tctcgctctg tcgcgcaggc    79080
tggagtgcag tggcgcaatc tccactcact gcaagctccg cctcctgggt tcgagccatt    79140
ctcctgcctc agcctcctga gtagctggga ctacaggtgc ccgccaccac gcctagctaa    79200 ttgttttttgt attttttagta gagacggggg ttcaccgtgt tagccaggat ggtctcgatc    79260
tcccgacctc aggtgatcct cccgccttgt cctcccaaag tgctgggatt acaggcatga    79320
gccaccgtgc ccggcctgct gttttctgtt aatgacatct ccagttagtg agagtatgca    79380
cgtgtgtgtt ctttatgaag agtataaatc cagagcttaa tgatccagaa aatgtacata    79440
tgaaactccc tagatgctga ccataataca tgagccccta atatagagat ttatttgaat    79500
cagatcctat gctggataca gagacactgt gtgtggcaat gctttacagt atgtaggaag    79560
ctatgaaatg ttagttatta ttgtcctaat atgctggaat ttgctgctga attagttccc    79620
ttgggttttt tttttttagtt aactcctgat ttttgcaact atatagccag gaaattgctg    79680
tacacccttt accaacaatg cccaacccag ggcaggcctg gtgattgccc tggcccctac    79740
cttgcaggca gaaccatcat catgtccact caccacatgg acgaggccga cctccttggg    79800
gaccgcattg ccatcattgc ccagggaagg ctctactgct caggcacccc actcttcctg    79860
aagaactgct ttggcacagg cttgtactta accttggtgc gcaagatgaa aaacatccag    79920
agccaaagga aaggcagtga ggtaggtgtc tgcccaggga aggaccctgg cctgggtgag    79980
aaggagcaca cagcacgggg ctgccactcc agacatggct actcacacag gctctcgcca    80040
ccagaatcag tgtctttgtt ctgggaccat ttgcagaaga tttcgatgaa cacattctga    80100
agcctcctcc tacagagatg ctttagccaa aatgaaacaa ctagctttaa atggtctgca    80160
agtattacat gccagattac acaccagttt ggtgcggttt ggtgcaacat agaagtgagt    80220
gtcttattct gtaaggttag gctgttttaa gagcaattgg ttgagcttca tttcaacatt    80280
aatattccct aattaaacct gaatttcagt ggtaagtgaa aactaagaag aggcctcctt    80340
gggtgctata acataaaaat gatgaaggca aaaagtacca accagcagag accacttcag    80400
cacatcagga gacccagttt tatgtctgtg ctgcgaagtg aacaaactgt gtcatcctag    80460
gcaaattatt taattcctcc ttttttttag tatttttttc ttcttcacat ggaacatgaa    80520
gctaatgacc tctgcttcta tttcttaggg atgtgaagat aagtgagata agtattata    80580 aatgtgctct gggcttctta agaacaggca ttgctcacat tcaaatggtc atgattatga    80640
```

```
tatggcagca ttatttatgc ctctggttta agtgtctggc tgccgctggg gtttcctatg   80700
tccatccacg gggagggagg cacagaatgt ctcccacagg cagaacctac agctgccaca   80760
taattgatga caagccaaag ggaccccttgg aggttctgct cctctctgtg tgtgactcac   80820
acactctcta ggataaaatc aagcgactac accctcaaaa tgctcagatg aattaacaga   80880
ttaaacagtg aagaaaaaaa tgtgttgact acacttggca gtgagaaata aataaagcgg   80940
gcggtgacag cagctggcat cagggagagg ctgtcatgga agggatgtgc atcttgtcag   81000
tcatcccatc catctgttgc aggggacctg cagctgctcg tctaagggtt tctccaccac   81060
gtgtccagcc cacgtcgatg acctaactcc agaacaagtc ctggatggta aggactggac   81120
gggccatact tgggttccgt ctggcagcca tctcccagta ttgctgggtg tgtcctgttg   81180
tgatgcattt taatgggagc aaagagaaca ctgggtactt ctgcaggtca cacagttgtt   81240
cttttgcttt gagcttcttt ctcctcttcc ttcttccttc attcccaaag ggattttaaa   81300
agtcatgcac ctaaaggccc tctccctttta atgaggaata cactctgtgc tcttacccctt   81360 agtaagccat cattcctggg gtcccccctgc cctggctcca ggccacattc cttagtgtct   81420
ggggagagct tcttctacat gtgtgccgtg gcgccctcta gtggaagcat ggtgatgcac   81480
ggctcttcca gtgaattcgt ggagtcagag attgcacatg tggatggcaa gtctggaaat   81540
agcatacacc cctgttatac tcctgattct cccctcagct tcccaatttc ccagtgattc   81600
tccctttaat taggatgcac tgaagctctc aggggtgccc ccatctccaa ggagctgcag   81660
tggagaggct atcccctctc tatgtgagag aatgtgtgag aagcgtattc ccacacagga   81720
gcaaaactaa acttacgtac tgatgcaggt taatgaatgg ggaaagtatc tgcttatcaa   81780
agaaaaggca tattttttcta tttagcacaa acttttttcaa atgttaagaa tttactaact   81840
gaaatctggt gaagcaagag aaccgggcaa tatttgcgtt gtctgatcat tacaactgga   81900
gggaacatgc tcagagaggc atcatcactg ttcatgcacc tgccctctct ttacactgag   81960
agaccctgtg atgaacagaa aacatctttt taggatgaca tctctgggtc tttctccctag   82020 cctgccttgc tgtgggtacc tatctccctg ctctctgaac cttggtcaag aagtttatat   82080
ttgttttaaa ttgatactaa tatgttaagt tactgtgatt tgccaaaatc agattggaaa   82140
cagggcctgc atggctgaat gattcttttt tttaaattac tttatttcta aataaaggtt   82200
ttctttgtat agaatcggga tgctgtgaat ggtgggaaat gcactaaata gttatgcccc   82260
aaataagaaa gggaaaatca tttgaatccc cagttagctc cttgaaagtc ttttcactta   82320
aacacaccca cataccacac acacactcac agacctccct cccagatgcc caaagccctg   82380
ctgacctaca gagctacttc tggaaaggct gacacatgcc taagacacaa ttcctgggaa   82440
tccagcagct ttgggttcaa tttccttcct aaaagaacaa tgaatatgac ccctggagag   82500
ctattagggc agagctgctt ccttaacgta aaggactctc cagcctccgt atgaagtcat   82560
ctcagagcta aagacaatca agtccaactt gcagatttga cataaagcaa gacttccaat   82620
ccggctaggc agaaggattt tggttgaaaa ccatgaaatc ccttcatatg gatcattttt   82680
taaacaacaa aaaagaaaa gaacctactg ggtgtccaca actctgagag ctgctttctg   82740
aagagtcatg ttttgagtcc tggaatccct ctccctttga cctgcctctc aagacaatgt   82800
gcgagagaac tctctcttca agtgcatgca agtgaggttt tcacagttag attttttaatt   82860 ttaaagtaat acacatttgt acataaaatt caattctgac tgtatacatg tgtcagataa   82920
acagttgata cctgacactt gttcacagtc tatgatacgc accgcatatc ctaccctctc   82980
ccccagcctc tctccatggc ttctcaaccc cccctctgca tttcctgtga cctgaggatt   83040
```

```
cagttttgtt tgtggaggca ggtgcaatcc caagagaaac tgtgcaatct tctgagaagt   83100
tagagtaggc atgtgtgtgt gatttaggga aggtacttct cactcagctt ggtcaccggt   83160
tccaggtttg tgtcttgggc aagtccccca tagctggtga cagaccagaa aaatgaaaac   83220
aactttgact tagccctcaa gttttcagtg aatgagaatg aaaaacaacc atgagtaaga   83280
gatttcttac cgagatgatg taaaggataa taatagcagc cagcactcac ctatgtgcca   83340
ggtatttctc taactgcttt gtgtagtttg actcatccag tcctcaaaaa caacaatgaa   83400
gtggatacca gtattttccc cttttcacag atgaggaaag tctaatgtga cccacccaac   83460
ataacatagt ttgaggggac agagcatttc gttgaacaga ggaggaactg gcacaggaaa   83520
gttgcatgac cccccacca acctccgccc ccaggttgca cagctagcta gtcgggagga   83580 cttttgcttcc gtttccctct gcctctcaat gatgatctca gggccaacta agctaaaagc   83640
agacttgatg gagcatcagt cctctgaaag agtcactgcc gagatacaaa atacctcttc   83700
ttcaaagggg aagtggagag aagtaggaaa tctgggtaac ctcacagtct tccagtttct   83760
ggaaaacaga gctggcatca gtcttttttc ttgtcctagg ggatgtaaat gagctgatgg   83820
atgtagttct ccaccatgtt ccagaggcaa agctggtgga gtgcattggt caagaactta   83880
tcttccttct tccaaataag aacttcaagc acagagcata tgccagcctt ttcagagagc   83940
tggaggagac gctggctgac cttggtctca gcagttttgg aatttctgac actcccctgg   84000
aagaggtaaa gtagagattc cagctggttt ctgtcaagtg ccagaagtgg cggttctttg   84060
aaaaagtcta acattagagc aaagttttgt aaaagcaaaa agccatcgtt ccccacccaa   84120
gcatagcaac tatctttatt tttggcatag ttcccccatc tctgcatgca tacaaatttt   84180
atgtacttgt ggttactgtg tgcttacgtt tttgtattta tagaagatga tgttctcaga   84240
tagagtcgta atggattttc ttcccattat gaagcaatac ccaacaaaac agagcttggg   84300
ttagattttt ctgagaataa gaatgactaa acaaaattct ctctttttt cttcttgaca   84360 gattttctg aaggtcacgg aggattctga ttcaggacct ctgtttgcgg gtatggtgct   84420
ggagccagtg gcttgttccc ttccttgcct ccctcccaag ttccatctcg aaagtctaag   84480
gggctgggca cagtggctca tgcctgtaat cccagcaatt gggaggcca aggcagatgg   84540 accacctgag ttcgagacca gcctggccaa catggtgaaa ccccatctgt actaaaaata   84600
caaaaattag ctaggtgtgg tggcgcgcac ctgtaattcc agctactcgg gaggctgagg   84660
caggagaatc acttgaacct gggaggcaga ggttgcagtg agcagagatt gtgccactgc   84720
actgcagcct gagcgacaag agcaaaatcc atctcaaaaa aaaaaaaag tctaaggaaa   84780 aagtcatgaa acaacaaagc aggcaaatac tcctccatag tatctgactc cccagtagta   84840
ggcattttgc atcctagatg gctttgagtg acaaaggaat aacagactga gttaggtcta   84900
gatggggaca cttggatga atgaggattc ttacggaggt caggttggta gcttcatccc   84960
tcagctcctc atgctgtatc cccagtctct cggcctgcca tgtcatcatc ctcatctcct   85020
cctgtcatct ccaccaggcc tctgatccat ctctgtctgc atgagtgaca gctggcagag   85080
tccttaatgt ttatcaaata caactcgaga gtcagtctcc tggccccttt gagatcaaca   85140
taaaatcatt ttgaaccctt atttagtggt ctatgggctt tgaaacatg gggaccaaaa   85200 ttcctgtgga ttctagaagt ctctcttcta catgtgtcag cctgggcacc aactagctcc   85260
ttccatgaac ttttatcaaa cccacagcca cacaaagcat gtgtgagtgt agcagagttt   85320
acagcagagg gtggagggtg gggagataga tgtgtggaag ggttacctgc cacacaaaca   85380
```

```
gaaaccactt ctgatagaac acgaggtgtc cacccacact gtaaaatcct ctcctggtac    85440
aggcaaagct tgcagcgat tctcctttgc tgcccctggg ctcctaacac ctcctaaacc    85500
accagttacc tccttctttc cagtgtggca tatttcagtg ttttcctgtt ggagtgtttc    85560
ctttctatgt ggattctgga atcagctctt aagataactt ggttttcatc tttcttcata    85620
atgatcccaa acatctatct actatgccta gaactaccaa tggacacata taccagccca    85680
gatatgcttc agcccatccc agtacatcgc atggtgacca aaagatgtag tcgtcctggc    85740
acagtgggtg tggggcagga agcagtcctc tccaggggac agcagcaatt caccacagaa    85800
cccaagtttc tttcaagctc tgctgacaca gaaattgaat aatctcagct cacccaatgt    85860
caaagactca tattaaccaa gaccagaatg aaaatatgct aatttatatc agaagctttg    85920
ctggattcaa gagttagggc cttttacctg tgcagaatat tccttcttga taaataggcc    85980
ctctcaggag aataaattac acatcagagg actgtttagt cagcataggc atagaacagg    86040
atgttccaaa gatacagtca aggggagtgg gtaagagtgt agcctctgga gtgaggccga    86100
ccaaatatca aacctgagct tcataatttg caaactaact ggctttgggt aagtacatag    86160
cctctttgta cctgtttccc catctgcaaa atggagataa taatagcatc tacctgtagc    86220
attgttgaga gaattaagtg agttaatgct tgccgactta taacacagta tacgatcact    86280
gattaagact tagcaactct aaactaaatg tttacaaacc atctcttacc tcaaagcact    86340
taacatccat tgtcttattt gattatcact gtaatcttat gaagcaggca gggcagggt    86400 ctgccccatc tgggggaac tgagctcaca gaggttggag ggtttgccta aagtcaccca    86460
ggccactggg tctcactctc tggtcttagc tctgtaatct aggatgctca atgccacact    86520
ctcagccact tttcagatgg ctaagtacat ttgttttgag ttagctcagt ctcagaggat    86580
gacattttct gatcttgtct ccagtgttta aatgaacctg tagctgtgca ttggggtcac    86640
acaatgcgtg gcatggagag ggtctgtggc tgactgccac ggttactacg tgaaaccatc    86700
attacagcag ttactactgt tactgcctga gaacatcatt acaagactga acgaaggat    86760 caacatggaa atgataacaa aaaaaccaaa gtaactgttt taaggaaagg ctagcatcgg    86820
gaagaagaag agagaagaag agaagaagaa aagggctccc tgcttctaat gagtaaaggc    86880
agctccctaa gcttctgcag ccctttcatta tttattgggt aacaggagga aggagcagga    86940
ggtaatgatt gggtcagctg cttaaatgat cacgggttca tgttgttact gacagattc    87000 aattatgcct aatcataaga aacatttgtg cagcctccaa caagggtcaa tgccacttct    87060
gaaggggtga ctcatagtca gtaactagaa agcagcagat agctagggac aaactggcga    87120
ttctgaatag gcctggaacc cttagctctg gccaggtcag tgggctccag tcaggatgga    87180
gccttcaggg agagatcaaa gctcagaggt ttgagatgat atcagccagc aaagaggagg    87240
ggcagtaggg atcctcccag agggagggcc agccatagaa gacatcaaat ctgagcccgg    87300
atcaggagaa ggagcctgca gaactggggc tctggcaccg agaacctgca gaacttcgcc    87360
cctctgagtg caggtgccag ggctgggct gccacccagc cttcgcatcc caggcctggc    87420
acgtcatagg taaatgtagt tgaaaggatg actgagctga tccaattccc tttacaactg    87480
tccttgtcct gggggacttg aggagggtta agaaagcagc tggggaccaa ccaacagtcc    87540
tctaggctct ccatgtccag caatagttgt tcagcaaatg agcattaatc agtgactata    87600
aactgtagct tcaacataac cgacaacttg caatggtttc tagagcatgc tcccatgtgt    87660
tatctcattt aaatttccaa accaatcctg tgaaatgttc ttttttttt tctttttttt    87720 tttttgaga tagagttttg ctctgtcacc caggctggaa tacagcggct cgatcatagc    87780
```

```
tcactgcagc cttgacctcc tgggcccaag gggtcctccc acctcagcct cccaagtagc      87840
tgggactaca ggcacacgcc accgtgcctg gctaatttct tttctagttg tttgtagaga      87900
cagggtctcc ctatgttgta caggctgatc tgaaactcct ggggtcaatc aatcctcctg      87960
gcttggcctc ccaaagtgct gggattacag gcatgagcca ccatgccttc attttacaga      88020
taagaagtct gagaaaactc agatttaggc agattgagtc acttccccaa atttatgtat      88080
cttgtaagaa tccatattca aacctcagtc ccctaactct tagttcatta cttttttac       88140
cacttctcag tatcctctaa gaattcagaa agaaccacat cgactctgat ttttcatttg      88200
tttaagtaca caggtaatag gtgaatgtat tttgttgttt aaaaattcat ataatacaca      88260
aaaggctaaa gtctcgcttc ccacttcctc tccccttcct acccaactct gcctccccag      88320
ggagagcttc tgctgacagt cggtggacat tctttcagag ttttacaatt atgtgtgtgt      88380
gtgtacataa gatgtcagtt tttctttgtg taggatacat gaacatgaat tttaaacata      88440
aatgtgagtg tattacacat attgaccagc accttagttt ttttgtttgt ttgtttggtt      88500
ttctttgtgc tgtttgagaa ggagtcttgc tctgtcaccc aggctggagt gcagtcttgc      88560
aatctcggct tacgcaacct ccacctcctg ggttcaagtg attctcctgc ctcagcctcc      88620
cgagtagttg ggattacagg tgcctgccac catgcctggc taattttttgt attttttgtag    88680
agaggggggtt tcactatgta ggtcaagctg gtctcaaact gctgacctca aatgatccat     88740
ccacctcagc ctcccaaagt gctgagatga caggcgtgag cctccgtgcc cagccagttt     88800
tgtttttttta ttaaccaagt tacgtatttt aaacttctcc atgtcaatgc ttttagagct     88860
attttgttct ctttaatgtt aatagagaat tttaaggcaa tttcaggtga atctatacaa     88920
tttctctgta taagtaattt acactagaaa tagattttta taaagatgat taagctacca    88980
gcctggtatt tcattgctga cttaaatgaa gaggaaaatc aatgctgtaa gggaaaaaaa    89040
aaatggcatt agagatccag acctataagg cattttccaa attattaatt caatctctca    89100
aaacaggtgg cgctcagcag aaaagagaaa acgtcaaccc ccgacacccc tgcttgggtc    89160
ccagagagaa ggctggacag acaccccagg actccaatgt ctgctcccca ggggcgccgg    89220
ctgctcaccc agagggccag cctccccag agccagagtg cccaggcccg cagctcaaca     89280
cggggacaca gctggtcctc cagcatgtgc aggcgctgct ggtcaagaga ttccaacaca    89340
ccatccgcag ccacaaggac ttcctggcgc aggtactatt gtcggtcggt gtttagctga    89400
gctcagtggc tcctctccca gccttcccct cctctcctga gtgttccttc aggcatgggt    89460
tataactcag caaggagcac cctctcttaga ttctgctggt tttgtttcct gctttccaaa    89520
cccttatctt gattcttggt aacatgaatc ttctttgtaa gttggacctc ccctagcaaa    89580
gaaaatagaa taatagtgaa aatgttaata ttgttttttat ttttacagtg agggataaag    89640
tcatgttttc attcatttt gcagtgaccc tacatatcaa aatcattgcc ctcttttttc      89700
ttttaatgtt gttttaatta gaaaaagaag ctctggttta aagaacagtg agtcacgtga    89760
cttgctcttt gaaatgccct ttgaagtctg gctgaacact gggctgcatt cagattcttc    89820
agtggccacc agaacattct gttttcttct gcacatctta cctttgcaca ccctgcttat    89880
tatgttcccc cagaagccca accctctcca ccaggggctg attaggaggc tgcaggataa    89940
atgtttaaaa gaatgaagat gtgtgtgcac gcgcacgtgt gacatctcca tgccacagtc   90000
atgtttattc cacgtctatt ctcccacaga tcgtgctccc ggctaccttt tgtttttttgg  90060
ctctgatgct ttctattgtt atccctcctt ttggcgaata ccccgctttg accccttcacc  90120
```

-continued

```
cctggatata tgggcagcag tacaccttct tcaggtgcgc ggactcgggg tcaccattct    90180
cctctgtggg tttggggcac ctgggtcaca tgctgcttag aagggccctg accttcccac    90240
ttcactggga ccttcaccaa tgagagaggg gaggggtctt tgggctgcct gcagaaagga    90300
acttaatgta tctgccactg cttggaaagg cgatcctagt ggacaggcag gactgcttgg    90360
gaaggccgaa tggggaaagg aatgcaaagc ttaggtgaat gggttgaagc gccatctttt    90420
tgaggcatag gtgacatgcc atcagaccac tgcgagtgtt caggcagcct accgcactcc    90480
caggagagct agcgccatcc caaggcagca ttcggtgcct caatacata cctggcacac     90540 agcagctatc cagtaaaggc tctgagttgc atgatgttgg cacgcgcctg ctctgtccca    90600
gtcacatgtc tcactctgtc tagcatggat gaaccaggca gtgagcagtt cacggtactt    90660
gcagacgtcc tcctgaataa gccaggcttt ggcaaccgct gcctgaagga agggtggctt    90720
ccgtaagtgc ctacgcgccc ctgtcctaag aagactagct cccctgggag acccaacgg    90780 tgggttcaag atggcaggcg ttggggaggc cccactcaat cctgctctgc tggtcacttc    90840
catgtctctg accagcactc ccccaacctc tccttccaca cttgtgtgca gggacattca    90900
ctacctccta ggaagccccc acaccactgg acagctctat atttctcagc atagaagttc    90960
tatgttgagt tgacagatga ttccccataa cttatttgaa aggcctctga gcagggaggg    91020
agggaaatag ggttatgcta ttgtgtgatt gggccttgaa tggcgtgagt gacacagtgg    91080
ccagtacttt gtgatagttg tgagtctgga aagggagtt agcgaaggcc attgacatcc      91140
accaggaatc ctaaaagttc aatataattt taacttttct ccctcagtct ttttcaaagc    91200
tgtcaataag gaccaaaaca gactaatttc aaattcctct tctggttgct gtgtctctca    91260
acagctagag ctgctaggaa taaaaaggga gacaaaacga tccacaagct agagatggtt    91320
attccccagc cccacaccta gtcagtcaca aaaccctagt tttgatattg cttgagcaga    91380
aaccagcctc caagagaata agaagaaagg gcctgggtct aaagaggagg aggaaagggt    91440
tgggcacaat ttcttatgcc tagggatttg tcagcaactt tgaggctgat tatgaatat     91500 tttcttgtct tccatgaggg agtacccctg tggcaactca acaccctgga agactccttc    91560
tgtgtcccca aacatcaccc agctgttcca gaagcagaaa tggacacagg tcaacccttc    91620
accatcctgc aggtgcagca ccagggagaa gctcaccatg ctgccagagt gccccgaggg    91680
tgccgggggc ctcccgcccc cccaggtacc tgacctccaa acaacggggc cccaggtctg    91740
cctgccacag agggactagg ggagtccctg gtatctcctg agtctctcac aaactaacat    91800
ttcaaactgg cagttgagta ggggactaaa ccaaactccc tgcaccctct ggaggggct    91860 ccccacaggg cgctgtggct gccaactgga ggaagccact caccaaaagc ttcatttcc    91920 accagatact tcctatttga tctagtagaa aaaatgtgtt taagcactaa aaaaattaa     91980 gtcatatgtg ctcattatag aaaaattaga aaacacaggt aagtcagaag gaaaaaaaat    92040
catcgcttgg atataaacac agataatgtt tggtttgcag ccacccaaac agattatatt    92100
ccaaatattg tcttaaaatc tgatttactg cataatttac taggaacatg catccatgtc    92160
aataaataga catctgcatc acttttaata tctgtatatt atcccattgt ttgaatttct    92220
tttttttttt tttttttttt tttgagacag agtctctctc tgtcacccag gttggagtgc    92280
agcggtgtga tctcggctca ctgcaacctc tgcctcccag gttcaattct tgtgcctcag    92340
cccccccgag tagtggggat tacaggcatg caccatcatg cccgcctaat tttttttggta   92400 gttttagtac agatggggtt ttaccatgtt ggccaggctg tgttgaact cctgcctca      92460 agtgatctac ccacttctgc ctaccagagt gctaggatta caagcgtcag ccactgctcc    92520
```

```
tggcctaaag ttactttaaa ttaactgatc tcccattatt cgccacttag gttttttagt    92580
tttcaccatt ataagcaatg ctatgatgta cattcaaatg gaaatgtgtt tacacactta    92640
ttaacagtct taattaagaa gctctccatg tgctgtgtct ctaacatctg caggtatgta    92700
cacaaataca tgcacagcca gcatccatct tttgcaggga cattaatgat cttggctctg    92760
agcagcaccc tgtcctggga gttctaaagt ccagaacaga ttacagtgag catctcctgg    92820
gggatttaga gacatcaaag aaggctgtgt ccgtggttga taatgggcct cccagctgac    92880
ttgccagggc tgggccttag acagccctgt ccaatgattt gtcaatgaat aaactgttcc    92940
caaacaggct atgcagttca gtgggaaagc acaggtatgg gacacggaga gccccaggtg    93000
gactacttga cctctctgag ccttaatttt atcacctgtg aattgggaat aactgcttat    93060
ttcataatat tattatgagg atttaatgaa atcatgtggg caaggaatta tttagaatta    93120
gattcaactc aagtgatgac aaccccaaac taacagcaga taaaacaaga cacaacttgt    93180
ttctcactca tctaaaagtc tacgtgggtg gtgcacgatg ttctattctc tttctcctcc    93240
acactaaaca ggcctcagcc tcatcagcca ataaggcagg agctgccttc caggcagcgg    93300
aatggaagaa ggatgaagca aaacagaggg cagagtgtgc acatgtgcta tgtttaggga    93360
aggttttctg aagttcccac atagtacttc cacttacaaa cccaacaaaa aaggctatgg    93420
ctaaggcagc agggaggagc aaataatggg agcaactaga ttttgccaca gcacctatca    93480
cagtctggtt tataaatggt tctaggccaa gaacacccga tccctgctct tttttatatt    93540
ctaaagcatg tatctttata tttctcaagc aatattttct ctctttgaat cacagctcat    93600
ctgctgcatc atagggatcc caaaagaagg acccaaggaa cttgtctcag tcctctgtgc    93660
cccaagagga agctttgctt gtttgctttg ctgtcaatgc tgagggctcc tgtggctgcc    93720
tccactcaaa accctccagc atcaggacgt caaggctgtg atactgtacc ctgagctctt    93780
ggccagggcg agggagggga ggccaagcct acctacatgg tgtttcattt cctaaacgaa    93840
cccttacttc cacgcggtct gtccagctta gaaacttatt ttcagtagtg ttggtccttg    93900
gtccctggac aaaatgtaac agccaaagtc ctagaaaaag gcaagccagt tcctgccatt    93960
ttctttcact tctgcatttc ctcactatta tacgtgcctt ccattggagc aaaactgaat    94020
gccacgcata tgcacaggag ctgtgcgcgc tctgtctctc tcactcactc tttttctctc    94080
tctctctttc tctctcaatc tctctgtctc tatctatctc ttactcttta tctctcactc    94140
tctcactctt tctcactctt tctctcaatc tctttctcat tctctctcta tctttctctc    94200
tctctctctt tctcacacac acacactcac aaacccacac tcttattcac atctgctcac    94260
cctagccact caaacacaat ccctcattca gcctggaata agtccagagg gcgtgggcct    94320
gattcagaga caatcagttg ttctcatctg ggaaatgggg caatgtggtc atctctaggg    94380
accctccctg ctctaacatt ctttgaatgt ggtgggtcct gaggtggaag cactctgtcc    94440
ctgacttcta gtatatgtgg agataggggtt acacaaatat tttattgggc agaacttta    94500 taaaacaatt tatcataagc tatcgcagcc agcagcaatt tttccaacct ggattccacc    94560
aggggagctt ggccggtgtc tgagtgccac tttcagcttg agaagcaggt gactcagtga    94620
aaagagcaag gaggagacag aggcagattc agttcctagg ccctgggcca cccacctgca    94680
agtttgcagc ccagtcagtg caagtcagct aactgttctg aacctcagtt tctctgtctg    94740
taaattaagc taaaaattct tctttcaaag agtgtcagga tgaagtgaga tcgtgtatgt    94800
agggcattta acatagtgcc cgacacacag ggagcattcg gtaggtgcca gctctcctcc    94860
```

```
tggcaggaga gagagaaaca aggtgaaaag agtgaattaa agaagaggaa agtcaaatgg    94920
gaaaacaggg ggaggagata gaaagtgtat gaaaaggaaa gaatggtgcg caataacggc    94980
ggtgtaatgc caccaaaatc ccctcaacta cttctgggca gcacccttga cagagtgaat    95040
gcttttatga gaatgtaagc ggaatgtgtt cccagatttg cagtaatatt gccacctggt    95100
ggacaaaccc atgcaccttt gaattttcca aaatatttcg atgaactagc ttccagtcct    95160
agatgtattt tgaaagtgat ttgtaaattg taaggaacta ttcaaattct ttcattaatg    95220
tcacaaatca actgtgtcat ctgtatgcca cccactattc tgggtgctgg ggacacaaca    95280
gctcacaaat caggcaaagt ccctgctctc accaaaatga tatcctacgg gggattacag    95340
atacaaatac gtaaacagat ccatcgggag gaaactctca gatggaaatg agagctatga    95400
agataacaca acagtacatg acaatacaga gtgactggaa ccaggaacat ttctccgagg    95460
aataaaattt gaagcgagcc atgagagggt ctacaggtag agttcccagg cagagtgaac    95520
agccaagcac aaagctgcac caggagagag aggtgctcgc cgagagacag ggaggggagt    95580
gtggcaggtg agctcagaga ggggcagggc cacacacatc ggcccatggg gccttggtag    95640
tgagtcgaga tttgatccca gggtttattg gagtggataa gtaagcaagg tgactgaggt    95700
gctcgggttt acattttat agttcaagct ggctgctggg tggaaaacgg aagttggcag    95760
accaaggaca gaatcaggca gacccatgtg gaagtttctc tagtggtcta ggtggtggct    95820
tgggtagcgt ggcagtattg gagctggaga acgcagatg gattggagat ttgttttgga    95880
gtgacgccat tctgtcttgt caatggattg gcgaaaaaag aggcatcaaa gatgagttac    95940
acatcattga agtgagaact agggagatgc cagtactttt tttagtattt tctcagcagc    96000
tcaatccata ataatttttt ggaagacaac aagcagtttc acaaactact tataagtcct    96060
caagttccaa ggtaattaac gtgggtgtct cattgcctca gagaacacag cgcagcacgg    96120
aaattctaca agacctgacg gacaggaaca tctccgactt cttggtaaaa acgtatcctg    96180
ctcttataag aagcaggtaa gaagaaatcc ttttatgctt tttatcctgg ctccctgtag    96240
aagatattaa ctagggacag aagataattt tctctctcaa tttatgtatg atcagggcag    96300 tagattttt tcttttttat ctgatttgag ggccccattc aacataaaaa gcaattgagg    96360
cacatacaag taaaatgtaa cttaagatta attctttttt tgttgtttgt ttgtttgttt    96420
ttacatttag ggcaagcagt cttaaatttt aacccacgta ttattaaaag ttatatcaga    96480
agaccataga agttattcaa aaatgcagcc acatattta actagttaaa agagagagta    96540
aaaatttgga gggaggtgga ggagtatagg ggaaaaggta gaagaaaaag agaaaataag    96600
taagtggcaa aaaagagaaa ggaaaaagat agggtgggaa agaggcagcg ggacagtgtc    96660
tgagtccagc acacgccagg gcgagccagg tcaactgcag ctgtcatatt ctaactgtga    96720
attatcatct ttgatcactg cccttgaga tgccaatgaa cttttcaaga aatatctagt    96780
tctcttggct ctccagctgt tcttatcagc cccatccagg atggaacagc tttggcagcc    96840
cgtatcagaa caagcagctt gacaggggca tgccatgcca ggagagagga tcctaaggaa    96900
gcgtggtcca gtccgcacag gctctggggc tttaagataa aacctcctgt ctaactttag    96960
taggactttc tgttgcttca cctgccagag ccctgaacga gggataaatt gacttaatta    97020
actagaacac actgcaaatg gtgaaagcat ttagcaaaac aaagaatgcc atccaagccc    97080
caaaataaaa gcagaataaa tagaatgcaa taaacagcaa ccatcccaaa ctgagttctc    97140
agcagcaaat ctccagtatg aaattttgga ttttgtgcgt gtgtgcttaa aggtggatga    97200
caatgacagt tcatgggatt gagctctggg gtccagagtt ggcatctgtt catttcccat    97260
```

```
tttgtcattt taccctttgat tgactgaatg tcagtgcctt aactttgggc tgtggagtga    97320
gtcggaactc ccccgaggtg tgcaggtggt tgttagagtc tcattttgc agggtggaag    97380 acaggagggc tgcagccttc attccacact gacatggtca ttgccgtgtg ttctgggtcc    97440
agatcaggca tattgacctg acatatgacc tgacaacagg accactcaga aagtccagca    97500
tgcgggatat gatttggaga gccagtgggg gaaatcatag gtcctttctc tgcatgtgta    97560
ttcaggcaat gtcccagggc tgggcggctt ccgcattgct tggatatcgg aaaatgcaaa    97620
aatgcccctg aagactgaga cttcagtctt caaaatgaat gtttgggaaa gaaagttaac    97680
ggcactgctg tacttgtggt attcattgca ttattttatt ttggctttca gcttaaagag    97740
caaattctgg gtcaatgaac agaggtaaga aactattttt atcagaatta aaatctcaga    97800
ttgattcatt gttgaaataa ttgcacactt ttaaaaggca cacctcacag ccatgaggag    97860
gggctgttct gtaggtgctc aggaagtcac aagcacgtc ctgaagaata tgtggctagg    97920
gacatcccag actcagaaga cactcagtgg tgcctcttct tggaggacat aagtgggggt    97980
ggcattccct gatgtggcgt ttcagagcat tctcacccaa aaaaagcttc taaaacctcc    98040
aagtatataa cagtttataa tactccaaca agagggcctt gtagcctaaa cccgggacac    98100
tccttggccc attccttta agcttcaggg agtgtgggcc agcccagac tcaccccatt    98160 cctgaggcat cctggaggtt gaaatatttc cagaggttta gaacctcacc aagtgggact    98220
ctaggagcct gctgcctccc agcctccctc aggaactgca cctccagaac aggtgcgggg    98280
ctgacatgta tgtgctttcc tgggcagatt ctagaccgta cacatgaaat ctggctttca    98340
ggattgctct ccagagggac ctgtggggcc tcggctgaga cagagagtag gagtgaggca    98400
gtgattcaag gccctgagaa agagctcctc ctctgcttgg tataaccagc taattcattc    98460
tgttctgttg actttggctt ctgccctgcc tttgaagggt ttgaggccag ggagtgatgc    98520
actcagactg gtgttttccac acagtcactt cagacttcca gggcagtaca ggagatagat    98580
cccagggcca gtgaagaagc agagcacaag tccaggcagg agaggctaag ggcctccctg    98640
aacaggtgtg aggcacagaa gccccgagag gtagggatga caggatgaag atgggtcctg    98700
tgctgctaga agtacctgca aagcacagag gtggcacaga aaaggagtcc ttggctggga    98760
tgggaggaga tgacatgtga catgtgaaag aggacctgga gttggctcga tgctcccaaa    98820
agggaaaggt gccgagggga gctagcagcc atgcaaaggc agagacatgc aggcagtctg    98880
ggccatgagg agctctggaa gtgactcgat atgtccagaa taggccactc cagggaaggg    98940
ctgaggaagg atgaagttgg agaggggcac agaccagatg cagaagggcc tcagaggcca    99000
ggatgagggt ttggactcct tcctggaggc agcagcagtg ggaaaagagt taaaagctgg    99060
tttgtaaagt ggagccatgt tgctcgctgg tccaggcaat tcccccgaaa gttcatgttt    99120
ccctacaaaa cccgagagag ctactagtag gcgtgaagtt cgtggccctg gtctgaggat    99180
ttcctgtttc cttgtcaggt atggaggaat ttccattgga ggaaagctcc cagtcgtccc    99240
catcacgggg gaagcacttg ttgggttttt aagcgacctt ggccggatca tgaatgtgag    99300
cggggtatgt aaacagactg gagatttgag taggatttt gacttgctta actaccatga    99360
atgagaaact ctcatgagtg ataacaggaa aaaaaaatta aaaccgtctt gtttgtttgt    99420
ttacatggtt tttagggccc tatcactaga gaggcctcta agaaatacc tgatttcctt    99480 aaacatctag aaactgaaga caacattaag gtacttgacc tatgtataat ctgctctgga    99540
gctaaaaatt tacctgagct ggttatttta tttttacttt cctaccttca ttaaattcca    99600
```

```
tccctcctcc tgctgaaatc tagcaaggaa tgtcttccag ctaccaaacc cttcctgctt   99660
ctcaaatttc ctttccttca ctgatttctg ctttaactag ctgttagtgc agcgtctcag   99720
atgtcctctc caccctctag gtgtggttta ataacaaagg ctggcatgcc ctggtcagct   99780
ttctcaatgt ggcccacaac gccatcttac gggccagcct gcctaaggac aggagccccg   99840
aggagtatgg aatcaccgtc attagccaac ccctgaacct gaccaaggag cagctctcag   99900
agattacagt gtaagccacc acagcccag cctcaccact ttcttgtcac cttctccact   99960
ctttgaacat cctgagagga ttctcaccac cgcgaagtgc tgatttggat ggtaatgctg  100020
tttagtcagg cacatatgaa catccgactt tcaaataagt gcctcacact tcacatacca  100080
gacctcttgg tcattctttc tccccaacat ttatgtggca agtaagttta catttggttc  100140
cattcccttt tggcttttga tagcaagttg ctcctggagc ttatacaatt attatctttg  100200
ctatgtgcaa agcagctgcc aggaactggc aaagttcagt aaacctttca gctccctcgg  100260
agtaattatc ttagattcca ggaatttcct cagaagagca tactttggag atgtcgacag  100320
agctttgcta ccctcaagct gaggctcttc ttgcacagtt tcagccagtg gagacagtgg  100380
ccttgtgcgt tttgtagtat gttcactcta tttgaggcct acatggagga ggggttggta  100440
ggagcacctt tgttagtgca aacttcagca acgttgtggg gtcctgattt tactatccta  100500
gcacacgctg agtgccagtg aacatgccca gggtcatcca ctaaaacctg ggccttggct  100560
ccttggtgtc ttcctctgga caccctaggg ccctagactg tcctctgtta attctcactc  100620
agccacactt tcgtgtgtct ccttccagtc atttgttcta agcttactac gtgtatggat  100680
gatatgatct gtagttttat caaggtagtg actaccacat aggatacctt tgtggaaatt  100740
agtaaaaatg ctcttttctg caggtggaca ctgtcccatg ccaggggtta tggcttgtac  100800
ataaagttca ggctggcttt agccccaact taccccctcag ccagatgcct tctatttgtc  100860
cgaggaaaga ataaatagag ccaagtccct gtacaacttg cctgccctct tttcacttaa  100920
atttacatca tgaacatttc cttgtgttac gatgtacttc ttgaaaatgt gatttaacaa  100980
gatgattatt aacaaaagat aaatctcaca gaccgtatgt ctgtcaacat agaaaattca  101040
agagactcta tagacagatt attagagcta atgagagcat tgcagtacat aagattaata  101100
taaacatcta tttctataca ccataaaaat aattagagaa tataataaaa agaaaggttg  101160
tctagaaata ttcacatgaa atagaaaggc aacccgcaaa tacccattta accttggtcc  101220
atatggatta agacagttta gtggagtgac agcttcaagg tagagaagag gaacctggag  101280
gccacacctg ggcgggtgta aggccttccc aaagcctgac tttgtatctt ctcctccttc  101340
tgctcttccc tcttcatcgc cctctccctg tgtctctggc cctgctgcag gctgaccact  101400
tcagtggatg ctgtggttgc catctgcgtg attttctcca tgtccttcgt cccagccagc  101460
tttgtccttt atttgatcca ggagcgggtg aacaaatcca agcacctcca gtttatcagt  101520
ggagtgagcc ccaccaccta ctgggtgacc aacttcctct gggacatcgt aagtgtcagt  101580
ttacagcgcc tccctcccct ccgtgggccc aaggtggagc ttgtgtgtgc tctgaaggac  101640
cagaccaaga ggggaggggt tctcacggtg ccagggctgc tgaaaggcac tgggccaagg  101700
gccttgtgta tctgctgtcc cttgacatct tctcagaaag gcacagaact aggagcccga  101760
agctaggaaa ggctgtgggg tgcagcttaa caactggtga acgggggctc tctatgtcct  101820
gcactgaggg gtcttctgac ccatcaaata atcactgcac cgcaggcatg agtctggcct  101880
tcctggcatc agtctggcgc tgagaaggta atatgaaggg gtctttcacc ccaagtcccc  101940
ttctcaaatc ctgccccacc ttcaaaaggg taaaggtaaa actttccctg tggtagggtc  102000
```

```
accagataaa tacaggacac ccagttaaat ttaatttcag atgatgaata attttagta    102060
taagcatatg ctacttcaaa tattgcacag gacatatcta cactaaaaaa aaaaaaaaaa   102120
aaaaaaaaaa cctggttgtt tatctgaaac tcaaatttca ctaggcatcc tagattttta   102180
tttgccaaat ctggcaaccc cagccagtgg ccaaaataat aagaccttca cttattagat   102240
taaccaccgc tacagggaaa aatgaagaaa aaatatttat taaatcaata gcacactacc   102300
accttcctga caaccaaggt tggtgggggt agggagggggt caggatagcg taccctatta   102360
caggctgcag ggtcaaagga attggtagta aaggcctagt tataatgtaa cagggatcat    102420
tatgacatca accccaattt attctaggtg tcttgagtag taaaatctca acattttaag   102480
accaacatga gcctccattt catgtgatga taagatatac caactgatgg agaccaacac    102540
aaatgacctt ctcatccatg gttttttaaa atgatggtga atattggaat tcctgaagat    102600
atgatttcta tcttactcag cttagtaagc agctatcact taacaataca aaaccagaga    102660
ttatcagtag caactaaatt atttcctctc tcttctgtct acacgaggaa acactcataa    102720
atgcacgggg aggaggtcag aacctgaaag cctttctttg gataagagca tcaactgcag    102780
gtaccacatt ggccctgtga tgctaatata aaaggagcta ggcccaccgg taccgaaaag    102840
ttacttagaa aagtgcggag gcttttaatt ttactttttt taaaagataa gaaatagaat    102900
ttacacactt ggggctggcc cacgtgtttc tgtgtgtgtg tatgtgtgca cgcacgcgcg    102960
tgtgcgctta cagggatctc tgagcctatg gagagagatg tagctaggat agagtggaca   103020
tctgaggtgg gaggtgatac tagctggcag tccaatgaag gggtagaaga tggtaggcat    103080
catgttagca ggctttctga tgctccagaa ttttaaagct ggcctggaat ctcacctccg    103140
cgatccatca ttttggaact taggaccacc attagccagt ggcaaaaaaa aagttgaatg    103200
aaggaacaaa caattattgc ttatgtaatt cacttagcac atatatgatg ttttaaattc    103260
ttatatgtgt catctatttt tctttactttt aaaatttgc aacagttaca gacttatgga    103320
aaagtcacaa gtacagttga aacctttttt tcttagtcat ttgaaagtaa cttctcagca    103380
agatgcccct tctcatttat ttctctcttc ctgtctctct ctctcacacc cctcagcacg    103440
tccgatgtat acttcctaca aacgaggata caccccatac aaccacaaca caaactgtca    103500
acatgaggaa accagcactg atgtgtcatc accacctaat cctcacaccc cactcctctt    103560
tcgcccattg ccccagtgat gtcttttcaga aaaaggatc tagctcagaa tcatgcatga    103620
catttgattg tgctgtttct ttagtctcgt tcagcctgga agagttccac agtctttgt    103680
taacactcat ggtcttgaca ctttgaggac tgcaggctgg ttattttgca gaatgtccct    103740
tggtctgagc ttgtctgagg tttcctcttg cccaggttga gggtgtgcat cttggcagca    103800
gtatcagcaa acagatgctg tgttctcact gcatcctatc aggtggcttc tgatttcaat    103860
ttgctctgtt actgatgatg ttcaattcgg tcacttaaga aggtgtctgc tgagcttctt    103920
cactgtaaaa ttactctttt ccccttata ataaatacaa atttcaggta gaggcacttc    103980
aaagatatat aaatatccta ttcattatac aattttccat ttattcatcc atttatttat    104040
ctctgtatgc agtcatggtt catgtgttaa tcaatggact atgatccaag actatcatta    104100
tttattttga tattcacatt atccccactg tggtcagtgg ggggccgttg aagctggctt    104160
ctgtatcgtc ttgacttggg tcctcatgcc cctggacctc ctccatgctc aatggcacag    104220
caagatattc caggctcatc cttccattat ccccattcct accctctccc caagaagccc    104280
tggttcctgc cagtgggaag tggccctcag aagccaaggt ctgagtgcta gatatgttca    104340
```

```
ttgcctctgg agcaccattg gtcccaggcc ttctcagtga tagaactagg gaagatatgg    104400
atgtacacac acaggtatgc acacacctct atctatagtt ctctatctac ctatacagtg    104460
aacactatga gctctccaaa accaactcca cagggctcat tctagttttt tttctttcca    104520
catctgtaac tcccttctcc aacagtgaga cgctggcttc tctcactccc aactcattta    104580
tctaccggac ctatacacct gaacagtgcc caactctgcc accatcccct ccccatgtgg    104640
atgccgtcct ctccctgctc cagctgcctc tgctgcatgc aggtcctcct cgttctgctc    104700
tggctctgat accctgcacc agatcagcct cctgtaagga tatctttctc atcccgttga    104760
ggcctccaca ccccacggca ggttgccccc tgaggaagcc cgtctctggt tcttgccctg    104820
ctcctgatca ccatggctcc tcccctaacc ccactgttgc cgtccccttt ctgtgcccag    104880
tatagtggct gtaggactaa attgtttaaa aagggtatca ttatttattt gagctttgtg    104940
aagccaagaa ctaggcttta agttttctg aattctgaag acatgcttag aaagaagaat    105000
caacaaaact ttatgaccaa atagaaaaag tgagagacca ggcagaattt tgtaattgat    105060
cctttcaaaa gatacaaact aaaggttccc ttggcaggga ggtagggcat ggggtggggt    105120
aggaggacta gtgacagctt aacatatgtt tgccaaccaa gaactgttta aaaagcaagt    105180
cgaatcagaa tcccagaccc tacgagctgg aggagcctgg ccccaccct cattttgcag    105240 agctggcagc aggtctgaga ggttaagtga cttgctctcc tcttctcttt ccgagatgaa    105300
ttattccgtg agtgctgggc tggtggtggg catcttcatc gggtttcaga agaaagccta    105360
cacttctcca gaaaaccttc ctgcccttgt ggcactgctc ctgctgtatg ggtaagccgt    105420 tgggccatt agctaatgcc tctgaagaga agcctggtgg tgggggtggg ggatcatctc    105480
ctgacagaaa acctgggctg tcctgtggtg gtagcaccca caagtttagc ttccggcccc    105540
aggtagggtc tgaagctgat aaccagggat ctgtctggct tctgattctg actccactga    105600
cagaggtatc tctgaggcct ggtcctgtca gtgacaatga gagaagtccc acatgatctg    105660
aatctcctac tcaaactgag gccttgacca aagcctgggg gcagccattc cccaaccccct    105720 cacccagctc tgactctcac tcatctgtgg ccaatctgtc cacctcagtg tccccatgtg    105780
aactggccaa gagttaccgc ccacagtaga agactccggc caaaaagctc ctcctgagtc    105840
agggacagag gatgacacag gggttacatc agcagagtta cagggcccag catgcaactt    105900 tcttcccac gtgtgtaaat ttgaatgagt aattcatcca tctcggcctc agttcctca    105960 tctgtaaaag aaaatagtga tcctggtcct tcctctgtgg gccagtagag ccttgccaaa    106020
gcattgttct ccacatcttt ctcttggaaa tagagaattt gggaaccaac ctgactataa    106080
gctgtgaaga tgagctcact gggctcatct gagatgacct cagctgggct ttgctgaccc    106140
aggctagagt gggaggtgtt gcaggctgga gaaccctcct atgaattgta cagggctttg    106200
tagtttacag agtatataca cagctagcag cccatttgct cctcacaaaa ccccatgaag    106260
tggtcaaggc aggcatcatt atctccattt aaagttgagg cacagagacc aacaaatgga    106320
gtatctctct ggtcccctgg gactctggcc agttcacaca catcacctca ggtgtaaggg    106380
gagtgcatta tatccagacg tattgtaggt ggaatggaat gtggaactcc atcactctga    106440
gttgtctcat ttcacacaga tgggcggtca ttcccatgat gtacccagca tccttcctgt    106500
ttgatgtccc cagcacagcc tatgtggctt tatcttgtgc taatctgttc atcggcatca    106560
acagcagtgc tattaccttc atcttggaat tatttgagaa taaccgggtg agcataactt    106620
tcttggcttt tttgtttgat tagtaggata gtagagtatg tgttggtcga gcagagccag    106680
gggcaagcat cgtacatgta gcagctgtat gcggatgagt gccactttct tcctccctac    106740
```

```
ccccgaccct gcctcctttc cttccttcct tcctcccatc cttccttcct ctttccttct 106800
tctcctcctt cctccctcct tccccgtcc ctccttcctt cctttttcat tgcttccttc 106860
cttccttcgt ccctccttcc cttctctttt ccttctgccc tctctcccct tttccttca 106920 tcctccctcc atccctccct ccatccttcc ttctttcttc cttctttcct tcctataagc 106980
acctttttca tttctgtgct ctgaatgaaa tggttttctg tgtttattct gcaagcaaaa 107040
cttgattctt gcaataaact ttaagctttg cttactcttt cagaaaggtt ttctcaggga 107100
ctttgggtgt tgggttttac acacacacac atcaatacat ttgggtaatt tcaaaatcta 107160
aaaggaacaa aaaggcatac aatgaaaaaa tctccttcct acccctgttt cccactcatg 107220
cagttctctt ctccagaggc aaactcttac ttgagtttcc tgtgtgctct ggagacacat 107280
cagcagatcc ctatacggtc tttctcccgc tttcttatgg aaattgtaac actctgacat 107340
atactattcc ttgggcaagt taatcttgat gaagagactg ggtgttctcc atgctgaatg 107400
cctcactttt atgagctgcc aagcccagtt gtcccttcca cctgacctcc ccctgtccag 107460
agacagatgg ccaaactgaa tcataaaaag agggggaaaa aagaaggca gtcgctgcag 107520 ggctgtcttt actccacact ccacactccc agtcccacc gctgtgtctg agtcctggct 107580
gtggctgtcc ttgaacatt tgcctcacca cgtgcctgtg tccccaggcg cctcaacctt 107640
tcctctcctc attagctctt cccagttcag agggtgggac cggccagcac atctgcactg 107700
ctgccctgcc acacccacct ccacctgcct ctgggcccca ctggggaaca caggacaaat 107760
ctgtgcggag gccccaccat gaaccgccca gacccgtgga cccctgagac tgactctttc 107820
cagatcttgt tagggtttcg tggctgctag gcaagtaacg aagcctcatc tgtcccatga 107880
atgataagaa attcagcatg tcagagtcag actctggaaa ggcgggggga taagaacaca 107940
gccccagcag atggccagag cacccaggtg actgaaagtg ctgctttgca gagctgtgtt 108000
tgccacaggc tcacagccca ctaagtctta agacagtttt ccttcagaat aattaaatag 108060
ccagcttaaa gcaactcaga acattttccc ctctgaggct gcacccattt agccaacatt 108120
tgctaagcac ccgccttcaa aaacctggta ttttcatgta aattatccga tacacagctg 108180
ctatggaaac ccccagtatc ccacaggaag ctccccagct cccagcagct gccggcccgt 108240
gtgagatcag gaggtcttta ccagctgaac accacgtgcc gggtgtgtgc tgatataaac 108300
aagcgtggcc cactcgtcct gccctccaga ggctcccgtt ccagtcggaa aaggacctgc 108360
ccacgaagtt tgcaacgata taagccacag tgtatgatcc tccataatac agcgtgtgac 108420
agagcagcag aggagcgagg cagataacat gctgcaggcc agaggcagcg ggaagagcca 108480
ggctgcaggg gctggggag ccgtggtgga ggaagttcaa tttcagcctg tagatttcta 108540
ttagcccatt taataaataa tgaagtgcct actctgagct aatcattgtg caggtattta 108600
ggaaggacaa aaaataatt aggactcagt gcccacccttc caggggccca ctgactagta 108660
gagaaagtag gcagattttt aaaaaattaa tcatgggaat gtgataagtg ctgggagaga 108720
ggaatggata ctttctcatg ggaatcttgg aaggcttgta agggaaggca ctctctgagc 108780
cagctgtcta aagaagaaca ggaatcttta agaaagcaga agggaaaaga gcattctttc 108840
ctgcttggag caataggtaa cagcctgcac atgcccaggc ctagaggcca aagagcacag 108900
tgattccaga aagagtgggg agaaagggta ggcagggaag gatgaggtaa tgtgggcgca 108960
ggtgtggagg ctggagaggg aggaggttgt gggactggga ggagccagat ggaatggaca 109020
gcagtggccc agccaggagc tatgctggcc tcgtacgcct cgatgtccct tctatttct 109080
```

```
caggggaggc tctgcccaac atgccaagtc cgaccacttg aaaacaagtc cctggcttaa   109140
cacagacccc agagagagtc tccaaccctc ctctccctag acaatggtag ttgccctgtg   109200
aggggctgaa aagcagagct ggagatggct cagggcctgg tgttaacaaa tgccttgagg   109260
gctcctgttg tttcaaagtg agtctgcagg gagagctccc taagtggaca gcaggagggc   109320
tgcagcttct ctgcacattc ctgctgtcac ccccagagtc acctagggga ggggtaagga   109380
cagtaatgca ggttcctcac agttagcctc ggtgcccaca tggtactgag catagtaaat   109440
gtttagaaga tgctgcctgg ctagacaaag gggaagctcc cgcccactag aaacttgcag   109500
ggagccccag tccttgattg gtcatttaat tgattagctc cttggcctgg ccttgaggca   109560
ctgcttgtaa gtacttcatg acctccattg caaacccatg atgctctgct ggacaaatcc   109620
ctccagtggc cagtctggct gcaaggactc tctgtctgca ggccttgccc tgtgctgtcc   109680
tgtgagagca tctgggcccc acctgctgaa gagaggggg gtgggg tttg cccgtttcc   109740 aacagtccta cttctctgtt tcagacgctg ctcaggttca acgccgtgct gaggaagctg   109800
ctcattgtct tcccccactt ctgcctgggc cggggcctca ttgaccttgc actgagccag   109860
gctgtgacag atgtctatgc ccggtttggt gggtggtagc cgaggcccat ggagcatggg   109920
ccctgggtcc aaagctggga gggttaccgg ggggctcct gcatcagact gtggcagggg   109980
ctggtgctag gaggggacct tgttgggctg gaggtgtcct gccagctgga gaggattagg   110040
gtgcctctgt ttccatggct ggggagccac aggagggatg gagggcagcc ttatgaggc   110100 gggtgtttgg ctcttgctca gttcccacat aaggcctggt ctagtgggcc ctgtgctgtg   110160
gccaggtctg tggggtgagc tggggcggct gaagtggact caattcctgt tgatgccag   110220 gtgaggagca ctctgcaaat ccgttccact gggacctgat tgggaagaac ctgtttgcca   110280
tggtggtgga aggggtggtg tacttcctcc tgaccctgct ggtccagcgc cacttcttcc   110340
tctcccaatg gtacgtccat gccacaccct gggccagtgg gcagctcagg gcatccagaa   110400 ctggaccta tacccacatg gtcatttctt cctcaggag ccccactcca caatgttttt   110460
tctacattct caaagcctgg cttttctcca ataatacaag tagaggatcg ggttaaaata   110520
ggcacattca aatatgtgaa gagcatccac tttaaaatat ttaaaatgca gtgctattaa   110580
tttcaattgc tgatatttaa tccttctcat ttaattacca aatgtgtatt ttgattagat   110640
gatagtattg caaataacaa tggttacagg gtatccaaag tactaggaaa tagactaatg   110700 tattatgag agaaaggaca cagcaggccc ctttgctaat tagagatttg ggagcatggg   110760
agtaatatgg gagccatgtg gaggggtgcg ggcagtgatc acgacccccc actcctggag   110820
gaaggtgggt agctgccaac cctgactttt gaccagggct tctcaaatgc caggttagct   110880
ggcaattgcc attcttccgc aggctcttcc tgaagctggg tgggccctg cctcactccc   110940 ctctgcaatc cagtcctacc tttattgtcc tcacccaggg gcctgaattg ccaagcagca   111000
gcccttccta gcaagctttc cccaatagtg ttttgtttct taacttttcc tcctctcagg   111060
ctgagtgtgg tcacctgtaa atagattcca aggacttggt tttatgtttt gatccacagg   111120
gaattgattt attggaaatg aatctgcctt tctactcaca ggactgtgag aggtgaatga   111180
gatcacaggt gtcaacacac gcctgatgaa acaggataca caagcagttc tagttatggg   111240
agacagtgtc aggaattgtt gtccttggca ccctcagccc ctgcagaccc tttctgcagc   111300
cttggccata ccttttagag gcttttgtgt gggagagagc aggtcaggag ttgactacc   111360 caaattgact cattagcttc aaactctgat gtcaacacat ttgaatgagt cctgcctgct   111420
ttagggccta agaggacca gagaagtaca ccatagtccc tggcttccag aaggtcaggg   111480
```

```
agggtttcaa agaagaggct gtgtctttaa gaatggggaa gattccattt ggtggggcag   111540
gaggaggaga acattgaggg actggaaaca catgcggagg ctgggagacg ggaatgacca   111600
ataggactgg gaaccagggg gagatgccaa ttgctgacag aggagttagt gcaagaggta   111660
agtgagaagg gtaggtgggg ctggattgca gggctgtaac tacagctgca gagggagggc   111720
ttcaacctac agctgatggg gaacaacaga aggttttgag gcatgaggtg gcctgatgac   111780
aactctgttt tggaaaggtg gagttggcag ggcagactgg aggaagtggg aggctcgag   111840 gttagtaact acccccttact gagtgcttgc tgtagaggaa gcattttagt cctgacggtg   111900
atcccaggcc ctgagtcttt actctgtgcc aggcactgtg ctgagttcat cttcagcaca   111960
atcctatgag acaggtattg ttaccctcct cctcatcaca tggttgaagt aggcaaggtt   112020
cagagaggtc caatgcccaa gatcacacat gaggaggcca ggactggaac ccaaggctga   112080
ctctggacat gagcacctga cctctctacc taatgcctaa tgcctctcct gctgggagcc   112140 cttttttagaa tttaagtctt aaaggatgga agcccagaag gaagcagaag caaggaagtg   112200
gaagagaggt cccatggaaa ggacagtgcc aaggacactg tacagccagc ccaatcctga   112260 cccctttttct tcatctagga ttgccgagcc cactaaggag cccattgttg atgaagatga   112320
tgatgtggct gaagaaagac aaagaattat tactggtgga aataaaactg acatcttaag   112380
gctacatgaa ctaaccaagg taagggaatg ggtatgagtt tggaggtgct ggttagatcc   112440
acagttggca tgatgttgcc attttccttc tatagaacaa ttgatatgct tatgcaagca   112500
atttggttcc cagttttatg tagggtcatc atccctgtgt tataactcgt cttccaagag   112560
catctaattc caatgtgtgt tccctgctat tcatctcggg cactgacaca gggcctcagt   112620
gagaatcact ccagctgagc atcattccct tttctgtgtt ctgtttctgc agagcatggg   112680
tcagcctcga gatgtctcag tactcaccac acctctgtgc ctgcccatgt caatatgtaa   112740
cctcctagtg ctggtagttt tctcctaaac catcctttgc tctttgttcc ctcttcccct   112800
ccttgctctc accctgtctc agttctcagt ccggtttctt cgtatcttgc agatttatcc   112860
aggcacctcc agcccagcag tggacaggct gtgtgtcgga gttcgccctg gagaggtggg   112920
tactctgcag accacgtgtg aaaggcttcc gaacatcagc tcttgtgcct gcctctcctc   112980
cccataaggc agagctattc aataggaaca taatgccata atgcaagtca catatgtaat   113040
tttaaatctt ccactagcca catgagaaaa gtaaaaagaa aataggtaaa attaatttca   113100
ttagtatttt ttattttact caatataacc aaaatattat ttcaaaatgt aattaataga   113160
aaaccttatt aatgaaatat ttgacaattt ctcgttgttt ttaagtcttt gaatctttac   113220
actcagggcc cgtgtcaact gggacttaga tgtgtttcaa gtgcttagta gccacatatg   113280
gctcgtggcc tctgatggca gcccaggtct aaaattcctc cccagctca cacacacact   113340 taccctgggg cctgacattt tagaccttct tgatctctag ggccaggcta gctctgtgtt   113400
ttctcctagt gctttggcct cctgggagtg aatggtgccg gcaaaacaac cacattcaag   113460
atgctcactg gggacaccac agtgacctca ggggatgcca ccgtagcagg caagaggtga   113520
gtatcctgct cctcctgtct cagggagtct ctcacaggtc ctgtgagaag aataggaagg   113580
gtgatcatca gacccctatag tagggtggct ctgaggccct gaaagatctg tacagagaag   113640
gaggcctccc agagagcatg gcccaaaaag cccaacacat agacccaatg gaaaagtgaa   113700
ctgaattgtg atagttaaga gattcctctg ttgggatgga ttcttggaaa gacctgggaa   113760
gcactaagtg tgtggttctt aatctcttag aggtcacgga acctttttaag catctgatga   113820
```

```
atatttgtag cctattccta taaaaatgca ccattgcttc ccattacctc cctccacaca    113880
tttttacaaa acgtttcagg gagtttactg agcccccagt cacatttatg atcctgcagg    113940
agctcttgaa tcccaggtta agaaccccctg tgatgaatga agaatccttc ctctgggttg    114000
agtttctaga taggggctca tgcatgggcc tttggggtag cctaacctgc attggctatt    114060
tgtaggctga tatttggctt tgccagacca aggagcatag agggaaaact ggcgtgtgcc    114120
cttggattct ggagggtgac tgctgctctc tgtaataaaa tgtgtttaaa cagactggtc    114180
ccctatgggc aggacagaga ggatgagctc tcactcatct gcctctttcc tggctgcagg    114240
aaaagcttga acagtaaaac ttcagcacac acaatagagg tgcccagagg aagcctctgc    114300
cctggtttat aagtggagtt aggtgctgct gacatctgtc cagcatctgc ttgactgggg    114360
cctcttcctc tctcctgaaa gccatcctca gcatggccca atgcccagtg ggcaggacga    114420
gtcctgagca cgcttcactg gctcagacag gatgaatttg attctttggc ctccatagcc    114480
agccctactg ggtttacaga aaagggacag gcaggggtga agccaggtca tggctgagtc    114540
catctcaaca gatccagctt cacctgcaag tgaccacgca ggtgacttcc tcatggtgac    114600
aaaaggagtc atggcagggt agagatatca taccatggca ggggaaagat atcatagaat    114660
tttccatgag cacatttatg agacatcaag ttacaactgt gtccaagtga ggcacagtct    114720
gacatccaga aggtaaaact gagctggacg ctagaaagaa actataggct aagacacag     114780 aattgggatt atatggtagg gtagctccca ctaatttgga aacgtaccct acttgcttcc    114840
ctgagtagtt ttaattggcc cagccatgcc tttggtggct tttgtcattg tggggaactg    114900
taatggtctc tctgtaccat cctatatcat ccatccttta ttcatagacc ctaagctata    114960
agaagaaaag gatgagatta gactaaatgt ctatgtatag tttatttttcc atcttggcaa    115020 tatatttttt agtgggggtg aatatattag ccaaagggag ttggtggaac ccaactcact    115080 ctaccccctgc tccctgcagg cctctcgctg tgggtagtta tctgactggc tcctctttca    115140
ttgctatctt tgccaataaa tacagataga gaagtttact tccatcggga cacatgcatc    115200
ttttctagtt acttcccaaa tgtctgaaaa ttattgataa atcatgaatc attttcttaa    115260
acctgatctt ccctctgttt ttaaactcac atgtgaggtg atctgatcca aaatgaaagc    115320
tgacttttgg cgtaacaggg attcaattaa tcctagacat ggaaacatgg aagaatctga    115380
caggattcag tttctaaccg aagggcccct gttttgattc ccaaatatcc catgcatttc    115440
tgaagccaaa taggagaaga gaagaagcag cttccttttc ccgttggcag aagcttctcc    115500
agccctagct ctatggtcat ccctccactc cttgaaggat actcagtaat tgcttttttt    115560
cttgcagtat tttaaccaat atttctgaag tccatcaaaa tatgggctac tgtcctcagt    115620
ttgatgcaat tgatgagctg ctcacaggac gagaacatct ttacctttat gcccggcttc    115680
gaggtgtacc agcagaagaa atcgaaaagg tgaaaaatgt tttgttgtgg ccacatagga    115740
gtctggttaa ttacaagcct gtttcatgag agtgcattct cttggagatg agaaactgaa    115800
gcgtgctatt cattcattca ttccaacaaa tgtttactat gtgtctactg tgtgccaagt    115860
actgttctag aaaccaggag tatagcagtg aacaagacag acaaaaaaaa atccccactc    115920
tcatatctaa caaaatgttg tatgcattta tcctctgact cagcaatcac acgtctaaga    115980
gtttatcctg aagatgcatc tcccacagtg caaaatgaat atgtataagg tgatccattg    116040
catttgtaat tgcaaaatgc tggaagttac ctaaatgttt agtcattgta gattggctga    116100
ataatttatg gtacagacac acaataaagt cttacgcaac tataaaaaag aagaagaaaa    116160
gtctcagtaa actgatatgg agatatttcc agtaaatact gttaaatgat aaaaagcaaa    116220
```

```
gtggaaaaca gaacatagag aacgctactt tgtatgtaag aaagaaggaa aaacaagaaa  116280
gtaaacgtat gtctgcttac ctttgcaaat agaacgtaga aaggataaac cagaaaacaa  116340
tgaatttggt gatcaacaag aagaaaatgg gaagaaagaa aaatgggagg aaacagtact  116400
tctggggata tattttttgta tagttttaat ttttggaagc atgttaatgt tccacatatt  116460
caaaaaaaat cagtaagaat gggaagtagg caaaaatgaa aacaaaaaga aaacctaaca  116520
ctgacagcaa actaaataaa gtaacccaat tttatttcaa ataaatatca taatcttgca  116580 aaaggggat agagctaaca caaacaactg ctgaacacag tgtttgactc tatatcctca  116640
ttcttgggca gggtggagcg ggggagaaga actacaaata atttctgagt tcttttttagt  116700 ttgtttttta tagtggtata ggcaaagtga ttctgaaaat tttagatgtg ttacaggatt  116760
aaataaatta ataaatgttt tgatgttatt gggacccaga attctcaccg tggaagaagg  116820
gacttacaaa tatggaaaag ggaaaagcaa gaaagaactg tgaggtcatg gataggaacc  116880
ggaggtagca ctgggaattc aggaatattt atatgcttgt gtttgtgggt gcatgcagat  116940
gtgttcatgt ttcatgcaca taggcatgta tatatagaca tatatttgca tgtgtgtatc  117000
tgtcttccga aaggctcaag aagcaaaaac accccagtag ccatgagcac acttagcact  117060
caggcttttg tcttaataac attccccact aaaagtaacc ctgattcctc caataaatga  117120
taagttccag ggctggaatg gcataggtat aaaatgaacc tggaatatct tatgccagaa  117180
agtaaggaag tgcttttaaa aaaaaaataa ggggctgggc atggtggctc acacctgtaa  117240
tcgcagcact ttgggaggcc aaggtaggaa gatcgcttga gcccaggagt tccagattag  117300
cctgtgcaac atagggagac cctgtctcta caaaaaatta gcaaacaaat tagctgggcc  117360
tggtggtgca cgcctatagt cccagctact caggtggctg aggtgggagg aatgcttgag  117420
cccaggaggt tgaggctgca gtgagctgtg atcaagccac tgctctccag cctgggaaac  117480
agagcaagac tctgtctctt aaaataataa taatataatt ttaaagaaat aaaagtaact  117540
ctgtacagat tgcttattgg ttacatggga gaaacataat aatttacaa tggagaaatt  117600 agacagcacc ttaactgggt gatcaaaatt aaccataagg ggcagatgga catctcatgc  117660
cccgagatgt gatacctgt gaaggacaca atttcactta tgtagaatcc agattggaga  117720
tatgtaacct gaatcttatc atgaggaaac atctgacaag ctccaaagaa ggaatattcc  117780
ttaaaaaaaa aaaaggaga ctgtattctt caaaaacata agagtcataa aagacaaaga  117840
aagagctatg gaaatatctc tgatcgcagg aggctaaaca ggcataatga ctgaatagca  117900
gacaatagac tacatcttgt gcagaagaga aaaaaaatga tagaaggata ttattggacc  117960
aactgacaaa actgaactat gaacagtaga ttaggtaaat gtatcataac attaagttta  118020
ctgacattga taatgtactg tggttatgta agagaagatc tctattctta ggaaatatgc  118080
cctgaagtat ttaggagtga agggctgtga tgagtaattt accctcaaat gggtcacaaa  118140
aaattgtgtg tgagagagag aagggttta ttagttaata attctatgaa ctattttat  118200 tcctatatgt ttgtgtgagt ttgaaactat ttccaaataa aaagttaaaa atggagatta  118260
cattctagtg ggagggatag acgatctgta gataaatagg taaatatcc agtacattag  118320 agagtgaaaa gtcctcaggg aaaagtaacg cagggaggaa ctgctgggc agggtttgca  118380 ttttgaggta gggtggccca gggagagcct gcagaggaga gaacctgaat gaagaactag  118440
aggtgagaga aggagccacg tgcacaccta gggaggaaca ttccaggcac gggggactag  118500
tatagaaggc agaagcatgg tgagcttgtc tccagtggct tccctagatc ccctcctgcg  118560
```

-continued

```
catgtgcaca cacacctggt gtctctgtca tcgttccctc acagcactgt cacgatctgc    118620
cagtattctg tttattttga ctgccacctc cccgcagtct gaggatagca gcaatggctg    118680
tgttcacatt gttctccagt gcctggttca gtgcctggcg tatggtcagt gctccatagg    118740
tatgtgtcgg atgcacaagg ctttgggtgt aaccctcttg acgggtggga tcaacaggtc    118800
tgggactcac catcttctca aacagagcct tcctcctcca ctgctagcca tggtccagga    118860
cgctgggcga gacccactgt cttgctcttt gtaaggctga agtccatttc ccaggcggct    118920
acacccaaca gatgctgagc aggctgggcc accctgggat ccaagacaca gagagaaaga    118980
gccctgtct ggcgcctgaa gcacatgcca gaggacagga gccagcagga gcctgtttca    119040
gcctagctgg ggatttcatt ctggaggcgt gagatctggg agcccaaggc tttgaactgg    119100
gggaggtttg gggtgtttgc ttgtcttctc caaatggcat ttctttctct tccctaggtt    119160
gcaaactgga gtattaagag cctgggcctg actgtctacg ccgactgcct ggctggcacg    119220
tacagtgggg gcaacaagcg gaaactctcc acagccatcg cactcattgg ctgcccaccg    119280
ctggtgctgc tggtaactgc gggcttgggc cgcaccaagg gcttaaacca agtgctgggt    119340
ctcttgggtt ggggaaatag gttctgggtc ggcagattta gaaactgcag cagtttggct    119400
ttagtctgga ctgtttcctg tgttgctcat tttgagcgat cagcccagtg tttggttcac    119460
acagctccgg agaaaaacaa gtcacggcac agccttgact tgggactgcg cacatcctgc    119520
gttcccagga tgtctcctgt ggggccatcg gctcacagcc gggaagttca gcccactctg    119580
cggcctgtcg gtgtctggtc cccatacagg agcactgagc tgggtcaaag gctcctgagc    119640
tgagccaggc caggcctgag gccatgccca cgcagcccaa ggatcatgag ggcacaggac    119700
atagcgggaa ccaaggaagt gacctgagtg acctccctgc cttctgacaa atgtatttgc    119760
aggattttct tttttttgagg agaattctgt cattgcctta atccacttta atcccctcgt    119820
gggctgaaat gggcccagga tggacgccac gcttctttac tcttggatcc acctcctgcc    119880
ttccctaccc tacaccaggg taccctgtc ttgctcaagt gaggggagtg actgtgtgcg    119940
ccttctgtca gctcatcctc cacaggggag ccagcccagg gggaagcagt aatcagaagg    120000
gccagctccc agcctgtgcc cccaaccttc tctccacccc ccaggatgag cccaccacag    120060
ggatggaccc ccaggcacgc cgcatgctgt ggaacgtcat cgtgagcatc atcagagaag    120120
ggagggctgt ggtcctcaca tcccacaggc aagagattcc cagggctggg gaaggtgggt    120180
gggaatcctc tcctgctcac ctcctctctc ctgccccaca gcatggaaga atgtgaggca    120240
ctgtgtaccc ggctggccat catggtaaag ggcgcctttc gatgtatggg caccattcag    120300
catctcaagt ccaagtaagc agatggtggg gcgtgcccct tgttgccttc tgtggatcca    120360
cctggatcct gtgttctcca ttgacacttg aagagtcct gctgctccgt catccctggg    120420
ggcagaggca ggtggtggct gggcctcatt ctccagcagc agatggagaa ggccatcatg    120480
ctgataagaa actcctctat attggcctaa tttcctgtgg tcgaagactc gcccaagtct    120540
ctggatgggg catctgatca ggatgcatgc agagcctggc tgggatgagg gagggctgct    120600
accactgcct caatatttca ccacttatct caacagatcc gggacctgtg gcctatttac    120660
taagagtcca ctccaatgta ggaatggtta ggagaccaac tgacttgagg acccatcttt    120720
gttttagaa tattgtatgc ttttgagttt gaaaaagac catatgttat atgacaaacc    120780
aacaatggca gtaatcttga ataggattat ccttatcctg tacccacaca ttgtaaacta    120840
ttgtagataa ttccttatta ttaagagttt gcatgccaaa gctaacagtt taagattatc    120900
agcatattgc cgtgctcatt cacgttctga tatgctttat aacctagaaa agagcagagt    120960
```

```
tacaattact catttattta acaaacactt attaagagct cagaatataa gtcactaagc   121020
tggttggtgg gaggaacagc acataaccca ccttatctat gctgaggtgc ataatcctga   121080
tgcacccaca ggagggtgtt acacagaaga tgtcatcctt tcatatgtgt cagagcagat   121140
aaataattga gagaaaggtc taatagatta gctgcttgtg gcaagtggac gtttgaccca   121200
tgatttattg agcaactaca acttggacac tgcatagata tctatagaaa tagcagcatg   121260
tcaggtcacc agacctgtgt cagcaacttc ctgtgtccaa ctgctggaga aagggaagtc   121320
tcctattcct ttccctccag ctccttaata tctccatgat agaggggtg agagggagt    121380 gttccctgtg tggagggatg gtgagttttc tggagctgaa aggtaaacag cctttctcct   121440
ctgcatctta ctgcagagga gaacagccct agactgtgga ggaagctttg gagtcagtta   121500
tgactgacac aggataccag ggcataggt  actgacaccc gctagccgtg cacacactct   121560
ctggtggacc atcactcatc aagagaggg taaccagcca tcctgctgaa ggagaaagaa    121620
agcaccaatg gcccaagccc tagcagctcc attgtttcag gaagcttcct cagggaagtg   121680
ctgccttccc gagcctttgc tcccacctgg cccatcagcc cttaccacca ctcagtatgc   121740
actggtccac gtgtctttat gggcagtctt gggatcccca cactgggcta aaactacctt   121800
tgacggccag gtgcagtggc ttacacctgt aatcctatca ctttgggaag ctgaggcagg   121860
tggatcactt gaggtcagga gttcgagacc agcctggcca acacggtgaa accctgtctc   121920
tactaaaaat acaaaaatta gatgggcatg gtggtatgca cctgtaatcc cacctactcg   121980
ggaaactgag gcacaagaat tgcttgaact cagaaggcag aggttgcagt gaatcgagat   122040
cacaccactg cactccagcc tgggtgaaac agcaagactc tgtctcaaaa aataaaatag   122100
gctgggcgtg gtggctcatg cctgtaatcc cagcactttg ggaggccaag gcgggcggat   122160
cacttgaggt caggagttta agaccagcct ggccaacata gtgaaaccct gtctctacta   122220
aaaatacaaa aaaaaaaaaa aaaattagcc gagtgtggtg gcaggtgcct gtagttccag   122280
cctctcagga gactgaggca ggagaattgc ttgaacccag gaggcggagg ttgcagtgag   122340
ccaagatcat gccactgtac tccagcctgg gcaacggtga gactgtctca aataaaataa   122400
aataaaataa aataaaataa aataaaataa aataaataaa ataaaataaa taaaactacc   122460
tttgacttca gcaagtacga ttatcccaca ttaccatgca gacatttgat ctctaaaaac   122520
tggtatcaaa tgatttctcc agggactacc atggttttc  tctcctagtt ttcagtatgt   122580
acacaggtct atggtatggg cctttaatcc ccagtatttc ttttttttgtt gttcttgttt   122640 gggtttgttt cttgttttc  ggtttttttg agacagggtc tcactctgtc acccaggctg   122700
gagtgcagtg gcatgatcat ggctcactgt agccttgacc tcctatgctc aagtgatcct   122760
cccgcctcag cctcccaagt agctgggacc acaggcatgt gccaccatgc cctgctaatt   122820
ttcgtagaga cagggtcttt cttgttgccc aggcttatct tacattcctg agctcaagtg   122880
atcctcccac ctctacctcc caaattgctg ggatttcagg tgtgagccac caagctgagc   122940
ttaatcccca aaatttctga tgagtctact ccttattttg ggattacctt aggcccaacc   123000
actaacagag gcctgtcctg cactgtgtgc atccctaga  tttggagatg gctatatcgt   123060
cacaatgaag atcaaatccc cgaaggacga cctgcttcct gacctgaacc ctgtggagca   123120
gttcttccag gggaacttcc caggcagtgt gcagagggag aggcactaca acatgctcca   123180
gttccaggtc tcctcctcct ccctggcgag gatcttccag ctcctcctct cccacaagga   123240
cagcctgctc atcgaggagt actcagtcac acagaccaca ctggaccagg caagttggcc   123300
```

```
ctggggcacc gagagctgag caaagactgg tccagaacac ccagtgtggg ttggaattgc    123360
cataagaggg aggcataaca ttcccgattt ttaacaaact cttgccctct gtttattggg    123420
gtaaaagctg atatatcaga aattgttttc taacaatatt ttttagtcat caggaaactt    123480
cattgattct ttttttaca ttttccttcc ctgtgatgct atggtgtgtt atttcattct    123540
tgctcgtttg tggtggtggt ttttccttca aatcagcttt attgatgtgt aattaacata    123600
cgatgaaaca caggttcttt gggaggccaa ggcaggagga tcacttgagc ccaggagttt    123660
aagacaggcc catgtaacaa agtgagactt tgtctctaca gaaaaaaaaa aaaaaatca    123720 gaaaattagc caggcgtggt ggtgcatgcc tgtggtccca tctacatggg aggttgagga    123780
aggaagattg ctggagccca ggaggtcaag gctgcaatga gctgtgttca taccactgca    123840
ctctagtctg ggtgacagag caagcccctg tctcaaaaaa gcaaacaaa acaaaaacac    123900 ctattttaaa tgtacagttt agtgagtttt gataaacgtg cattccatgt gtggttttta    123960
aaaatgtaat cacatttttt attgcggtaa aatataataa cataaaattg accatgccaa    124020
ccatgtttaa gtgcacagtg cagtggcact aagtacattt acattgttgt gcaaccgtta    124080
ccaccatccc cgatagaact cttccatctt gcttcagtga aaatctgtgc ccattaaaca    124140
ctaactcacc acttactgcc cccctcgccc ttggcaacta ctgttctact ttctgtctct    124200
aaggctctga ctactataga tacctcatat aagtggaatc atacagtgtt tgtccttttg    124260
tgtctggctt attatgcgag gacttagcat aatgtcctca aggttcatcc gtgttgtatc    124320
atgtgccaga atttccttcc ttttcaggc cgaataatat tcctttgtac gtatatgtgc    124380
tacattttgt tcatccatct attcattcat tgatagacat ttgggttgtt tctgggtttt    124440
gtgtttttat atatgttttt ttaaaaataa acatctttag agacagttca gtaaagcagt    124500
ggaaacaggg aagtctccat ttaacccctg aggatctggc tcacctgcac cttctcatca    124560
gcattaagca gagggaggca cgagcaggag ccacctgcac actcaatgag gagctgaaca    124620
gggatcaatt accttttttt ttagttatta ggatgctgct agctgagaat ctgccttgcc    124680
ttgattaccc caatgtctgg tgcccaagtc ccttgagtcc tccagcagga actcctgtgg    124740
catcactcag gagtctagtc taagaagcta gctctgacca gggcagtggt ggccaggctt    124800
ctgtgagtgg gccagcctcc cccgggtagg acacaagcca taccagcagg gctgtatgtg    124860
aactgtggaa aatagagagc aaagtgggta ggtgggtgta gggtgctgtt ttcctggaaa    124920
tatctaccta atctcgctct tctcttacct ctaggtgttt gtaaattttg ctaaacagca    124980
gactgaaagt catgacctcc ctctgcaccc tcgagctgct ggagccagtc gacaagccca    125040
ggtacccctg ctgcttatgc agtccacagc ttgaggcagt tccttggctc agagcccagc    125100
tggttcactg ggcttgagtt gctccaaggc tcagatatgc ctcctacaga gagccccacc    125160
cacaccacgg tccctaccaa gtccccacca catcctcatc acatccttgc taagtccctg    125220
ccactgtgtg ttctgtgctg aagaactttt cattcagtag ttgtaggggt tcctattgta    125280
atcaggaaac catctggata gcatgggaga gcattttga aaagaacttt cccatgtttt    125340
tgcttacagc aaaaaagctt ggatttgggg aataaggagc agagaaggta atagagaata    125400
ttagaatgtt ttgggtgctt gacatctatg tctggacatg tgtttgagtt tcaagggaag    125460
ggacttaact ggcacatcat ttcagtgtca gacacatttg gttagatcaa ggaatagcat    125520
ctgttgtagg aagagggctc tttgttcttt ataaaaatta caagaagatg gagaaagaag    125580
caataggagg tatgtctcct ggcttgtgat aactcttgga ataggtgctt gtaggttcct    125640
gccctggcac agtgccccat gtaaggagca caccacccaa gaaggagaga gctagagcaa    125700
```

```
gtactggagg aggcaccagc atcccaatgc cttggcttaa gcctgggatt gtagagggat   125760
gaattagcca ctctcttctg acttacctgg agagtaaatc aaatcaaatc aagaagcaag   125820
gatatgcaaa aaccttattt ccccataaag ttttttattct gcccagtttc tggattgcaa   125880
gaaaaaccaa atacagctaa tgattgaaac actgctgtct aaagcagtgc ttgtgatgaa   125940 tttttttccct tcctcttgac cagcagagac ctaatggcta cttggcaaaa ctgactttgt   126000
cttcccaccc cttacctgcc agagggccca gaaatgccta aggctccttt agttacagaa   126060
agtttgcttt tactgagatc ttccagccac tgattcccat ttatagatct ggtgattgct   126120
gttgacatca gttgaaaatt attttttaaaa accacttgca gttgcaaatc cttttttataa   126180 ctctgtaact cagaatatag aattgggtag caaaattgtt tcccagaatt accaatggtc   126240
tccccacccc tgcctggcat gttccctctt aaaggactaa tcccaccaca tcacctctgg   126300
gccaggcaga acatcagggg tgctgatgtt ctgtgatcta cagcagttaa ttccaaactt   126360 ttctcccctta ttggatgaga tcatttttct attgtgtttt ttacattttt gttcacaaag   126420
attagaaaac ctgcaacaca cttattggca tattttctg ataattttca tccaaaacct   126480
aattctgact ttacaacata ctatctttac aaaggtttgc aaaaattctt tcatatagca   126540
ttgtatatgt ctgtcatgaa ataatagtaa gtatattatt gtttacatta taccacttca   126600
aaataatttc ctttaaagta ttcttcaaac aagaaaaagg caatttctct caagaagttt   126660
tagagagaat ttacaacttg ctcctaagca aatgtgagaa cttcaggagg ttcatctggc   126720
cattggcttt acaactccaa attgtgagcc aggaccacac agatatttct ctagaaatca   126780
gcgtttgctt accaagaaca ttttttactct ccaaaggact ccatcctgga aaacatgttt   126840
tgggataagg tcttatgcaa tcttatactc tgttattaaa accagtgagg gtcaaggtgt   126900
taatagatta agtagtgaca gatgatcaga caacttagaa acatcctaaa taggttaata   126960
attatgtgac catcgcatgt gcattcccaa attaggaaca actcagatca atttctaatc   127020
cttattctta cactgttcca gttccccat ataactcgta tctttgtgtt agtttcagaa   127080
gtttctgaag taccctcagc cttgatgggg atcctcgcac cacctcaaat cctgttctca   127140
gccctaagaa ctgtgttagt catcctctta agaggatgtg tgattttaaa tcagataatg   127200
ggataaacca catttcgtct agactggtca ggcctttgtc cagtcccctc ctcgcccaca   127260
ctaccccagc tccacagcgg gcattggttc aggaattcaa cccacacttt ataactggag   127320
acagtatctc tccagttaaa aaggtcacct tggtgtccgc ttctcaagga acatggacat   127380 cttttattaat caaagcccaa gctttgatct ggagcctaat atcctgcact ccagctctca   127440
tctctcccct cccccagtca cactttcatg cttcccagag ccaccctac aggaagtggt   127500 caagggaatt ctatacctca gggctgacct aaattaggat ttcttggctt taagataat   127560 ggtaactttc ttaagctaaa aaagccccaa aagaccctgt aagagccctt ggaaacagca   127620
ccatgggtgt agcttccccc caggatgtaa gcatgtatgc acacatctcg tatgtgtgtc   127680
tttgtaacaa atgcctggat cttagtacca gggagacctg attcatagat ttcatagaga   127740
aggagagaaa gatggcccat aacctgggtg atctgacaga atcacagtgc cctcagctga   127800
gtgcccttca gaaattgatt gacaactgtt tagcttttga aatctaaaag tagtacagca   127860
tctcagaaaa ccaagatgac gcgagtccat gtgatctcct tccacaggac tgatctttca   127920
caccgctcgt tcctgcagcc agaaaggaac tctgggcagc tggagcgca ggagcctgtg   127980 cccatatggt catccaaatg gactggccag cgtaaatgac cccactgcag cagaaaacaa   128040
```

```
acacacgagg agcatgcagc gaattcagaa agaggtcttt cagaaggaaa ccgaaactga    128100
cttgctcacc tggaacacct gatggtgaaa ccaaacaaat acaaaatcct tctccagacc    128160
ccagaactag aaaccccggg ccatcccact agcagctttg cctccatat tgctctcatt     128220 tcaagcagat ctgcttttct gcatgttttgt ctgtgtgtct gcgttgtgtg tgattttcat    128280
ggaaaaataa aatgcaaatg cactcatcac aa                                  128312
```

<210> SEQ ID NO 2
<211> LENGTH: 7326
<212> TYPE: RNA
<213> ORGANISM: Homo sapiens

<400> SEQUENCE: 2

```
aggacacagc guccggagcc agaggcgcuc uuaacggcgu uuaugaccuu ugcugucuga       60
ggggccucag cucugaccaa ucuggucuuc gugaguggcau uagcaugggc uucgugagac     120
agauacagcu uuugcucugg aagaacugga cccugcggaa aaggcaaaag auucgcuuug     180 uggugaacu cguguggccu uuaucuuuau uucggucuu gaucgguua aggaaugcca       240 acccgcucua cagccaucau gaaugccauu uccccaacaa ggcgaugccc ucagcaggaa    300
ugcugccgug gcuccagggg aucuucgca augugaacaa ucccguuuu caaagcccca    360 ccccaggaga aucuccugga auugugucaa acuauaacaa ucccaucuug gcaagggau     420 aucgagauuu ucaagaacuc cucaugaaug caccagagag ccagcaccuu ggccguauuu   480
ggacagagcu acacaucuug ucccaauuca uggacacccu ccggacucac ccggagagaa    540
uugcaggaag aggaauacga auaagggaua ucuugaaaga ugaagaaaca cugacacuau    600
uucucauuaa aaacaucggc cugucugacu caguggucua ccuucugauc aacucucaag    660
uccguccaga gcaguucgcu cauggagucc cggaccuggc gcugaaggac aucgccugca    720
gcgaggcccu ccuggagcgc uucaucaucu ucagccagag acgcgggca aagacggguc    780 gcuaugcccu guguucccuc ucccagggca cccuacagug gauagaagac acucuguaug    840
ccaacgugga cuucuucaag cucuucccgug ugcuucccac acuccuagac agccguucuc    900
aagguaucaa ucuagaaucu uggggaggaa uauuaucuga ugucacca agaaauucaag      960 aguuuauccaa ucgggccgagu augcaggacu ugcuguggguu gaccaggccc ucaugcaga   1020 auggugugucc agagaccuuu acaaagcuga ugggcauccu gucugaccuc ugugguggcu   1080
accccgaggg aggugugcucu cgggugcucu ccuucaacug guagugaagac aauaacuaua    1140 aggccuuucu ggggauugac uccacaagga aggauccuau cuauucuuau gacagaagaa    1200 caacauccu uuguaaugca uugauccaga gccuggaguc aaauccuuua ccaaaaaucg    1260 cuuggaggggc ggcaaagccu uugcugaugg gaaaaaaucc uguacacuccu gauucaccug   1320 cagcacgaag gauacugaag aaugccaacu caacuuuuga agaacuggaa cacguuagga   1380
aguuggucaa aagccugggaa gaaguagggc cccagaucug uacuucuuu gacaacagca   1440 cacagaugaa caugaucaga gauacccugg ggaacccaac aguaaagac uuuuugaaua    1500 ggcagcuugg ugaagaaggu auuacugcug aagccauccu aaacuuccuc uacaagggcc    1560
cucgggaaag ccaggcugac gacauggcca cuucgacug gagagacaua uuuaacauca    1620
cugaucgcac ccucccgccug gucaaucaau accuggagug cuugggcucu gauaaguugg   1680
aaagcuacaa ugaugaaaacu cagcucaccc aacgugccuu cucuauacug gaggaaaaca    1740
uguucugggc cggagugugua uucccuugaca uguacccuug gaccagcucu cuaccaccccc   1800 acgugaaguu uaagauccga auggacauag acguggugga gaaaccaau aagauuaaag    1860
```

-continued

```
acagguauug ggauucuggu cccagagcug aucccgugga agauuccgg uacaucuggg      1920 gcggguuugc cuaucugcag gacaugguug aacaggggau cacaaggagc caggugcagg      1980
cggaggcucc aguuggaauc uaccuccagc agaugcccua ccccugcuuc guggacgauu      2040
cuuucaugau cauccugaac cgcguuucc cuaucuucau ggugcuggca uggaucuacu       2100
cugucuccau gacugugaag agcaucgucu uggagaagga guugcgacug aaggagaccu      2160
ugaaaaauca ggguguuccc aaugcaguga uuuggguuac cugguuccug gacagcuucu     2220 ccaucaugc gaugagcauc uuccuccuga cgauauucau caugcaugga agaauccuac       2280
auuacagcga cccauucauc cucuuccugu ucuuguugga uuucuccacu gccaccauca     2340
ugcugugcuu ucugcucagc accuucuucu ccaaggccag ucuggcagca gccuguagug     2400
gugucaucua uuucaccuc uaccugccac acauccugug cuucgccugg caggaccgca      2460
ugaccgcuga gcugaagaag gcugugagcu uacugucucc gguggcauuu ggauuuggca     2520
cugaguaccu gguucgcuuu gaagagcaag gccggggcu gcaguggagc aacaucggga      2580 acaguccccac ggaaggggac gaauucagcu uccugcuguc caugcagaug augcuccuug   2640
augcugcugu cuauggcuua ucgcuuggu accugauca gguguuccca ggagacuaug       2700
gaaccccacu uccuugguac uuucuucuac aagagucgua uuggcuuggc ggugaagggu     2760
guucaaccag agaagaaaga gcccuggaaa agaccgagcc ccuaacagag gaaacggagg    2820
auccagagca cccagaagga auacacgacu ccuucuuuga acgugagcau ccagggugg      2880 uuccuggggu augcgugaag aaucgguaa agauuuga gcccguggc cggccagcug          2940 uggaccgucu gaacaucacc uucuacgaga accagaucac cgcauuccug ggccacaaug     3000
gagcugggaa aaccaccacc uuguccaucc ugacgggucu guugccacca accucuggga     3060
cugugcucgu uggggaagg gacauugaaa ccagccugga ugcagccggg cagagccuug     3120
gcaugugucc acagcacaac auccuguucc accaccucac gguggcugag cacaugcugu     3180
ucuaugccca gcugaaaagga aagucccagg aggaggccca gcuggagaug gaagccaugu   3240
uggaggacac aggccuccac cacaagcgga augaagaggc ucaggaccua ucagguggca    3300
ugcagagaaa gcugucgguu gccauugccu uguggggaga ugccaaggug gugauucugg     3360
acgaacccac cucgggggug gacccuuacu cgagacgcuc aaucggau cugcuccuga       3420 aguaucgcuc aggcagaacc aucaucaugu ccacucacca cauggacgag gccgaccucc     3480 uugggaccg cauugccauc auugcccagg gaaggcucua cugcucaggc acccacucu      3540 uccugaagaa cugcuuuggc acaggcuugu acuuaaccuu ggucgcaag augaaaaca      3600 uccagagcca aaggaaaggc agugagggga ccugcagcug ucgcucuaag gguuucucca    3660
ccacgugucc agcccacguc gaugaccuaa cuccagaaca aguccuggau ggggauguaa     3720
augagcugau ggauguaguu cuccaccaug uuccagaggc aaaagcugguug gagugcauug    3780 gucaagaacu uaucuuccuu cuuccaaaua gaacuucaa gcacagagca uaugccagcc     3840
uuuucagaga gcuggaggag acgcuggcug accuuggucu cagcaguuuu ggaauuucug     3900 acacucccu ggaagagauu uuucugaagg ucacggagga uucugauuca ggaccucugu      3960 uugcggggg cgcucagcag aaaagagaaa acgucaaccc cgacacccc ugcuuggguc        4020 ccagagagaa ggcuggacag acaccccagg acuccaaugu cugcucccca ggggcgccgg    4080
cugcucaccc agagggccag ccuccccag agccagagug cccaggcccg cagcucaaca      4140
cggggacaca gcugguccuc cagcaugugc aggcgcugcu ggucaagaga uuccaacaca    4200
```

```
ccauccgcag ccacaaggac uuccuggcgc agaucgugcu cccggcuacc uuugugutuu    4260
uggcucugau gcuuucuauu guuaucccuc cuuuuggcga auaccccgcu uugacccuuc    4320
accccuggau auaugggcag caguacaccu ucuucagcau ggaugaacca ggcagugagc    4380
aguucacggu acuugcagac guccuccuga auaagccagg cuuuggcaac cgcugccuga    4440
aggaagggug gcuuccggag uaccccugug gcaaucaac acccuggaag acuccuucug     4500
ugucccaaaa caucacccag cuguuccaga agcagaaaug gacacagguc aacccuucac    4560
cauccugcag gugcagcacc agggagaagc ucaccaugcu gccagagugc cccgagggug    4620 ccggggggccu cccgccccc cagagaacac agcgcagcac ggaaauucua caagaccuga    4680
cggacaggaa caucuccgac uucuugguaa aaacguaucc ugcucuuaua agaagcagcu   4740
uaaagagcaa auucugggug aaugaacaga gguauggagg aauuuccauu ggaggaaagc    4800
ucccagucgu ccccaucacg ggggaagcac uguuggguu uuuaagcgac cuuggccgga    4860
ucaugaaugu gagcggggggc ccuaucacua gagaggccuc uaaagaaaua ccugauuucc    4920
uuuaacaucu agaaacugaa gacaacauua aggugugguu uaauaacaaa ggcuggcaug    4980
cccuggucag cuuucucaau guggcccaca acgccaucuu acgggccagc ugccuaagg     5040 acaggagccc cgaggaguau ggaaucaccg ucauuagcca cccccugaac ugaccaaggg    5100
agcagcucuc agagauuaca gugcugacca cuucagugga ugcuguggu gccaucgcg      5160 ugauuuucuc caugccuuc gucccagcca gcuuugccu uuauuugauc caggagcggg     5220
ugaacaaauc caagcaccuc caguuuauca guggagugag ccccaccacc uacugggugga   5280 ccaacuuccu cugggacauc augaauuauu ccgugagugc ugggcuggug ugggcaucu    5340 ucaucggguu ucagaagaaa gccuacacuu uccagaaaaa ccuuccugcc cuuguggcac    5400
ugcuccugcu guauggaugg gcggucauuc ccaugaugua cccagcaucc uuccuguuu    5460 auguccccag cacagccuau guggcuuuau cuugugcuaa ucuguucauc ggcaucaaca    5520
gcagugcuau uaccuucauc uuggaauuau uugagaauaa ccggacgcug ucagguuca    5580 acgccgugcu gaggaagcug cucauugucu uccccacuu ugccugggc cgggggcuca    5640 uugaccuugc acugaccag gcugugacag augucauagc ccgguuuggu gaggagcacu    5700
cugcaaauuc guuccacugg gaccugauug ggaagaaccu guugccaug guggugaag     5760 gggggugugua cuuccuccug acccugcugg uccagcgcca cuucuuccuc ucccaauggga   5820 uugccgagcc cacuaaggag cccauuguug augaagauga ugauguggcu gaagaaagac    5880
aaagaauuau uacuggugga aauaaaacug acaucuuaag gcuacaugaa cuaaccaaga    5940
uuuauccagg caccuccagc ccagcaguggg acaggcugug ugucggaguu cgcccuggag    6000 agugcuuuugg ccuccuggga gugaauuggu ccggcaaaac aaccacauuc aagaugcuca    6060
cuggggacac cacagugacc ucaggggaug ccaccguagc aggcaagagu auuuuaacca    6120
auauuucuga aguccaucaa aauaugggcu acguccuca guuugaugca auugaugagc    6180
ugcucacagg acgagaacau cuuuaccuuu augcccggcu ucgaggugua ccagcagaag    6240
aaaucgaaaa gguugcaaac uggagauauua agagccuggg ccugacuguc uacgccgacu    6300
gccuggcugg cacguacagu gggggcaaca agcggaaacu cuccacagcc aucgcacuca    6360
uuggcugccc accgcuggug cugcuggaug agcccaccac agggauggac ccccaggcac    6420
gccgcaugcu guggaacguc aucgugagca ucagagaaa agggaggggcu gugucccuca    6480 cauccacag cauggaagaa ugugaggcac ugugguaccg gcuggccauc augguaaagg     6540
gcgccuuucg auguauggggc accauucagc aucucaaguc caaauuugga gauggcuaua    6600
```

-continued

```
ucgucacaau gaagaucaaa uccccgaagg acgaccugcu uccugaccug aacccugugg    6660
agcaguucuu ccaggggaac uucccaggca gugugcagag ggagaggcac ucaacaugc     6720 uccaguucca ggucccucuc uccucccugg cgaggaucuu ccagcuccuc cucucccaca    6780
aggacagccu gcucaucgag gaguacucag ucacacagac cacacuggac cagguguuug    6840
uaaauuuugc uaaacagcag acugaaaguc augaccuccc ucugcacccu cgagcugcug    6900
gagccagucg acaagcccag gacugaucuu ucacaccgcu cguuccugca gccgaaaagg    6960
aacucugggc agcuggaggc gcaggagccu gucccauau ggucauccaa auggacuggc     7020
cagcguaaau gaccccacug cagcagaaaa caaacacacg aggagcaugc agcgaauuca    7080
gaaagagguc uuucagaagg aaaccgaaac ugacuugcuc accuggaaca ccugauggug    7140
aaaccaaaca aauacaaaau ccuucuccag accccagaac uagaaacccc gggccauccc    7200
acuagcagcu uuggccucca uauugcucuc auuucaagca gaucugcuuu ucugcauguu    7260
ugucugugug ucugcguugu gugugauuuu cauggaaaaa uaaaaugcaa augcacucau    7320
cacaaa                                                              7326
```

<210> SEQ ID NO 3
<211> LENGTH: 2273
<212> TYPE: PRT
<213> ORGANISM: Homo sapiens

<400> SEQUENCE: 3

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240
```

```
Glu Asp Thr Leu Tyr Ala Asn Val Asp Phe Phe Lys Leu Phe Arg Val
            245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
            275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
            355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
            405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
            435                 440                 445

Asn Met Ile Arg Asp Thr Leu Gly Asn Pro Thr Val Lys Asp Phe Leu
    450                 455                 460

Asn Arg Gln Leu Gly Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
            485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
            515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
            565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
            595                 600                 605

Ala Tyr Leu Gln Asp Met Val Glu Gln Gly Ile Thr Arg Ser Gln Val
            610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
            645                 650                 655
```

```
Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
            675                 680                 685

Gln Gly Val Ser Asn Ala Val Ile Trp Cys Thr Trp Phe Leu Asp Ser
            690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
            755                 760                 765

Tyr Phe Thr Leu Tyr Leu Pro His Ile Leu Cys Phe Ala Trp Gln Asp
            770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
            805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
            835                 840                 845

Val Tyr Gly Leu Leu Ala Trp Tyr Leu Asp Gln Val Phe Pro Gly Asp
850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
                885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
            915                 920                 925

Val Cys Val Lys Asn Leu Val Lys Ile Phe Glu Pro Cys Gly Arg Pro
930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                1005

Pro Gln His Asn Ile Leu Phe  His His Leu Thr Val  Ala Glu His
    1010                1015                1020

Met Leu Phe Tyr Ala Gln Leu  Lys Gly Lys Ser Gln  Glu Glu Ala
    1025                1030                1035

Gln Leu Glu Met Glu Ala Met  Leu Glu Asp Thr Gly  Leu His His
    1040                1045                1050

Lys Arg Asn Glu Glu Ala Gln  Asp Leu Ser Gly Gly  Met Gln Arg
    1055                1060                1065

Lys Leu Ser Val Ala Ile Ala  Phe Val Gly Asp Ala  Lys Val Val
```

-continued

```
                1070                1075                1080
Ile Leu Asp Glu Pro Thr Ser Gly Val Asp Pro Tyr Ser Arg Arg
                1085                1090                1095
Ser Ile Trp Asp Leu Leu Leu Lys Tyr Arg Ser Gly Arg Thr Ile
                1100                1105                1110
Ile Met Ser Thr His His Met Asp Glu Ala Asp Leu Leu Gly Asp
                1115                1120                1125
Arg Ile Ala Ile Ile Ala Gln Gly Arg Leu Tyr Cys Ser Gly Thr
                1130                1135                1140
Pro Leu Phe Leu Lys Asn Cys Phe Gly Thr Gly Leu Tyr Leu Thr
                1145                1150                1155
Leu Val Arg Lys Met Lys Asn Ile Gln Ser Gln Arg Lys Gly Ser
                1160                1165                1170
Glu Gly Thr Cys Ser Cys Ser Ser Lys Gly Phe Ser Thr Thr Cys
                1175                1180                1185
Pro Ala His Val Asp Asp Leu Thr Pro Glu Gln Val Leu Asp Gly
                1190                1195                1200
Asp Val Asn Glu Leu Met Asp Val Val Leu His His Val Pro Glu
                1205                1210                1215
Ala Lys Leu Val Glu Cys Ile Gly Gln Glu Leu Ile Phe Leu Leu
                1220                1225                1230
Pro Asn Lys Asn Phe Lys His Arg Ala Tyr Ala Ser Leu Phe Arg
                1235                1240                1245
Glu Leu Glu Glu Thr Leu Ala Asp Leu Gly Leu Ser Ser Phe Gly
                1250                1255                1260
Ile Ser Asp Thr Pro Leu Glu Glu Ile Phe Leu Lys Val Thr Glu
                1265                1270                1275
Asp Ser Asp Ser Gly Pro Leu Phe Ala Gly Gly Ala Gln Gln Lys
                1280                1285                1290
Arg Glu Asn Val Asn Pro Arg His Pro Cys Leu Gly Pro Arg Glu
                1295                1300                1305
Lys Ala Gly Gln Thr Pro Gln Asp Ser Asn Val Cys Ser Pro Gly
                1310                1315                1320
Ala Pro Ala Ala His Pro Glu Gly Gln Pro Pro Glu Pro Glu
                1325                1330                1335
Cys Pro Gly Pro Gln Leu Asn Thr Gly Thr Gln Leu Val Leu Gln
                1340                1345                1350
His Val Gln Ala Leu Leu Val Lys Arg Phe Gln His Thr Ile Arg
                1355                1360                1365
Ser His Lys Asp Phe Leu Ala Gln Ile Val Leu Pro Ala Thr Phe
                1370                1375                1380
Val Phe Leu Ala Leu Met Leu Ser Ile Val Ile Pro Pro Phe Gly
                1385                1390                1395
Glu Tyr Pro Ala Leu Thr Leu His Pro Trp Ile Tyr Gly Gln Gln
                1400                1405                1410
Tyr Thr Phe Phe Ser Met Asp Glu Pro Gly Ser Glu Gln Phe Thr
                1415                1420                1425
Val Leu Ala Asp Val Leu Leu Asn Lys Pro Gly Phe Gly Asn Arg
                1430                1435                1440
Cys Leu Lys Glu Gly Trp Leu Pro Glu Tyr Pro Cys Gly Asn Ser
                1445                1450                1455
Thr Pro Trp Lys Thr Pro Ser Val Ser Pro Asn Ile Thr Gln Leu
                1460                1465                1470
```

-continued

```
Phe Gln Lys Gln Lys Trp Thr Gln Val Asn Pro Ser Pro Ser Cys
    1475                1480                1485

Arg Cys Ser Thr Arg Glu Lys Leu Thr Met Leu Pro Glu Cys Pro
    1490                1495                1500

Glu Gly Ala Gly Gly Leu Pro Pro Pro Gln Arg Thr Gln Arg Ser
    1505                1510                1515

Thr Glu Ile Leu Gln Asp Leu Thr Asp Arg Asn Ile Ser Asp Phe
    1520                1525                1530

Leu Val Lys Thr Tyr Pro Ala Leu Ile Arg Ser Ser Leu Lys Ser
    1535                1540                1545

Lys Phe Trp Val Asn Glu Gln Arg Tyr Gly Gly Ile Ser Ile Gly
    1550                1555                1560

Gly Lys Leu Pro Val Val Pro Ile Thr Gly Glu Ala Leu Val Gly
    1565                1570                1575

Phe Leu Ser Asp Leu Gly Arg Ile Met Asn Val Ser Gly Gly Pro
    1580                1585                1590

Ile Thr Arg Glu Ala Ser Lys Glu Ile Pro Asp Phe Leu Lys His
    1595                1600                1605

Leu Glu Thr Glu Asp Asn Ile Lys Val Trp Phe Asn Asn Lys Gly
    1610                1615                1620

Trp His Ala Leu Val Ser Phe Leu Asn Val Ala His Asn Ala Ile
    1625                1630                1635

Leu Arg Ala Ser Leu Pro Lys Asp Arg Ser Pro Glu Glu Tyr Gly
    1640                1645                1650

Ile Thr Val Ile Ser Gln Pro Leu Asn Leu Thr Lys Glu Gln Leu
    1655                1660                1665

Ser Glu Ile Thr Val Leu Thr Thr Ser Val Asp Ala Val Val Ala
    1670                1675                1680

Ile Cys Val Ile Phe Ser Met Ser Phe Val Pro Ala Ser Phe Val
    1685                1690                1695

Leu Tyr Leu Ile Gln Glu Arg Val Asn Lys Ser Lys His Leu Gln
    1700                1705                1710

Phe Ile Ser Gly Val Ser Pro Thr Thr Tyr Trp Val Thr Asn Phe
    1715                1720                1725

Leu Trp Asp Ile Met Asn Tyr Ser Val Ser Ala Gly Leu Val Val
    1730                1735                1740

Gly Ile Phe Ile Gly Phe Gln Lys Lys Ala Tyr Thr Ser Pro Glu
    1745                1750                1755

Asn Leu Pro Ala Leu Val Ala Leu Leu Leu Leu Tyr Gly Trp Ala
    1760                1765                1770

Val Ile Pro Met Met Tyr Pro Ala Ser Phe Leu Phe Asp Val Pro
    1775                1780                1785

Ser Thr Ala Tyr Val Ala Leu Ser Cys Ala Asn Leu Phe Ile Gly
    1790                1795                1800

Ile Asn Ser Ser Ala Ile Thr Phe Ile Leu Glu Leu Phe Glu Asn
    1805                1810                1815

Asn Arg Thr Leu Leu Arg Phe Asn Ala Val Leu Arg Lys Leu Leu
    1820                1825                1830

Ile Val Phe Pro His Phe Cys Leu Gly Arg Gly Leu Ile Asp Leu
    1835                1840                1845

Ala Leu Ser Gln Ala Val Thr Asp Val Tyr Ala Arg Phe Gly Glu
    1850                1855                1860
```

Glu His Ser Ala Asn Pro Phe His Trp Asp Leu Ile Gly Lys Asn
1865                1870                1875

Leu Phe Ala Met Val Val Glu Gly Val Val Tyr Phe Leu Leu Thr
1880                1885                1890

Leu Leu Val Gln Arg His Phe Phe Leu Ser Gln Trp Ile Ala Glu
1895                1900                1905

Pro Thr Lys Glu Pro Ile Val Asp Glu Asp Asp Val Ala Glu
1910                1915                1920

Glu Arg Gln Arg Ile Ile Thr Gly Gly Asn Lys Thr Asp Ile Leu
1925                1930                1935

Arg Leu His Glu Leu Thr Lys Ile Tyr Pro Gly Thr Ser Ser Pro
1940                1945                1950

Ala Val Asp Arg Leu Cys Val Gly Val Arg Pro Gly Glu Cys Phe
1955                1960                1965

Gly Leu Leu Gly Val Asn Gly Ala Gly Lys Thr Thr Thr Phe Lys
1970                1975                1980

Met Leu Thr Gly Asp Thr Thr Val Thr Ser Gly Asp Ala Thr Val
1985                1990                1995

Ala Gly Lys Ser Ile Leu Thr Asn Ile Ser Glu Val His Gln Asn
2000                2005                2010

Met Gly Tyr Cys Pro Gln Phe Asp Ala Ile Asp Glu Leu Leu Thr
2015                2020                2025

Gly Arg Glu His Leu Tyr Leu Tyr Ala Arg Leu Arg Gly Val Pro
2030                2035                2040

Ala Glu Glu Ile Glu Lys Val Ala Asn Trp Ser Ile Lys Ser Leu
2045                2050                2055

Gly Leu Thr Val Tyr Ala Asp Cys Leu Ala Gly Thr Tyr Ser Gly
2060                2065                2070

Gly Asn Lys Arg Lys Leu Ser Thr Ala Ile Ala Leu Ile Gly Cys
2075                2080                2085

Pro Pro Leu Val Leu Leu Asp Glu Pro Thr Thr Gly Met Asp Pro
2090                2095                2100

Gln Ala Arg Arg Met Leu Trp Asn Val Ile Val Ser Ile Ile Arg
2105                2110                2115

Glu Gly Arg Ala Val Val Leu Thr Ser His Ser Met Glu Glu Cys
2120                2125                2130

Glu Ala Leu Cys Thr Arg Leu Ala Ile Met Val Lys Gly Ala Phe
2135                2140                2145

Arg Cys Met Gly Thr Ile Gln His Leu Lys Ser Lys Phe Gly Asp
2150                2155                2160

Gly Tyr Ile Val Thr Met Lys Ile Lys Ser Pro Lys Asp Asp Leu
2165                2170                2175

Leu Pro Asp Leu Asn Pro Val Glu Gln Phe Phe Gln Gly Asn Phe
2180                2185                2190

Pro Gly Ser Val Gln Arg Glu Arg His Tyr Asn Met Leu Gln Phe
2195                2200                2205

Gln Val Ser Ser Ser Leu Ala Arg Ile Phe Gln Leu Leu Leu
2210                2215                2220

Ser His Lys Asp Ser Leu Leu Ile Glu Glu Tyr Ser Val Thr Gln
2225                2230                2235

Thr Thr Leu Asp Gln Val Phe Val Asn Phe Ala Lys Gln Gln Thr
2240                2245                2250

Glu Ser His Asp Leu Pro Leu His Pro Arg Ala Ala Gly Ala Ser

Arg Gln Ala Gln Asp
     2270

<210> SEQ ID NO 4
<211> LENGTH: 1816
<212> TYPE: RNA
<213> ORGANISM: Homo sapiens

<400> SEQUENCE: 4

| ugaagaggaa | aaucaaugcu | guaagggaaa | aaaaaaaugg | cauuagagau | ccagaccuua | 60 |
| uaggcauuuu | ccaaauuauu | aauucaaucu | cucaaaacag | guggcgcuca | gcagaaaaga | 120 |
| gaaaacguca | accccgaca | ccccugcuug | ggucccagag | agaaggcugg | acagacaccc | 180 |
| caggacucca | augucugcuc | ccaggggcg | ccggcugcuc | acccagaggg | ccagccuccc | 240 |
| ccagagccag | agugcccagg | cccgcagcuc | aacacgggga | cacagcuggu | ccuccagcau | 300 |
| gugcaggcgc | ugcuggucaa | gagauuccaa | cacaccaucc | gcagccacaa | ggacuuccug | 360 |
| gcgcagguac | uauugucggu | cggguguuag | cugagcucag | uggcuccucu | cccagccuuc | 420 |
| cccuccucuc | cugaguguuc | cuucaggcau | ggguuauaac | ucagcaagga | gcacccucuu | 480 |
| uagauucugc | ugguuuuguu | uccugcuuuc | caaacccuua | ucuugauucu | ugguaacaug | 540 |
| aaucuucuuu | guaaguugga | ccuccccuag | caaagaaaau | agaauaauag | ugaaaauguu | 600 |
| aauauuguuu | uuauuuuuac | agugagggau | aaagucaugu | uucauucau | uuuugcagug | 660 |
| acccuacaua | ucaaaaucau | ugcccucuuu | uuucuuuuaa | uguuguuuaa | uuuagaaaaa | 720 |
| gaagcucugg | uuuaaagaac | agugagucac | ugacuugcu | cuuugaaaug | cccuuugaag | 780 |
| ucuggcugaa | cacugggcug | cauucagauu | cuucagguggc | caccagaaca | uucuguuuuc | 840 |
| uucugcacau | cuuaccuuug | cacacccugc | uuauuauguu | ccccccagaag | cccaacccuc | 900 |
| uccaccaggg | gcugauuagg | aggcugcagg | auaaauguuu | aaaagaauga | agaugugugu | 960 |
| gcacgcgcac | gugugacauc | uccaugccac | agucauguuu | auuccacguc | uauucuccca | 1020 |
| cagaucgugc | ucccggcuac | cuuuguguuu | uuggcucuga | ugcuuucuau | uguuauucccu | 1080 |
| ccuuuuggcg | aauaccccgc | uuugacccuu | caccccugga | uauaugggca | gcaguacacc | 1140 |
| uucuucaggu | gcgcgacuc | ggggucacca | uucccucug | uggguuuggg | gcaccgggu | 1200 |
| cacaugcugc | uuagaagggc | ccugaccuuc | ccacuucacu | gggaccuuca | ccaaugagag | 1260 |
| aggggagggg | ucuuugggcu | gccugcagaa | aggaacuuaa | uguaucugcc | acugcuugga | 1320 |
| aaggcgaucc | uaguggacag | gcaggacugc | ugggaaggc | cgaaugggga | aaggaaugca | 1380 |
| aagcuuaggu | gaauggguug | aagcgccauc | uuuugaggc | auaggugaca | ugccaucaga | 1440 |
| ccacugcgag | uguucaggca | gccuaccgca | cucccaggag | agcuagcgcc | auccccaaggc | 1500 |
| agcauucggu | gccuccaaua | cauaccuggc | acacagcagc | uaccaguaa | aggcucugag | 1560 |
| uugcaugaug | uuggcacgcg | ccugcucugu | cccagucaca | ugucacucu | ugucuagcau | 1620 |
| ggaugaaacca | ggcagugagc | aguucacggu | acuugcagac | guccuccuga | auaagccagg | 1680 |
| cuuuggcaac | cgcugccuga | aggaagggug | gcuuccguaa | gugccuacgc | gccccugucc | 1740 |
| uaagaagacu | agcuccccug | ggaggaccca | acggugggu | caagauggca | ggcguugggg | 1800 |
| aggccccacu | caauucc | | | | | 1816 |

<210> SEQ ID NO 5
<211> LENGTH: 275
<212> TYPE: RNA

<213> ORGANISM: Homo sapiens

<400> SEQUENCE: 5

| gaagaugugu gugcacgcgc acgugugaca ucuccaugcc acagucaugu uuauuccacg | 60 |
| ucuauucucc cacagaucgu gcucccggcu accuuugugu uuuggcucu gaugcuuucu | 120 |
| auuguuaucc cuccuuuugg cgaauacccc gcuugacccc uucaccccug gauauauggg | 180 |
| cagcaguaca ccuucuucag gugcgcggac ucgggucac cauuccccuc uguggguuug | 240 |
| gggcaccugg gucacaugcu gcuuagaagg gcccu | 275 |

<210> SEQ ID NO 6
<211> LENGTH: 65
<212> TYPE: RNA
<213> ORGANISM: Homo sapiens

<400> SEQUENCE: 6

| ucggggucac cauuccccuc uguggguuug gggcaccugg gucacaugcu gcuuagaagg | 60 |
| gcccu | 65 |

<210> SEQ ID NO 7
<211> LENGTH: 41
<212> TYPE: RNA
<213> ORGANISM: Homo sapiens

<400> SEQUENCE: 7

| uucccucug uggguuuggg gcaccugggu cacaugcugc u | 41 |

<210> SEQ ID NO 8
<211> LENGTH: 31
<212> TYPE: RNA
<213> ORGANISM: Homo sapiens

<400> SEQUENCE: 8

| cucugugggu uugggcacc uggucacau g | 31 |

<210> SEQ ID NO 9
<211> LENGTH: 41
<212> TYPE: RNA
<213> ORGANISM: Homo sapiens

<400> SEQUENCE: 9

| cuguggguuu gggggcaccug ggucacaugc ugcuuagaag g | 41 |

<210> SEQ ID NO 10
<211> LENGTH: 31
<212> TYPE: RNA
<213> ORGANISM: Homo sapiens

<400> SEQUENCE: 10

| gguuugggc accugggguca caugcugcuu a | 31 |

<210> SEQ ID NO 11
<211> LENGTH: 40
<212> TYPE: RNA
<213> ORGANISM: Homo sapiens

<400> SEQUENCE: 11

| uggguuuggg gcaccugggu cacaugcugc uuagaagggc | 40 |

<210> SEQ ID NO 12
<211> LENGTH: 30

```
<212> TYPE: RNA
<213> ORGANISM: Homo sapiens

<400> SEQUENCE: 12
uuggggcacc ugggucacau gcugcuuaga                                          30

<210> SEQ ID NO 13
<211> LENGTH: 41
<212> TYPE: RNA
<213> ORGANISM: Homo sapiens

<400> SEQUENCE: 13
ggggcaccug ggucacaugc ugcuuagaag ggcccugacc u                             41

<210> SEQ ID NO 14
<211> LENGTH: 31
<212> TYPE: RNA
<213> ORGANISM: Homo sapiens

<400> SEQUENCE: 14
accuggguca caugcugcuu agaagggccc u                                        31

<210> SEQ ID NO 15
<211> LENGTH: 40
<212> TYPE: RNA
<213> ORGANISM: Homo sapiens

<400> SEQUENCE: 15
gugcgcggac ucggggucac cauucuccuc uguggguuug                               40

<210> SEQ ID NO 16
<211> LENGTH: 30
<212> TYPE: RNA
<213> ORGANISM: Homo sapiens

<400> SEQUENCE: 16
cggacucggg gucaccauuc uccucugugg                                          30

<210> SEQ ID NO 17
<211> LENGTH: 21
<212> TYPE: RNA
<213> ORGANISM: Artificial Sequence
<220> FEATURE:
<223> OTHER INFORMATION: AON1

<400> SEQUENCE: 17
gacccaggug ucccaaaccc a                                                   21

<210> SEQ ID NO 18
<211> LENGTH: 21
<212> TYPE: RNA
<213> ORGANISM: Artificial Sequence
<220> FEATURE:
<223> OTHER INFORMATION: AON2

<400> SEQUENCE: 18
agcaugugac ccaggugucc c                                                   21

<210> SEQ ID NO 19
<211> LENGTH: 20
<212> TYPE: RNA
<213> ORGANISM: Artificial Sequence
<220> FEATURE:
<223> OTHER INFORMATION: AON 3
```

```
<400> SEQUENCE: 19
gcagcaugug acccaggugu                                                    20

<210> SEQ ID NO 20
<211> LENGTH: 21
<212> TYPE: RNA
<213> ORGANISM: Artificial Sequence
<220> FEATURE:
<223> OTHER INFORMATION: AON4

<400> SEQUENCE: 20
ccuucuaagc agcaugugac c                                                  21

<210> SEQ ID NO 21
<211> LENGTH: 20
<212> TYPE: RNA
<213> ORGANISM: Artificial Sequence
<220> FEATURE:
<223> OTHER INFORMATION: AON5

<400> SEQUENCE: 21
gaggagaaug gugaccccga                                                    20

<210> SEQ ID NO 22
<211> LENGTH: 13362
<212> TYPE: DNA
<213> ORGANISM: Artificial Sequence
<220> FEATURE:
<223> OTHER INFORMATION: pCI-Neo-Rho-ABCA4-26-29 wild-type

<400> SEQUENCE: 22
ttgtacaaag tggtgatctt gtacaaagtg gtgatgagag gtacctccga ggggtaaaca        60
gttgggtaaa cagtctctga agtcagctct gccatttct agctgtatgg ccctgggcaa       120
gtcaatttcc ttctctgtgc tttggtttcc tcatccatag aaaggtagaa agggcaaaac       180
accaaactct tggattacaa gagataattt acagaacacc cttggcacac agagggcacc       240
atgaaatgtc acgggtgaca cagccccctt gtgctcagtc cctggcatct ctaggggtga       300
ggagcgtctg cctagcaggt tcccaccagg aagctggatt tgagtggatg gggcgctgga       360
atcgtgaggg gcagaagcag gcaaagggtc ggggcgaacc tcactaacgt gccagttcca       420
agcacactgt gggcagccct ggccctgact caagcctctt gccttccagt tccggaactg       480
catgctcacc accatctgct gcggcaagaa cccactgggt gacgatgagg cctctgctac       540
cgtgtccaag acgagacga gccaggtggc cccggcctaa gacctgccta ggactctgtg       600
gccgactata ggcgtctccc atcccctaca cctgtcgacc cgggcggccg cttccctta       660 gtgagggtta atgcttcgag cagacatgat aagatacatt gatgagtttg gacaaaccac       720
aactagaatg cagtgaaaaa aatgctttat ttgtgaaatt tgtgatgcta ttgctttatt       780
tgtaaccatt ataagctgca ataaacaagt taacaacaac aattgcattc attttatgtt       840
tcaggttcag ggggagatgt gggaggtttt ttaaagcaag taaaacctct acaaatgtgg       900
taaaatccga taaggatcga tccgggctgg cgtaatagcg aagaggcccg caccgatcgc       960
ccttcccaac agttgcgcag cctgaatggc gaatggacgc gccctgtagc ggcgcattaa      1020
gcgcggcggg tgtggtggtt acgcgcagcg tgaccgctac acttgccagc gccctagcgc      1080
ccgctccttt cgctttcttc ccttcctttc tcgccacgtt cgccggcttt ccccgtcaag      1140
ctctaaatcg ggggctccct ttagggttcc gatttagtgc tttacggcac ctcgacccca      1200
aaaaacttga ttagggtgat ggttcacgta gtgggccatc gccctgatag acggtttttc      1260
```

-continued

```
gcccttttgac gttggagtcc acgttcttta atagtggact cttgttccaa actggaacaa   1320
cactcaaccc tatctcggtc tattcttttg atttataagg gattttgccg atttcggcct    1380
attggttaaa aaatgagctg atttaacaaa aatttaacgc gaattttaac aaaatattaa    1440
cgcttacaat ttcctgatgc ggtatttct ccttacgcat ctgtgcgta tttcacaccg      1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc gcccctaac tccgcccagt    1800
tccgcccatt ctccgcccca tggctgacta attttttta tttatgcaga ggccgaggcc    1860
gcctcggcct ctgagctatt ccagaagtag tgaggaggct ttttggagg cctaggcttt    1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcagggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct ttttgcggc attttgcctt cctgttttg    3360
ctcacccaga aacgctggtg aaagtaaaag atgctgaaga tcagttgggt gcacgagtgg   3420
gttacatcga actggatctc aacagcggta agatccttga gttttcgc cccgaagaac     3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
```

```
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatccttt tgataatctc atgaccaaaa   4260
tcccttaacg tgagttttcg ttccactgag cgtcagaccc cgtagaaaag atcaaaggat   4320
cttcttgaga tcctttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc cttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacgggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
```

```
ctccacaggt gtccactccc agttcaatta cagctcttaa ggctagagta cttaatacga    6060
ctcactatag gctagcctcg agaattccgg aggtcaacaa cgagtcttt gtcatctaca     6120
tgttcgtggt ccacttcacc atccccatga ttatcatctt tttctgctat gggcagctcg    6180
tcttcaccgt caaggaggta cgggccgggg ggtgggcggc ctcacggctc tgagggtcca    6240
gcccccagca tgcatctgcg gctcctgctc cctggaggag ccatatcaca agtttgtaca    6300
aaaaagcagg cttccaccca agcatagcaa ctatctttat ttttggcata gttccccat     6360
ctctgcatgc atacaaattt tatgtacttg tggttactgt gtgcttacgt ttttgtattt    6420
atagaagatg atgttctcag atagagtcgt aatggatttt cttcccatta tgaagcaata    6480
cccaacaaaa cagagcttgg gttagatttt tctgagaata agaatgacta aacaaaattc    6540
tctctttttt tcttcttgac agatttttct gaaggtcacg gaggattctg attcaggacc    6600
tctgtttgcg ggtatggtgc tggagccagt ggcttgttcc cttccttgcc tccctcccaa    6660
gttccatctc gaaagtctaa ggggctgggc acagtggctc atgcctgtaa tcccagcaat    6720
ttgggaggcc aaggcagatg gaccacctga gttcgagacc agcctggcca catggtgaa     6780
accccatctg tactaaaaat acaaaaatta gctaggtgtg gtggcgcgca cctgtaattc    6840
cagctactcg ggaggctgag gcaggagaat cacttgaacc tgggaggcag aggttgcagt    6900
gagcagagat tgtgccactg cactgcagcc tgagcgacaa gagcaaaatc catctcaaaa    6960
aaaaaaaaaa gtctaaggaa aaagtcatga aacaacaaag caggcaaata ctcctccata    7020
gtatctgact ccccagtagt aggcattttg catcctagat ggctttgagt gacaaaggaa    7080
taacagactg agttaggtct agatggggac actttggatg aatgaggatt cttacggagg    7140
tcaggttggt agcttcatcc ctcagctcct catgctgtat ccccagtctc tcggcctgcc    7200
atgtcatcat cctcatctcc tcctgtcatc tccaccaggc ctctgatcca tctctgtctg    7260
catgagtgac agctggcaga gtccttaatg tttatcaaat acaactcaga cgtcagtctc    7320
ctggcccctt tgagatcaac ataaaatcat tttgaaccct tatttagtgg tctatgggct    7380
ttgaaaacat ggggaccaaa attcctgtgg attctagaag tctctcttct acatgtgtca    7440
gcctgggcac caactagctc cttccatgaa cttttatcaa acccacagcc acacaaagca    7500
tgtgtgagtg tagcagagtt tacagcagag ggtggagggt ggggagatag atgtgtggaa    7560
gggttacctg ccacacaaac agaaaccact tctgatagaa cacgaggtgt ccacccacac    7620
tgtaaaatcc tctcctggta caggcaaagc tttgcagcga ttctcctttg ctgcccctgg    7680
gctcctaaca cctcctaaac caccagttac ctccttcttt ccagtgtggc atatttcagt    7740
gttttcctgt tggagtgttt cctttctatg tggattctgg aatcagctct taagataact    7800
tggttttcat ctttcttcat aatgatccca aacatctatc tactatgcct agaactacca    7860
atggacacat ataccagccc agatatgctt cagcccatcc cagtacatcg catggtgacc    7920
aaaagatgta gtcgtcctgg cacagtgggt gtggggcagg aagcagtcct ctccagggga    7980
cagcagcaat tcaccacaga acccaagttt ctttcaagct ctgctgacac agaaattgaa    8040
taatctcagc tcacccaatg tcaaagactc atattaacca agaccagaat gaaaatatgc    8100
taatttatat cagaagcttt gctggattca agagttaggg cctttacct gtgcagaata    8160
ttccttcttg ataaataggc cctctcagga gaataaatta cacatcagag gactgtttag    8220
tcagcatagg catagaacag gatgttccaa agatacagtc aagggagtg ggtaagagtg     8280
tagcctctgg agtgaggccg accaaatatc aaacctgagc ttcataattt gcaaactaac    8340
```

```
tggctttggg taagtacata gcctctttgt acctgtttcc ccatctgcaa aatggagata   8400
ataatagcat ctacctgtag cattgttgag agaattaagt gagttaatgc ttgccgactt   8460
ataacacagt atacgatcac tgattaagac ttagcaactc taaactaaat gtttacaaac   8520
catctcttac ctcaaagcac ttaacatcca ttgtcttatt tgattatcac tgtaatctta   8580
tgaagcaggc agggcagggg tctgccccat ctgggggaa ctgagctcac agaggttgga   8640
gggtttgcct aaagtcaccc aggccactgg gtctcactct ctggtcttag ctctgtaatc   8700
taggatgctc aatgccacac tctcagccac ttttcagatg gctaagtaca tttgttttga   8760
gttagctcag tctcagagga tgacattttc tgatcttgtc tccagtgttt aaatgaacct   8820
gtagctgtgc attggggtca cacaatgcgt ggcatggaga gggtctgtgg ctgactgcca   8880
cggttactac gtgaaaccat cattacagca gttactactg ttactgcctg agaacatcat   8940
tacaagactg aacgaaggga tcaacatgga aatgataaca aaaaaaccaa agtaactgtt   9000
ttaaggaaag gctagcatcg ggaagaagaa gagagaagaa gagaagaaga aaagggctcc   9060
ctgcttctaa tgagtaaagg cagctcccta agcttctgca gcccttcatt atttattggg   9120
taacaggagg aaggagcagg aggtaatgat tgggtcagct gcttaaatga tcacgggttc   9180
atgttgttac tgacagattt caattatgcc taatcataag aaacatttgt gcagcctcca   9240
acaagggtca atgccacttc tgaaggggtg actcatagtc agtaactaga aagcagcaga   9300
tagctaggga caaactggcg attctgaata ggcctggaac ccttagctct ggccaggtca   9360
gtgggctcca gtcaggatgg agccttcagg gagagatcaa agctcagagg tttgagatga   9420
tatcagccag caaagaggag gggcagtagg gatcctccca gagggagggc cagccataga   9480
agacatcaaa tctgagcccg gatcaggaga aggagcctgc agaactgggg ctctggcacc   9540
gagaacctgc agaacttcgc ccctctgagt gcaggtgcca gggctgggc tgccacccag   9600
ccttcgcatc ccaggcctgg cacgtcatag gtaaatgtag ttgaaaggat gactgagctg   9660
atccaattcc ctttacaact gtccttgtcc tgggggactt gaggagggtt aagaaagcag   9720
ctggggacca accaacagtc ctctaggctc tccatgtcca gcaatagttg ttcagcaaat   9780
gagcattaat cagtgactat aaactgtagc ttcaacataa ccgacaactt gcaatggttt   9840
ctagagcatg ctcccatgtg ttatctcatt taaatttcca aaccaatcct gtgaaatgtt   9900
ctttttttt ttcttttttt ttttttgag atagagtttt gctctgtcac ccaggctgga   9960
atacagcggc tcgatcatag ctcactgcag ccttgacctc ctgggcccaa ggggtcctcc  10020
cacctcagcc tcccaagtag ctgggactac aggcacacgc caccgtgcct ggctaatttc  10080
ttttctagtt gtttgtagag acagggtctc cctatgttgt acaggctgat ctgaaactcc  10140
tggggtcaat caatcctcct ggcttggcct cccaaagtgc tgggattaca ggcatgagcc  10200
accatgcctt cattttacag ataagaagtc tgagaaaact cagatttagg cagattgagt  10260
cacttcccca aatttatgta tcttgtaaga atccatattc aaacctcagt cccctaactc  10320
ttagttcatt acttttcta ccacttctca gtatcctcta agaattcaga aagaaccaca  10380
tcgactctga tttttcattt gtttaagtac acaggtaata ggtgaatgta ttttgttgtt  10440
taaaaattca tataatacac aaaaggctaa agtctcgctt cccacttcct ctcccctttc  10500
tacccaactc tgcctcccca gggagagctt ctgctgacag tcggtggaca ttctttcaga  10560
gttttacaat tatgtgtgtg tgtgtacata agatgtcagt ttttctttgt gtaggataca  10620
tgaacatgaa ttttaaacat aaatgtgagt gtattcaca tattgaccag caccttagtt  10680
ttttgttttg tttgtttggt tttctttgtg ctgtttgaga aggagtcttg ctctgtcacc  10740
```

```
caggctggag tgcagtcttg caatctcggc ttacgcaacc tccacctcct gggttcaagt   10800
gattctcctg cctcagcctc ccgagtagtt gggattacag gtgcctgcca ccatgcctgg   10860 ctaattttg tattttgta gagagggggt ttcactatgt aggtcaagct ggtctcaaac     10920
tgctgacctc aaatgatcca tccacctcag cctcccaaag tgctgagatg acaggcgtga   10980
gcctccgtgc ccagccagtt ttgtttttt attaaccaag ttacgtattt taaacttctc   11040
catgtcaatg cttttagagc tattttgttc tctttaatgt taatagagaa ttttaaggca   11100
atttcaggtg aatctataca atttctctgt ataagtaatt tacactagaa atagattttt   11160
ataaagatga ttaagctacc agcctggtat ttcattgctg acttaaatga agaggaaaat   11220
caatgctgta agggaaaaaa aaaatggcat tagagatcca gaccttatag gcattttcca   11280
aattattaat tcaatctctc aaaacaggtg gcgctcagca gaaagagaaa acgtcaacc    11340 cccgacaccc ctgcttgggt cccagagaga aggctggaca gacacccag gactccaatg    11400 tctgctcccc aggggcgccg gctgctcacc cagagggcca gcctccccca gagccagagt   11460
gcccaggccc gcagctcaac acggggacac agctggtcct ccagcatgtg caggcgctgc   11520
tggtcaagag attccaacac accatccgca gccacaagga cttcctggcg caggtactat   11580
tgtcggtcgg tgtttagctg agctcagtgg ctcctctccc agccttcccc tcctctcctg   11640
agtgttcctt caggcatggg ttataactca gcaaggagca ccctctttag attctgctgg   11700
ttttgtttcc tgctttccaa acccttatct tgattcttgg taacatgaat cttctttgta   11760
agttggacct cccctagcaa agaaaataga ataatagtga aaatgttaat attgttttta   11820 ttttacagt gagggataaa gtcatgtttt cattcatttt tgcagtgacc ctacatatca    11880
aaatcattgc cctctttttt cttttaatgt tgtttaattt agaaaaagaa gctctggttt   11940
aaagaacagt gagtcacgtg acttgctctt tgaaatgccc tttgaagtct ggctgaacac   12000
tgggctgcat tcagattctt cagtggccac cagaacattc tgttttcttc tgcacatctt   12060
acctttgcac accctgctta ttatgttccc ccagaagccc aaccctctcc accagggct    12120 gattaggagg ctgcaggata aatgtttaaa agaatgaaga tgtgtgtgca cgcgcacgtg   12180
tgacatctcc atgccacagt catgtttatt ccacgtctat tctcccacag atcgtgctcc   12240
cggctacctt tgtgtttttg gctctgatgc tttctattgt tatccctcct tttggcgaat   12300
accccgcttt gacccttcac ccctggatat atgggcagca gtacaccttc ttcaggtgcg   12360
cggactcggg gtcaccattc tcctctgtgg gtttggggca cctgggtcac atgctgctta   12420 gaagggcct gaccttccca cttcactggg accttcacca atgagagagg ggaggggtct    12480
ttgggctgcc tgcagaaagg aacttaatgt atctgccact gcttggaaag gcgatcctag   12540
tggacaggca ggactgcttg ggaaggccga atggggaaag gaatgcaaag cttaggtgaa   12600
tgggttgaag cgccatcttt ttgaggcata ggtgacatgc catcagacca ctgcgagtgt   12660
tcaggcagcc taccgcactc ccaggagagc tagcgccatc ccaaggcagc attcggtgcc   12720
tccaatacat acctggcaca cagcagctat ccagtaaagg ctctgagttg catgatgttg   12780
gcacgcgcct gctctgtccc agtcacatgt ctcactctgt ctagcatgga tgaaccaggc   12840
agtgagcagt tcacggtact tgcagacgtc ctcctgaata agccaggctt tggcaaccgc   12900
tgcctgaagg aagggtggct tccgtaagtg cctacgcgcc cctgtcctaa gaagactagc   12960 tccctggga ggacccaacg gtgggttcaa gatggcaggc gttggggagg ccccactcaa    13020
tcctgctctg ctggtcactt ccatgtctct gaccagcact cccccaacct ctccttccac   13080
```

| | | | | |
|---|---|---|---|---|
| acttgtgtgc | agggacattc | actacctcct | aggaagcccc | cacaccactg gacagctcta 13140 |
| tatttctcag | catagaagtt | ctatgttgag | ttgacagatg | attccccata acttatttga 13200 |
| aaggcctctg | agcagggagg | gagggaaata | gggttatgct | attgtgtgat tgggccttga 13260 |
| atggcgtgag | tgacacagtg | gccagtactt | tgtgatagtt | gtgagtctgg agaagggagt 13320 |
| tagcgaaggc | cattgacatc | caccaggaat | cacccagctt | tc 13362 |

<210> SEQ ID NO 23
<211> LENGTH: 13362
<212> TYPE: DNA
<213> ORGANISM: Artificial Sequence
<220> FEATURE:
<223> OTHER INFORMATION: pCI-Neo-Rho-ABCA4-26-29 c.4243+43G>A

<400> SEQUENCE: 23

| | | | | |
|---|---|---|---|---|
| ttgtacaaag | tggtgatctt | gtacaaagtg | gtgatgagag | gtacctccga ggggtaaaca 60 |
| gttgggtaaa | cagtctctga | agtcagctct | gccattttct | agctgtatgg ccctgggcaa 120 |
| gtcaatttcc | ttctctgtgc | tttggtttcc | tcatccatag | aaaggtagaa agggcaaaac 180 |
| accaaactct | tggattacaa | gagataattt | acagaacacc | cttggcacac agagggcacc 240 |
| atgaaatgtc | acgggtgaca | cagcccccct | tgtgctcagtc | cctggcatct ctaggggtga 300 |
| ggagcgtctg | cctagcaggt | tcccaccagg | aagctggatt | tgagtggatg gggcgctgga 360 |
| atcgtgaggg | gcagaagcag | gcaaagggtc | ggggcgaacc | tcactaacgt gccagttcca 420 |
| agcacactgt | gggcagccct | ggccctgact | caagcctctt | gccttccagt tccggaactg 480 |
| catgctcacc | accatctgct | gcggcaagaa | cccactgggt | gacgatgagg cctctgctac 540 |
| cgtgtccaag | acggagacga | gccaggtggc | cccggcctaa | gacctgccta ggactctgtg 600 |
| gccgactata | ggcgtctccc | atcccctaca | cctgtcgacc | cgggcggccg cttccctta 660 |
| gtgagggtta | atgcttcgag | cagacatgat | aagatacatt | gatgagtttg acaaaccac 720 |
| aactagaatg | cagtgaaaaa | aatgctttat | ttgtgaaatt | tgtgatgcta ttgctttatt 780 |
| tgtaaccatt | ataagctgca | ataaacaagt | taacaacaac | aattgcattc attttatgtt 840 |
| tcaggttcag | ggggagatgt | gggaggtttt | ttaaagcaag | taaaacctct acaaatgtgg 900 |
| taaaatccga | taaggatcga | tccgggctgg | cgtaatagcg | aagaggcccg caccgatcgc 960 |
| ccttcccaac | agttgcgcag | cctgaatggc | gaatggacgc | gccctgtagc ggcgcattaa 1020 |
| gcgcggcggg | tgtggtggtt | acgcgcagcg | tgaccgctac | acttgccagc gccctagcgc 1080 |
| ccgctccttt | cgctttcttc | ccttcctttc | tcgccacgtt | cgccggcttt ccccgtcaag 1140 |
| ctctaaatcg | ggggctccct | ttagggttcc | gatttagtgc | tttacggcac ctcgacccca 1200 |
| aaaaacttga | ttagggtgat | ggttcacgta | gtgggccatc | gccctgatag acggtttttc 1260 |
| gccctttgac | gttggagtcc | acgttcttta | atagtggact | cttgttccaa actggaacaa 1320 |
| cactcaaccc | tatctcggtc | tattcttttg | atttataagg | gattttgccg atttcggcct 1380 |
| attggttaaa | aaatgagctg | atttaacaaa | aatttaacgc | gaattttaac aaaatattaa 1440 |
| cgcttacaat | ttcctgatgc | ggtattttct | ccttacgcat | ctgtgcggta tttcacaccg 1500 |
| catacgcgga | tctgcgcagc | accatggcct | gaaataacct | ctgaaagagg aacttggtta 1560 |
| ggtaccttct | gaggcggaaa | gaaccagctg | tggaatgtgt | gtcagttagg gtgtggaaag 1620 |
| tccccaggct | ccccagcagg | cagaagtatg | caaagcatgc | atctcaatta gtcagcaacc 1680 |
| aggtgtggaa | agtccccagg | ctccccagca | ggcagaagta | tgcaaagcat gcatctcaat 1740 |
| tagtcagcaa | ccatagtccc | gcccctaact | ccgcccatcc | cgcccctaac tccgcccagt 1800 |

```
tccgcccatt ctccgcccca tggctgacta attttttta tttatgcaga ggccgaggcc    1860
gcctcggcct ctgagctatt ccagaagtag tgaggaggct tttttggagg cctaggcttt    1920
tgcaaaaagc ttgattcttc tgacacaaca gtctcgaact taaggctaga gccaccatga    1980
ttgaacaaga tggattgcac gcaggttctc cggccgcttg ggtggagagg ctattcggct    2040
atgactgggc acaacagaca atcggctgct ctgatgccgc cgtgttccgg ctgtcagcgc    2100
aggggcgccc ggttcttttt gtcaagaccg acctgtccgg tgcctgaat gaactgcagg     2160 acgaggcagc gcggctatcg tggctggcca cgacgggcgt tccttgcgca gctgtgctcg    2220
acgttgtcac tgaagcggga agggactggc tgctattggg cgaagtgccg ggcaggatc     2280 tcctgtcatc tcaccttgct cctgccgaga agtatccat catggctgat gcaatgcggc     2340
ggctgcatac gcttgatccg gctacctgcc cattcgacca caagcgaaa catcgcatcg     2400 agcgagcacg tactcggatg aagccggtc ttgtcgatca ggatgatctg gacgaagagc     2460
atcaggggct cgcgccagcc gaactgttcg ccaggctcaa ggcgcgcatg cccgacggcg    2520
aggatctcgt cgtgacccat ggcgatgcct gcttgccgaa tatcatggtg gaaaatggcc    2580
gcttttctgg attcatcgac tgtggccggc tgggtgtggc ggaccgctat caggacatag    2640
cgttggctac ccgtgatatt gctgaagagc ttggcggcga atgggctgac cgcttcctcg    2700
tgctttacgg tatcgccgct cccgattcgc agcgcatcgc cttctatcgc cttcttgacg    2760
agttcttctg agcgggactc tggggttcga atgaccgac caagcgacgc ccaacctgcc    2820
atcacgatgg ccgcaataaa atatctttat tttcattaca tctgtgtgtt ggttttttgt    2880
gtgaatcgat agcgataagg atccgcgtat ggtgcactct cagtacaatc tgctctgatg    2940
ccgcatagtt aagccagccc cgacacccgc caacacccgc tgacgcgccc tgacgggctt    3000
gtctgctccc ggcatccgct tacagacaag ctgtgaccgt ctccgggagc tgcatgtgtc    3060
agaggttttc accgtcatca ccgaaacgcg cgagacgaaa gggcctcgtg atacgcctat    3120
ttttataggt taatgtcatg ataataatgg tttcttagac gtcaggtggc acttttcggg    3180
gaaatgtgcg cggaacccct atttgtttat ttttctaaat acattcaaat atgtatccgc    3240
tcatgagaca ataaccctga taaatgcttc aataatattg aaaaggaag agtatgagta    3300 ttcaacattt ccgtgtcgcc cttattccct ttttgcggc attttgcctt cctgtttttg    3360
ctcacccaga aacgctggtg aaagtaaaag atgctgaaga tcagttgggt gcacgagtgg    3420
gttacatcga actggatctc aacagcggta agatccttga gttttcgc cccgaagaac     3480 gttttccaat gatgagcact tttaaagttc tgctatgtgg cgcggtatta tcccgtattg    3540
acgccgggca agagcaactc ggtcgccgca tacactattc tcagaatgac ttggttgagt    3600 actccagt cacagaaaag catcttacgg atggcatgac agtaagagaa ttatgcagtg     3660
ctgccataac catgagtgat aacactgcgg ccaacttact tctgacaacg atcggaggac    3720
cgaaggagct aaccgctttt ttgcacaaca tgggggatca tgtaactcgc cttgatcgtt    3780
gggaaccgga gctgaatgaa gccataccaa acgacgagcg tgacaccacg atgcctgtag    3840
caatggcaac aacgttgcgc aaactattaa ctggcgaact acttactcta gcttcccggc    3900
aacaattaat agactggatg gaggcggata agttgcagg accacttctg cgctcggccc    3960
ttccggctgg ctggtttatt gctgataaat ctggagccgg tgagcgtggg tctcgcggta    4020
tcattgcagc actggggcca gatggtaagc cctcccgtat cgtagttatc tacacgacgg    4080
ggagtcaggc aactatggat gaacgaaata gacagatcgc tgagataggt gcctcactga    4140
```

```
ttaagcattg gtaactgtca gaccaagttt actcatatat actttagatt gatttaaaac   4200 ttcatttta atttaaaagg atctaggtga agatccttt tgataatctc atgaccaaaa    4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tcttttccg aaggtaactg    4440 gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg agcctatgg aaaaacgcca    4920 gcaacgcggc ctttttacgg ttcctggcct tttgctggcc ttttgctcac atggctcgac    4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccacccat    5580 tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttccaccca agcatagcaa ctatctttat ttttggcata gttccccat    6360 ctctgcatgc atacaaattt tatgtacttg tggttactgt gtgcttacgt tttgtattt    6420 atagaagatg atgttctcag atagagtcgt aatggatttt cttcccatta tgaagcaata   6480
cccaacaaaa cagagcttgg gttagatttt tctgagaata agaatgacta aacaaaattc   6540
```

```
tctctttttt tcttcttgac agattttctt gaaggtcacg gaggattctg attcaggacc    6600
tctgtttgcg ggtatggtgc tggagccagt ggcttgttcc cttccttgcc tccctcccaa    6660
gttccatctc gaaagtctaa ggggctgggc acagtggctc atgcctgtaa tcccagcaat    6720
ttgggaggcc aaggcagatg gaccacctga gttcgagacc agcctggcca acatggtgaa    6780
accccatctg tactaaaaat acaaaaatta gctaggtgtg gtggcgcgca cctgtaattc    6840
cagctactcg ggaggctgag gcaggagaat cacttgaacc tgggaggcag aggttgcagt    6900
gagcagagat tgtgccactg cactgcagcc tgagcgacaa gagcaaaatc catctcaaaa    6960
aaaaaaaaaa gtctaaggaa aaagtcatga acaacaaag caggcaaata ctcctccata     7020
gtatctgact ccccagtagt aggcattttg catcctagat ggctttgagt gacaaaggaa    7080
taacagactg agttaggtct agatggggac actttggatg aatgaggatt cttacggagg    7140
tcaggttggt agcttcatcc ctcagctcct catgctgtat ccccagtctc tcggcctgcc    7200
atgtcatcat cctcatctcc tcctgtcatc tccaccaggc ctctgatcca tctctgtctg    7260
catgagtgac agctggcaga gtccttaatg tttatcaaat acaactcaga cgtcagtctc    7320
ctggcccctt tgagatcaac ataaaatcat tttgaaccct tatttagtgg tctatgggct    7380
ttgaaaacat ggggaccaaa attcctgtgg attctagaag tctctcttct acatgtgtca    7440
gcctgggcac caactagctc cttccatgaa cttttatcaa acccacagcc acacaaagca    7500
tgtgtgagtg tagcagagtt tacagcagag ggtggagggt ggggagatag atgtgtggaa    7560
gggttacctg ccacacaaac agaaaccact tctgatagaa cacgaggtgt ccacccacac    7620
tgtaaaatcc tctcctggta caggcaaagc tttgcagcga ttctcctttg ctgcccctgg    7680
gctcctaaca cctcctaaac caccagttac ctccttcttt ccagtgtggc atatttcagt    7740
gttttcctgt tggagtgttt cctttctatg tggattctgg aatcagctct taagataact    7800
tggttttcat ctttcttcat aatgatccca aacatctatc tactatgcct agaactacca    7860
atggacacat ataccagccc agatatgctt cagcccatcc cagtacatcg catggtgacc    7920
aaaagatgta gtcgtcctgg cacagtgggt gtggggcagg aagcagtcct ctccagggga    7980
cagcagcaat tcaccacaga acccaagttt cttcaagct ctgctgacac agaaattgaa      8040
taatctcagc tcacccaatg tcaaagactc atattaacca agaccagaat gaaaatatgc    8100
taatttatat cagaagcttt gctggattca agagttaggg ccttttacct gtgcagaata    8160
ttccttcttg ataaataggc cctctcagga gaataaatta cacatcagag gactgtttag    8220
tcagcatagg catagaacag gatgttccaa agatacagtc aaggggagtg ggtaagagtg    8280
tagcctctgg agtgaggccg accaaatatc aaacctgagc ttcataattt gcaaactaac    8340
tggctttggg taagtacata gcctctttgt acctgtttcc ccatctgcaa aatggagata    8400
ataatagcat ctacctgtag cattgttgag agaattaagt gagttaatgc ttgccgactt    8460
ataacacagt atacgatcac tgattaagac ttagcaactc taaactaaat gtttacaaac    8520
catctcttac ctcaaagcac ttaacatcca ttgtcttatt tgattatcac tgtaatctta    8580
tgaagcaggc agggcagggg tctgccccat ctgggggaa ctgagctcac agaggttgga     8640
gggtttgcct aaagtcaccc aggccactgg gtctcactct ctggtcttag ctctgtaatc    8700
taggatgctc aatgccacac tctcagccac ttttcagatg gctaagtaca tttgttttga    8760
gttagctcag tctcagagga tgacattttc tgatcttgtc tccagtgttt aaatgaacct    8820
gtagctgtgc attggggtca cacaatgcgt ggcatggaga gggtctgtgg ctgactgcca    8880
```

```
cggttactac gtgaaaccat cattacagca gttactactg ttactgcctg agaacatcat    8940
tacaagactg aacgaaggga tcaacatgga aatgataaca aaaaaaccaa agtaactgtt    9000
ttaaggaaag gctagcatcg ggaagaagaa gagagaagaa gagaagaaga aaagggctcc    9060
ctgcttctaa tgagtaaagg cagctcccta agcttctgca gcccttcatt atttattggg    9120
taacaggagg aaggagcagg aggtaatgat tgggtcagct gcttaaatga tcacgggttc    9180
atgttgttac tgacagattt caattatgcc taatcataag aaacatttgt gcagcctcca    9240
acaagggtca atgccacttc tgaaggggtg actcatagtc agtaactaga aagcagcaga    9300
tagctaggga caaactggcg attctgaata ggcctggaac ccttagctct ggccaggtca    9360
gtgggctcca gtcaggatgg agccttcagg gagagatcaa agctcagagg tttgagatga    9420
tatcagccag caaagaggag gggcagtagg gatcctccca gagggagggc cagccataga    9480
agacatcaaa tctgagcccg gatcaggaga aggagcctgc agaactgggg ctctggcacc    9540
gagaacctgc agaacttcgc ccctctgagt gcaggtgcca gggctggggc tgccacccag    9600
ccttcgcatc ccaggcctgg cacgtcatag gtaaatgtag ttgaaaggat gactgagctg    9660
atccaattcc ctttacaact gtccttgtcc tgggggactt gaggagggtt aagaaagcag    9720
ctggggacca accaacagtc ctctaggctc tccatgtcca gcaatagttg ttcagcaaat    9780
gagcattaat cagtgactat aaactgtagc ttcaacataa ccgacaactt gcaatggttt    9840
ctagagcatg ctcccatgtg ttatctcatt taaatttcca aaccaatcct gtgaaatgtt    9900
cttttttttt ttcttttttt tttttttgag atagagtttt gctctgtcac ccaggctgga    9960
atacagcggc tcgatcatag ctcactgcag ccttgacctc ctgggcccaa ggggtcctcc   10020
cacctcagcc tcccaagtag ctgggactac aggcacacgc caccgtgcct ggctaatttc   10080
ttttctagtt gtttgtagag acagggtctc cctatgttgt acaggctgat ctgaaactcc   10140
tggggtcaat caatcctcct ggcttggcct cccaaagtgc tgggattaca ggcatgagcc   10200
accatgcctt cattttacag ataagaagtc tgagaaaact cagatttagg cagattgagt   10260
cacttcccca aatttatgta tcttgtaaga atccatattc aaacctcagt cccctaactc   10320
ttagttcatt acttttttcta ccacttctca gtatcctcta agaattcaga agaaccaca   10380 tcgactctga tttttcattt gtttaagtac acaggtaata ggtgaatgta ttttgttgtt   10440
taaaaattca tataatacac aaaaggctaa agtctcgctt cccacttcct ctcccctttc   10500
tacccaactc tgcctcccca gggagagctt ctgctgacag tcggtggaca ttcttttcaga   10560 gttttacaat tatgtgtgtg tgtgtacata agatgtcagt ttttctttgt gtaggataca   10620
tgaacatgaa ttttaaacat aaatgtgagt gtattacaca tattgaccag caccttagtt   10680
tttttgtttg tttgtttggt tttctttgtg ctgtttgaga aggagtcttg ctctgtcacc   10740
caggctggag tgcagtcttg caatctcggc ttacgcaacc tccacctcct gggttcaagt   10800
gattctcctg cctcagcctc ccgagtagtt gggattacag gtgcctgcca ccatgcctgg   10860 ctaattttg tattttgta gagagggggt ttcactatgt aggtcaagct ggtctcaaac    10920
tgctgacctc aaatgatcca tccacctcag cctcccaaag tgctgagatg acaggcgtga   10980
gcctccgtgc ccagccagtt ttgttttttt attaaccaag ttacgtattt taaacttctc   11040
catgtcaatg cttttagagc tattttgttc tctttaatgt taatagagaa ttttaaggca   11100
atttcaggtg aatctataca atttctctgt ataagtaatt tacactagaa atagatttt    11160 ataaagatga ttaagctacc agcctggtat ttcattgctg acttaaatga agaggaaaat   11220
caatgctgta agggaaaaaa aaaatggcat tagagatcca gaccttatag gcatttttcca   11280
```

```
aattattaat tcaatctctc aaaacaggtg gcgctcagca gaaaagagaa aacgtcaacc    11340
cccgacaccc ctgcttgggt cccagagaga aggctggaca gacaccccag gactccaatg    11400
tctgctcccc aggggcgccg gctgctcacc cagagggcca gcctccccca gagccagagt    11460
gcccaggccc gcagctcaac acggggacac agctggtcct ccagcatgtg caggcgctgc    11520
tggtcaagag attccaacac accatccgca gccacaagga cttcctggcg caggtactat    11580
tgtcggtcgg tgtttagctg agctcagtgg ctcctctccc agccttcccc tcctctcctg    11640
agtgttcctt caggcatggg ttataactca gcaaggagca ccctctttag attctgctgg    11700
ttttgtttcc tgctttccaa acccttatct tgattcttgg taacatgaat cttctttgta    11760
agttggacct cccctagcaa agaaaataga ataatagtga aatgttaat attgttttta     11820
tttttacagt gagggataaa gtcatgtttt cattcattt tgcagtgacc ctacatatca     11880
aaatcattgc cctctttttt cttttaatgt tgtttaattt agaaaaagaa gctctggttt    11940
aaagaacagt gagtcacgtg acttgctctt tgaaatgccc tttgaagtct ggctgaacac    12000
tgggctgcat tcagattctt cagtggccac cagaacattc tgttttcttc tgcacatctt    12060
acctttgcac accctgctta ttatgttccc ccagaagccc aaccctctcc accaggggct    12120
gattaggagg ctgcaggata aatgtttaaa agaatgaaga tgtgtgtgca cgcgcacgtg    12180
tgacatctcc atgccacagt catgtttatt ccacgtctat tctcccacag atcgtgctcc    12240
cggctacctt tgtgttttg gctctgatgc tttctattgt tatccctcct tttggcgaat     12300
accccgcttt gacccttcac ccctggatat atgggcagca gtacaccttc ttcaggtgcg    12360
cggactcggg gtcaccattc tcctctgtgg gtttgggaca cctgggtcac atgctgctta    12420
gaagggccct gaccttccca cttcactggg accttcacca atgagagagg ggagggtct     12480
ttgggctgcc tgcagaaagg aacttaatgt atctgccact gcttggaaag gcgatcctag    12540
tggacaggca ggactgcttg ggaaggccga atggggaaag gaatgcaaag cttaggtgaa    12600
tgggttgaag cgccatcttt ttgaggcata ggtgacatgc catcagacca ctgcgagtgt    12660
tcaggcagcc taccgcactc ccaggagagc tagcgccatc ccaaggcagc attcggtgcc    12720
tccaatacat acctggcaca cagcagctat ccagtaaagg ctctgagttg catgatgttg    12780
gcacgcgcct gctctgtccc agtcacatgt ctcactctgt ctagcatgga tgaaccaggc    12840
agtgagcagt tcacggtact tgcagacgtc ctcctgaata agccaggctt tggcaaccgc    12900
tgcctgaagg aagggtggct tccgtaagtg cctacgcgcc cctgtcctaa gaagactagc    12960
tcccctggga ggacccaacg gtgggttcaa gatggcaggc gttggggagg ccccactcaa    13020
tcctgctctg ctggtcactt ccatgtctct gaccagcact ccccaacct ctccttccac     13080
acttgtgtgc agggacattc actacctcct aggaagcccc cacaccactg gacagctcta    13140
tatttctcag catagaagtt ctatgttgag ttgacagatg attccccata acttatttga    13200
aaggcctctg agcagggagg gagggaaata gggttatgct attgtgtgat tgggccttga    13260
atggcgtgag tgacacagtg gccagtactt tgtgatagtt gtgagtctgg agaagggagt    13320
tagcgaaggc cattgacatc caccaggaat cacccagctt tc                      13362
```

<210> SEQ ID NO 24
<211> LENGTH: 20
<212> TYPE: DNA
<213> ORGANISM: Artificial Sequence
<220> FEATURE:
<223> OTHER INFORMATION: RT_PCR primer

```
<400> SEQUENCE: 24
gaaggtcacg gaggattctg                                              20

<210> SEQ ID NO 25
<211> LENGTH: 20
<212> TYPE: DNA
<213> ORGANISM: Artificial Sequence
<220> FEATURE:
<223> OTHER INFORMATION: RT-PCR primer

<400> SEQUENCE: 25
cctggcttat tcaggaggac                                              20

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26
atctgctgcg gcaagaac                                                18

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
aggtgtaggg gatgggagac                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
actgggacga catggagaag                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tctcagctgt ggtggtgaag                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
atgttcctgt ccgtcaggtc                                              20
```

ANTISENSE OLIGONUCLEOTIDES RESCUE ABERRANT SPLICING OF ABCA4

FIELD OF THE INVENTION

The invention relates to the fields of medicine and immunology. In particular, it relates to novel antisense oligonucleotides that may be used in the treatment, prevention and/or delay of an ABCA4-associated condition.

BACKGROUND OF THE INVENTION

Autosomal recessive mutations in ABCA4 cause Stargardt disease, a progressive disorder characterized by central vision loss and often leading to complete blindness. A typical hallmark of Stargardt disease is the presence of many yellow spots (flecks) distributed throughout the fundus of the patients. The ABCA4 gene is comprised of 50 exons and encodes a protein consisting of 2273 amino acids. This protein is expressed in the outer segments of cone and rod photoreceptor cells and plays an important role in the removal of waste products following phototransduction.

Besides STGD1, variants in ABCA4 can also lead to other subtypes of retinal disease ranging from bull's eye maculopathy to autosomal recessive cone-rod dystrophy (arCRD; Cremers et al, 1998; Maugeri et al, 2000) and pan-retinal dystrophies (Cremers et al, 1998; Martinez-Mir et al, 1998), depending on the severity of the alleles.

Biallelic ABCA4 variants can be identified in approximately 80% of the cases with STGD1 (Allikmets et al, 1997; Fujinami et al, 2013; Lewis et al, 1999; Maugeri et al, 1999; Rivera et al, 2000; Schulz et al, 2017; Webster et al, 2001; Zernant et al, 2011; Zernant et al, 2017), and 30% of cases with arCRD (Maugeri et al, 2000), after sequencing coding regions and flanking splice sites. In general, individuals with arCRD or pan-retinal dystrophy carry two severe ABCA4 alleles, whereas individuals with STGD1 carry two moderately severe variants or a combination of a mild and a severe variant (Maugeri et al, 1999; van Driel et al, 1998). It has been hypothesized that the majority of the missing ABCA4 variants in STGD1 patients reside in intronic regions of the gene, and indeed, over the last few years, several groups have demonstrated the existence of such deep-intronic variants (Bauwens et al, 2015; Bax et al, 2015; Braun et al, 2013; Lee et al, 2016; Schulz et al, 2017; Zernant et al, 2014). Recently, we discovered a recurrent variant in ABCA4, c.4253+43G>A that affects ABCA4 pre-mRNA splicing by skipping the adjacent exon 28 from a proportion of ABCA4 transcripts, a process that can be accompanied by co-skipping of adjacent exons such as exon 27 or exon 29.

The fact that a considerable amount of the mutations in ABCA4 affect pre-mRNA splicing of ABCA4, renders it an attractive target for antisense oligonucleotide (AON)-based splice modulation therapy. Accordingly, there is an urge to develop AONs for splice modulation of the ABCA4 gene to enable expression of a functional ABCA4 protein in subjects suffering from Stargardt disease.

SUMMARY OF THE INVENTION

In a first aspect, the invention provides for an ABCA4 exon 28 retention molecule that binds to and/or is complementary to a polynucleotide with the nucleotide sequence as shown in SEQ ID NO:4, preferably the molecule is complementary to a polynucleotide with SEQ ID NO:5, more preferably the molecule is complementary to a polynucleotide with SEQ ID NO:6.

In a second aspect, the invention provides for an antisense oligonucleotide ABCA4 exon 28 retention molecule wherein the antisense oligonucleotide comprises or consists of a sequence selected from the group consisting of SEQ ID NO: 17, SEQ ID NO: 18, SEQ ID NO: 19, SEQ ID NO: 20, and SEQ ID NO: 21, preferably the antisense oligonucleotide comprises or consist of SEQ ID NO:19.

In a third aspect, the invention provide for a set of ABCA4 exon 28 retention molecules comprising at least two antisense oligonucleotide according to the invention, wherein preferably the set comprises or consists of at least two antisense oligonucleotides selected from the group consisting of SEQ ID NO: 17, SEQ ID NO: 18, SEQ ID NO: 19, SEQ ID NO: 20, and SEQ ID NO: 21.

In a fourth aspect, the invention provides for a viral vector expressing an ABCA4 exon 28 retention molecule as defined herein.

In a fifth aspect, the invention provides for a pharmaceutical composition comprising an ABCA4 exon 28 retention molecule as defined herein.

In a sixth aspect, the invention provides for a ABCA4 exon 28 retention molecule as defined herein use as a medicament, preferably for use as a medicament for treating an ABCA4 related disease or a condition requiring modulating splicing of ABCA4 or for use in a method of treating an ABCA4 related disease or a condition requiring modulating splicing of ABCA4.

DETAILED DESCRIPTION OF THE INVENTION

By definition, antisense oligonucleotides (AONs) are substantially complementary (antisense) to their target, allowing them to bind to the corresponding pre-mRNA molecule, thereby, without being bound by theory, preventing the binding of proteins essential for splicing. Usually, this lack of binding results in the skipping of the targeted exon, as the present inventors have previously shown for the c.4539+1100A>G, c.4539+1106C>T, c.4539+2001G>A and c.4539+2028C>T mutations in ABCA4 (WO2018/109011). However, by fusing the sequence of the AON to elements that recruit splice enhancers, AONs can also be employed to force the inclusion of exons that due to mutations are absent in the mutant transcripts of the corresponding gene.

The present inventors have identified one ABCA4 variant, c.4253+43G>A, that is very common in the population, present in ~0.4% of all individuals worldwide. Although this mutation is not fully penetrant (not all individuals with this mutation will get STGD1), it is one of the most common mutations in patients with STGD1, in particularly those with a relatively late-onset. The inventors have demonstrated that, in patients with this mutation, the amount of ABCA4 transcripts that contain exon 28 is lower compared to control individuals, indicating that this mutation results in a partial skipping of exon 28 from the ABCA4 mRNA. Occasionally, this process is accompanied by co-skipping of adjacent exons such as exon 27 or exon 29.

Surprisingly, it has now been demonstrated that specific AONs are able to redirect the aberrant splicing of ABCA4 that is caused by the intronic c.4253+43G>A mutation leading to the inclusion of exon 28.

Accordingly, in a first aspect the invention provides an ABCA4 exon 28 retention molecule that binds to and/or is complementary to a polynucleotide with the nucleotide sequence as shown in SEQ ID NO:4, preferably the molecule is complementary to a polynucleotide with SEQ ID NO:5, more preferably the molecule is complementary to a polynucleotide with SEQ ID NO:6 or a part thereof.

The term "exon retention" is herein defined as inducing, producing or increasing production within a cell of a mature mRNA that does retain a particular exon that should be present in the mature mRNA without (aberrant) exon skipping. Exon retention is achieved by providing a cell expressing the pre-mRNA of said mature mRNA with an AON molecule capable of interfering with sequences such as, for example, alternative splice sites upstream or downstream of the regular splice sites.

An AON according to the invention is said to induce exon retention if the retention percentage as measured, preferably by real-time quantitative RT-PCR analysis, is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of mature mRNA.

The term "antisense oligonucleotide" or "AON" is understood to refer to an oligonucleotide molecule comprising a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The term "substantially complementary" used in the context of the invention indicates that some mismatches in the antisense sequence are allowed as long as the functionality, i.e. inducing exon retention is maintained. Preferably, the complementarity is 90% to 100%. In general, this allows for 1 or 2 mismatches in an AON of 20 nucleotides or 1, 2, 3 or 4 mismatches in an AON of 40 nucleotides, or 1, 2, 3, 4, 5 or 6 mismatches in an AON of 60 nucleotides, etc. Optionally, said AON may further be tested by transfection into retina cells of patients. Retention of an exon may be assessed by RT-PCR (such as e.g. described in EP1619249). The complementary regions are preferably designed such that, when combined, they are specific for the exon in the pre-mRNA. Such specificity may be created with various lengths of complementary regions, as this depends on the actual sequences in other (pre-)mRNA molecules in the system. The risk that the AON will also be able to hybridize to one or more other pre-mRNA molecules decreases with increasing size of the AON. It is clear that AONs comprising mismatches in the region of complementarity but that retain the capacity to hybridize and/or bind to the targeted region(s) in the pre-mRNA, can be used in the invention. However, preferably at least the complementary parts do not comprise such mismatches as AONs lacking mismatches in the complementary part typically have a higher efficiency and a higher specificity than AONs having such mismatches in one or more complementary regions. It is thought, that higher hybridization strengths, (i.e. increasing number of interactions with the opposing strand) are favorable in increasing the efficiency of the process of interfering with the splicing machinery of the system.

An AON according to the invention preferably does not contain a stretch of CpG, more preferably does not contain any CpG. The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an AON according to the invention by detecting the presence of a neutralizing antibody and/or an antibody recognizing said AON using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said AON using a standard immunoassay. The AON according to the invention furthermore preferably has acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/-cail/biotool/oligo/index) for single stranded RNA using the basic Tm and the nearest neighbor model), and/or the free energy of the AON-target exon complex (using RNA structure version 4.5). If a Tm is too high, an AON is expected to be less specific. An acceptable Tm and free energy depend on the sequence of the AON. Therefore, it is difficult to give preferred ranges for each of these parameters. An acceptable Tm may be ranged between 35 and 70° C. and an acceptable free energy may be ranged between 15 and 45 kcal/mol. The skilled person may therefore first choose an AON as a potential therapeutic compound as binding and/or being complementary to SEQ ID NO: 4, or a part thereof as defined later herein. The skilled person may check that said AON is able to bind to said sequences as earlier defined herein. Optionally in a second step, he may use the invention to further optimize said AON by checking for the absence of CpG and/or by optimizing its Tm and/or free energy of the AON-target complex. He may try to design an AON wherein few, preferably, no CpG and/or wherein a more acceptable Tm and/or free energy are obtained by choosing a distinct sequence of ABCA4 (including SEQ ID NO: 4 or a part thereof) to which the AON is complementary. Alternatively, if an AON complementary to a given stretch within SEQ ID NO: 4, comprises a CpG, and/or does not have an acceptable Tm and/or free energy, the skilled person may improve any of these parameters by decreasing the length of the AON, and/or by choosing a distinct stretch within any of SEQ ID NO: 4 to which the AON is complementary and/or by altering the chemistry of the AON.

An AON for redirecting splicing according to the invention may comprise one of more RNA residue (ribonucleotide), or one or more DNA residue (deoxyribonucleotide), and/or one or more nucleotide analogues or equivalents, as will be further detailed herein below.

For the purpose of the invention, the terms "aberrant ABCA4 exon 28" of "aberrant exon 28" are considered to be synonymous, and considered to mean the presence of a mutation in exon 28 (SEQ ID NO:4) of the ABCA4 gene, resulting in an ABC4A mRNA with at least one substitution, deletion or insertion in exon 28 of ABCA4 (SEQ ID NO:4).

In all embodiments of the invention, an exon retention molecule is preferably a nucleic acid molecule, preferably an oligonucleotide. Preferably, an exon retention molecule according to the invention is a nucleic acid molecule, preferably an oligonucleotide, which is complementary or substantially complementary to a nucleotide sequence as shown in in SEQ ID NO:4, preferably the molecule is complementary to a polynucleotide with SEQ ID NO:5, more preferably the molecule is complementary to a polynucleotide with SEQ ID NO:6 or a part thereof of ABCA4.

A preferred ABCA4 exon 28 retention molecule according to the invention is a nucleic acid molecule that comprises or consists of an antisense oligonucleotide that is complementary to the polynucleotide wherein the antisense oligonucleotide has a length from about 8 to about 100 nucleotides, more preferred 10 to about 40 nucleotides, more preferred from about 12 to about 30 nucleotides, more preferred from about 14 to about 28 nucleotides, nucleotides, most preferred about 20 to 24 nucleotides, such as 20 nucleotides, 21 nucleotides, 22 nucleotides, 23 nucleotides, 24 nucleotides or 25 nucleotides.

In certain embodiments, the invention provides a ABCA4 exon 28 retention molecule, wherein the antisense oligonucleotide comprises or consists of a sequence selected from the group consisting of SEQ ID NO: 17, SEQ ID NO: 18, SEQ ID NO: 19, SEQ ID NO: 20, and SEQ ID NO: 21, preferably the antisense oligonucleotide comprises or consist of SEQ ID NO:19.

In certain embodiments, wherein the antisense oligonucleotide comprises or consists of a sequence selected from the group consisting of SEQ ID NO: 17, SEQ ID NO: 18, SEQ ID NO: 19, SEQ ID NO: 20, and SEQ ID NO: 21, preferably the antisense oligonucleotide comprises or consist of SEQ ID NO:19, the antisense oligonucleotide has a length of 8 to 100 nucleotides, preferably a length of 10 to 40 nucleotides, more preferably a length of 12 to 30 nucleotides, most preferably the retention molecule has a length of 18 to 24 nucleotides, such as 18, 19, 20, 21, 22, 23 or 24 nucleotides.

In a preferred embodiment, the invention provides for an ABCA4 retention molecule comprising or preferably consisting of the AON SEQ ID NO: 19. It was found that this molecule was very efficient in redirecting the aberrant splicing of ABCA4 that is caused by the intronic c.4253+43G>A. This preferred exon retention molecule of the invention comprising SEQ ID NO: 19, preferably comprises from about 8 to about 100 nucleotides, more preferred 10 to about 40 nucleotides, more preferred from about 12 to about 30 nucleotides, more preferred from about 14 to about 28 nucleotides, nucleotides, most preferred about 20 to 24 nucleotides, such as 20 nucleotides, 21 nucleotides, 22 nucleotides, 23 nucleotides, 24 nucleotides or 25 nucleotides It is preferred that an AON for redirecting splicing according to the invention comprises one or more residues that are modified to increase nuclease resistance, and/or to increase the affinity of the antisense oligonucleotide for the target sequence. Therefore, in a preferred embodiment, the AON comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents.

Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report, demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen et al., 1991). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar, 2005). Since the backbone of a PNA molecule contains no charged phosphate groups, PNA-RNA hybrids are usually more stable than RNA-RNA or RNA-DNA hybrids, respectively (Egholm et al., 1993). A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent according to the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent according to the invention comprises one or more sugar moieties that are mono- or disubstituted at the 2', 3' and/or 5' position such as a —OH; —F; substituted or unsubstituted, linear or branched lower (Cl-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al., 2001). These substitutions render the nucleotide analogue or equivalent RNase H and nuclease resistant and increase the affinity for the target RNA. In another embodiment, a nucleotide analogue or equivalent according to the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON according to the invention has at least two different types of analogues or equivalents.

Accordingly, in a preferred embodiment an ABCA4 exon 28 retention molecule according to the invention comprises a 2'-0 alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. [Claim 6]

It will also be understood by a skilled person that different antisense oligonucleotides can be combined for efficient inclusion of the aberrant exon 28. In a preferred embodiment the invention comprises a set of ABCA4 exon 28 retention molecules comprising at least two ABCA4 exon 28 retention molecules according to the invention. Preferably wherein of ABCA4 exon 28 retention molecules set comprises or consists of at least two, at least three, at least four antisense oligonucleotides selected from the group consisting of SEQ ID NO: 17, SEQ ID NO: 18, SEQ ID NO: 19, SEQ ID NO: 20, and SEQ ID NO: 21. For example, such set may comprise or consist of:

antisense oligonucleotide SEQ ID NO: 17 and antisense oligonucleotide SEQ ID NO: 18,
antisense oligonucleotide SEQ ID NO: 17 and antisense oligonucleotide SEQ ID NO: 19,
antisense oligonucleotide SEQ ID NO: 17 and antisense oligonucleotide SEQ ID NO: 20
antisense oligonucleotide SEQ ID NO: 17 and antisense oligonucleotide SEQ ID NO: 21,
antisense oligonucleotide SEQ ID NO: 18 and antisense oligonucleotide SEQ ID NO: 19,
antisense oligonucleotide SEQ ID NO: 18 and antisense oligonucleotide SEQ ID NO: 20,
antisense oligonucleotide SEQ ID NO: 18 and antisense oligonucleotide SEQ ID NO: 21,
antisense oligonucleotide SEQ ID NO: 19 and antisense oligonucleotide SEQ ID NO: 20,
antisense oligonucleotide SEQ ID NO: 19 and antisense oligonucleotide SEQ ID NO: 21, or
antisense oligonucleotide SEQ ID NO: 20 and antisense oligonucleotide SEQ ID NO: 21.

Stargardt disease (STGD1) usually has an autosomal recessive inheritance caused by biallelic ABCA4 variants. It is thus entirely plausible that patients can carry several ABCA4 mutations thereby requiring a combination of AONs for the treatment of the disease. Accordingly, the invention provides for a composition comprising one or more of the AONs of the invention and optionally, one or more AONs targeting other mutations in ABCA4. For example, the invention provides for a composition comprising an AON of the present invention and an AON described in WO2018/109011.

An AON for redirecting splicing according to the invention may be indirectly administered using suitable means known in the art. It may for example be provided to an individual or a cell, tissue or organ of said individual as such, as a so-called 'naked' AON. It may also be administered in the form of an expression vector wherein the expression vector encodes an RNA transcript comprising the sequence of said AON according to the invention. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an AON for redirecting splicing according to the invention. Accordingly, the invention provides for a viral vector expressing an antisense oligonucleotide according to the invention when placed under conditions conducive to expression of the molecule.

A cell can be provided with an AON for redirecting splicing according to the invention by plasmid-derived antisense oligonucleotide expression or viral expression provided by adenovirus- or adeno-associated virus-based vectors. Expression may be driven by an RNA polymerase II promoter (Pol II) such as a U7 RNA promoter or an RNA polymerase III (Pol III) promoter, such as a U6 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an AON for redirecting splicing according to the invention. Preferred for the invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts, preferably, in the form of a fusion transcript with an U1 or U7 transcript. Such fusions may be generated as previously described (Gorman et al., 1998).

A preferred expression system for an AON for redirecting splicing according to the invention is an adenovirus associated virus (AAV)-based vector. Single chain and double chain AAV-based vectors have been developed that can be used for prolonged expression of antisense nucleotide sequences for highly efficient redirection of splicing. A preferred AAV-based vector, for instance, comprises an expression cassette that is driven by an RNA polymerase III-promoter (Pol III) or an RNA polymerase II promoter (Pol II). A preferred RNA promoter is, for example, a Pol III U6 RNA promoter, or a Pol II U7 RNA promoter.

The invention accordingly provides for a viral-based vector, comprising a Pol II or a Pol III promoter driven expression cassette for expression of an AON for redirecting splicing according to the invention.

An AAV vector according to the invention is a recombinant AAV vector and refers to an AAV vector comprising part of an AAV genome comprising an encoded AON for redirecting splicing according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. A protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector.

More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector.

More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector.

More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector.

A nucleic acid molecule encoding an AON for redirecting splicing according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art, see e.g. (Chiorini et al., 1999) or U.S. Pat. No. 5,139,941, incorporated herein by reference. The AAV helper functions can be supplied on an AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs according to the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

Preferably, an AAV vector according to the invention is constructed and produced according to the method according to Garanto et al., 2016 which is herein incorporated by reference.

A preferred AAV vector according to the invention is an AAV vector, preferably an AAV2/5, AAV2/8, AAV2/9 or AAV2/2 vector, expressing an AON for redirecting splicing according to the invention that is an AON that comprises, or preferably consists of, a sequence that is:
complementary or substantially complementary to a nucleotide sequence consisting of SEQ ID NO:4, preferably the molecule is complementary to a polynucleotide with SEQ ID NO:5, more preferably the molecule is complementary to a polynucleotide with SEQ ID NO:6;
more preferably complementary or substantially complementary to a polynucleotide with a nucleotide sequence selected from the group consisting of SEQ ID NO: 17, SEQ ID NO: 18, SEQ ID NO: 19, SEQ ID NO: 20, and SEQ ID NO: 21.

Improvements in means for providing an individual or a cell, tissue, organ of said individual with an AON for redirecting splicing according to the invention, are anticipated considering the progress that has already thus far been achieved. Such future improvements may of course be incorporated to achieve the mentioned effect on restructuring of mRNA using a method according to the invention. An AON for redirecting splicing according to the invention can be delivered as such as a 'naked' AON to an individual, a cell, tissue or organ of said individual. When administering an AON for redirecting splicing according to the invention, it is preferred that the molecule is dissolved in a solution that is compatible with the delivery method. Retina cells can be provided with a plasmid for antisense oligonucleotide expression by providing the plasmid in an aqueous solution.

Alternatively, a preferred delivery method for an AON for redirecting splicing or a plasmid for expression of such AON is a viral vector or are nanoparticles. Preferably, viral vectors or nanoparticles are delivered to retina or other relevant cells. Such delivery to retina cells or other relevant cells may be in vivo, in vitro or ex vivo; see e.g. Garanto et al, 2016, which is herein incorporated by reference.

Alternatively, a plasmid can be provided by transfection using known transfection agents. For intravenous, subcutaneous, intramuscular, intrathecal and/or intraventricular administration it is preferred that the solution is a physiological salt solution. Particularly preferred in the invention is the use of an excipient or transfection agents that will aid in delivery of each of the constituents as defined herein to a cell and/or into a cell, preferably a retina cell. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constituent as defined herein to a cell, preferably a retina cell. Such excipients have been shown to efficiently deliver an oligonucleotide such as AONs to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N, N, N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such as diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an AON according to the invention, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon retention molecule for use in the current invention to deliver it for the prevention, treatment or delay of ABCA4-related disease or condition. "Prevention, treatment or delay of an ABCA4-related disease or condition" is herein preferably defined as preventing, halting, ceasing the progression of, or reversing partial or complete visual impairment or blindness that is caused by a genetic defect in the ABCA4 gene.

In addition, an AON for redirecting splicing according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an AON for redirecting splicing according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be suitably formulated in one single combination or composition or preparation. Depending on their identity and specific features, the skilled person will know which type of formulation is the most appropriate for each constituent as defined herein. In a preferred embodiment, the invention provides a composition or a preparation which is in the form of a kit of parts comprising an AON for redirecting splicing according to the invention and a further adjunct compound as later defined herein.

If required and/or if desired, an AON for redirecting splicing according to the invention or a vector, preferably a viral vector, according to the invention, expressing an AON for redirecting splicing according to the invention can be incorporated into a pharmaceutically active mixture by adding a pharmaceutically acceptable carrier.

Accordingly, the invention also provides for a composition, preferably a pharmaceutical composition, comprising an AON for redirecting splicing according to the invention, or a viral vector according to the invention and a pharmaceutically acceptable excipient. Such composition may comprise a single AON for redirecting splicing or viral vector according to the invention, but may also comprise multiple, distinct AONs for redirecting splicing or viral vectors according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

A preferred route of administration is through intra-vitreal injection of an aqueous solution or specially adapted formulation for intraocular administration. [claim 10] EP2425 814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct AONs for redirecting splicing according to the invention are used, the concentration or dose defined herein may refer to the total concentration or dose of all oligonucleotides used or the concentration or dose of each exon rentention molecule used or added. Therefore, in an embodiment, there is provided a composition wherein each or the total amount of AONs for redirecting splicing according to the invention used is dosed in an amount ranged from 0.01 and 20 mg/kg, preferably from 0.05 and 20 mg/kg per eye. A suitable intravitreal dose is provided and comprises between 0.05 mg and 5 mg, preferably between 0.1 and 1 mg of total exon 28 retention molecule per eye, such as about per eye: 0.1, 0.2, 0.3, 0.4, 0.5, 0.6, 0.7, 0.8, 0.9 or 1.0 mg.

A preferred AON for redirecting splicing according to the invention, is for the treatment of an ABCA4-related disease or condition of an individual. In all embodiments of the invention, the term "treatment" is understood to include the prevention and/or delay of the ABCA4-related disease or condition. An individual, which may be treated using an AON for redirecting splicing according to the invention may already have been diagnosed as having an ABCA4-related disease or condition. Alternatively, an individual which may be treated using an AON for redirecting splicing according to the invention may not have yet been diagnosed as having a ABCA4-related disease or condition but may be an individual having an increased risk of developing a ABCA4-related disease or condition in the future given his or her genetic background. A preferred individual is a human being. In all embodiments of the invention, the ABCA4-related disease or condition preferably is Stargardt disease.

Accordingly, the invention further provides for an AON for redirecting splicing according to the invention, or a viral vector according to the invention, or a (pharmaceutical) composition according to the invention for use as a medicament, preferably as a medicament for the treatment of an ABCA4-related disease or condition requiring modulating splicing of ABCA4 and for use as a medicament for the prevention, treatment or delay of an ABCA4-related disease or condition. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for treating an ABCA4-related disease or condition requiring modulating splicing of ABCA4. Each feature of all medical use embodiment herein has earlier been defined herein and is preferably such feature as earlier defined herein.

The invention further provides for, a method of treatment of an ABCA4-related disease or condition requiring modulating splicing of ABCA4, comprising said method comprising contacting a cell of said individual with an AON for redirecting splicing according to the invention, a vector according to the invention or a (pharmaceutical) composition according to the invention. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for the preparation of a medicament for the treatment of an ABCA4-related disease or condition requiring modulating splicing of ABCA4. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for the preparation of a medicament. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention or a method of treatment according to the invention wherein the ABCA4-related disease or condition is Stargardt disease.

Treatment in a use or in a method according to the invention is preferably at least once, and preferably lasts at least one week, one month, several months, one year, 2, 3, 4, 5, 6 years or longer, such as life-long. Each AON for redirecting splicing according to the invention or equivalent thereof as defined herein for use according to the invention may be suitable for direct administration to a cell, tissue and/or an organ in vivo of individuals already affected or at risk of developing an ABCA4-related disease or condition, and may be administered directly in vivo, ex vivo or in vitro. The frequency of administration of an AON, composition, compound or adjunct compound according to the invention may depend on several parameters such as the severity of the disease, the age of the patient, the mutation of the patient, the number of AON for redirecting splicing according to the invention (i.e. dose), the formulation of the AON, composition, compound or adjunct compound according to the invention, the route of administration and so forth. The frequency of administration may vary between daily, weekly, at least once in two weeks, or three weeks or four weeks or five weeks or a longer time period.

Dose ranges of an AON, composition, compound or adjunct compound according to the invention are preferably designed on the basis of rising dose studies in clinical trials (in vivo use) for which rigorous protocol requirements exist. An AON according to the invention may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nM. If multiple distinct AONs are used, this concentration or dose may refer to the total concentration or dose of the AONs or the concentration or the dose of each AON added.

In a preferred embodiment, a viral vector, preferably an AAV vector as described earlier herein, as delivery vehicle for a molecule according to the invention, is administered in a dose ranging from $1\times10^{09}$-$1\times10^{17}$ virus particles per injection, more preferably from $1\times10^{10}$-$1\times10^{12}$ virus particles per injection.

The ranges of concentration or dose of AONs as depicted above are preferred concentrations or doses for in vivo, in vitro or ex vivo uses. The skilled person will understand that depending on the AONs used, the target cell to be treated, the gene target and its expression levels, the medium used and the transfection and incubation conditions, the concentration or dose of AONs used may further vary and may need to be optimized any further.

An AON for redirecting splicing according to the invention, or a viral vector according to the invention, or a composition according to the invention for use according to the invention may be administered to a cell, tissue and/or an organ in vivo of individuals already affected or at risk of developing a ABCA4-related disease or condition, and may be administered in vivo, ex vivo or in vitro. An AON for redirecting splicing according to the invention, or a viral vector according to the invention, or a composition according to the invention may be directly or indirectly administered to a cell, tissue and/or an organ in vivo of an individual already affected by or at risk of developing a ABCA4-related disease or condition, and may be administered directly or indirectly in vivo, ex vivo or in vitro. As Stargardt disease has a pronounced phenotype in retina cells, it is preferred that said targeted cells are retina cells, it is further preferred that said tissue is the retina and it is further preferred that said organ comprises or consists of the eye.

The invention further provides for a method for modulating splicing of ABCA4 in a cell comprising contacting the cell, preferably a retina cell, with an AON for redirecting splicing according to the invention, or a viral vector according to the invention, or a (pharmaceutical) composition according to the invention. The features of this aspect are preferably those defined earlier herein. Contacting the cell with an AON for redirecting splicing according to the invention, or a viral vector according to the invention, or a composition according to the invention may be performed by any method known by the person skilled in the art. Use of the methods for delivery of AONs for redirecting splicing, viral vectors and compositions as described earlier herein is included. Contacting may be directly or indirectly and may be in vivo, ex vivo or in vitro.

Unless otherwise indicated each embodiment as described herein may be combined with another embodiment as described herein.

Definitions

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 5% of the value. The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

DESCRIPTION OF THE SEQUENCES

Figure 1:
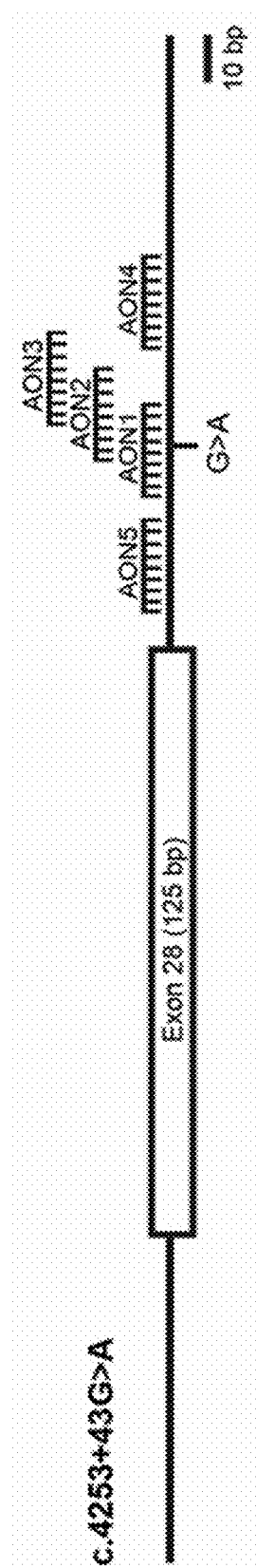
FIG. 1: Schematic representation of the location of the c.4253+43G>A variant and the designed AONs.

| SEQ ID NO: | Name |
|---|---|
| 1 | Genomic DNA sequence ABCA4 |
| 2 | mRNA sequence ABCA4 |
| 3 | ABCA4 Protein sequence |
| 4 | Exon 28 sequence (starting at the last 100 bp of intron 26 to the first 100 bp of intron 29) |
| 5 | Target region in exon 28 (±75 bp) |
| 6 | Target region in exon 28 |
| 7 | AON1 target + 10 |
| 8 | AON1 target + 5 |
| 9 | AON2 target + 10 |
| 10 | AON2 target + 5 |
| 11 | AON3 target + 10 |
| 12 | AON3 target + 5 |
| 13 | AON4 target + 10 |
| 14 | AON4 target + 5 |
| 15 | AON5 target + 10 |
| 16 | AON5 target + 5 |
| 17 | AON1 |
| 18 | AON2 |
| 19 | AON3 |
| 20 | AON4 |
| 21 | AON5 |
| 22 | pCI-Neo-Rho-ABCA4-26-29 |
| 23 | pCI-Neo-Rho-ABCA4-26-29 c.4243 + 43G > A |
| 24 | ABCA4_ex26_Fw PCR primer |
| 25 | ABCA4_ex29_Rv PCR primer |
| 26 | RHO_Fw PCR primer |
| 27 | RHO_Rv PCR primer |
| 28 | ACTB_Fw PCR primer |
| 29 | ACTB_Rv PCR primer |
| 30 | ABCA4_ex31 PCR primer |

EXAMPLES

We have assessed the in vitro efficacy of a number of AONs to redirect splicing of ABCA4 in cells. For this we used midigene constructs, i.e. plasmids that harbour the sequence of a part of the ABCA4 gene, usually the region of interest with or without the mutation, and flanked by at least 100 bp of wild-type ABCA4 sequence on each side. In addition to the midigene assays, we also used photoreceptor precursor cells (PPCs) from a patient with compound heterozygous ABCA4 mutations and heterozygously carrying the c.4253+43G>A mutation to assess the nature of the splice defect associated with this mutation.

Example 1

AON Assessment Using Midigene Construct
Generation of Midigene Splice Constructs A midigene was created including part of the 26 intron, the complete exon 28, and part of exon 29.

This genomic region was cloned into a pCI-Neo-Rhodopsin vector using the Gateway System. The resulting vector (coined pCI-Neo-Rho-ABCA4-26-29 wild-type, SEQ ID NO:22) was used to introduce the c. c.4243+43G>A mutation by site-directed mutagenesis (new vector was coined pCI-Neo-Rho-ABCA4-26-29 c.4243+43G>A SEQ ID NO:23). The control and mutated vectors were validated by Sanger sequencing. The minigenes were then transfected in HEK293T cells, which were harvested 48 h post-transfection and were subjected to RT-PCR analysis in order to detect the splicing defect. Subsequently, these midigene constructs can be transfected in eukaryotic immortalized cells (such as Human Embryonic Kidney cells HEK293T, which were used in this study), and the splice pattern can be studied via RT-PCR analysis. If the mutant construct shows an aberrant splicing pattern, co-transfection of midigenes together with AONs allows to determine the efficacy of the AONs to redirect splicing.

Design Antisense Oligonucleotides

The transfection of midigene pCI-Neo-Rho-ABCA4-26-29 c.4243+43G>A in HEK293T cells showed the skipping of exon 28, which is predicted to result in premature termination of ABCA4 protein synthesis and thus reduced expression of ABCA4 protein levels. Using the sequence of exon 28, several AONs were designed.

AON Assessment

HEK293T cells were transfected with either the wild-type (WT) or c.4253+43G>A mutant (MUD midigene construct. Twenty-four hours later, transfected cells were subdivided in wells to decrease transfection variability. AON was delivered at a final concentration of 0.5 uM. Forty-eight hours post-AON-transfection, cells were harvested and subjected to RNA analysis by RT-PCR. For the RT-PCR, total RNA was isolated by using the NucleoSpin RNA Clean-up Kit (catalog no., 740955-50; Macherey-Nagel, Duren, Germany) according to the manufacturers protocol. RNA was quantified and cDNA was synthesized from 1 µg RNA by using the iScript cDNA synthesis kit (catalog no., 1708891; Bio-Rad, Hercules, Calif.) following the manufacturers instructions.

Figure 2:
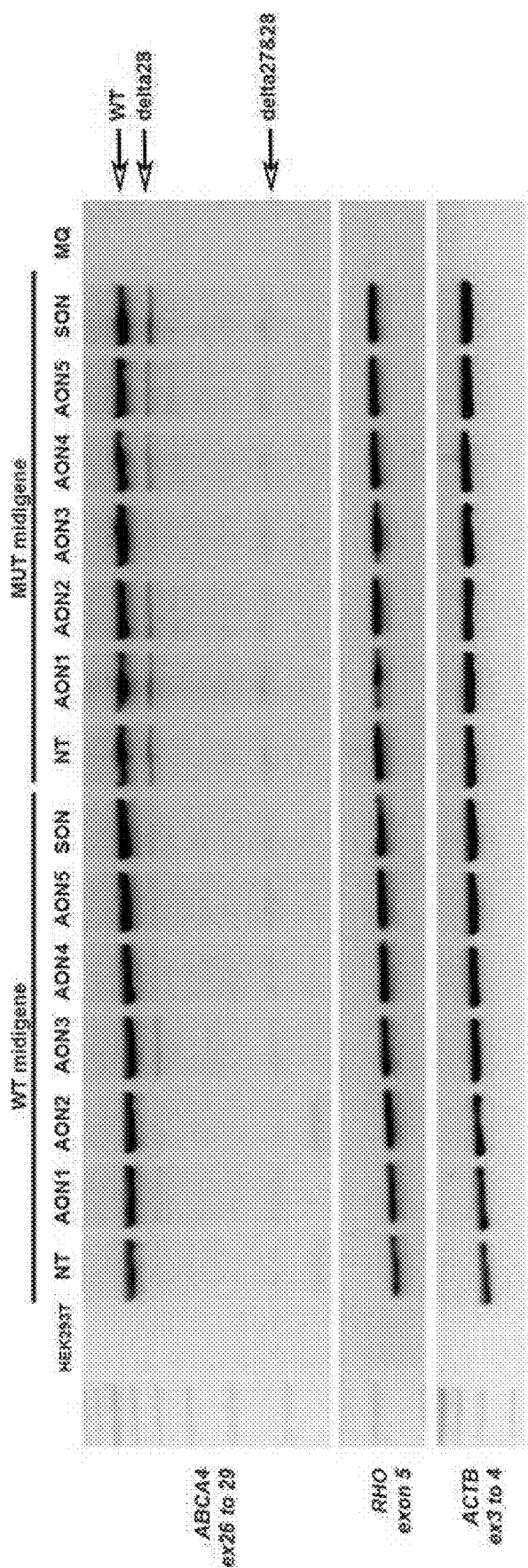
FIG. 2: RT-PCR analysis of AONs in WT and MUT midigenes in HEK293T cells transfected with Wild-type (WT) or c.4253+43G>A mutant (MUD constructs. Sense oligonucleotide (SON) was used as a control.

In the RT-PCR ABCA4 was amplified from exon 26 to 29 using the primers represented by SEQ ID NOs: 24 and 25. RHO was included as transfection control and ACTB as loading control (primers used SEQ ID NOs:26-29). SON (sense oligonucleotide) was used as a control. All tested AONs were capable of redirecting splicing (FIG. 2).

Example 2

Semi-Quantification of the Transcripts Identified by RT-PCR

Figure 3:
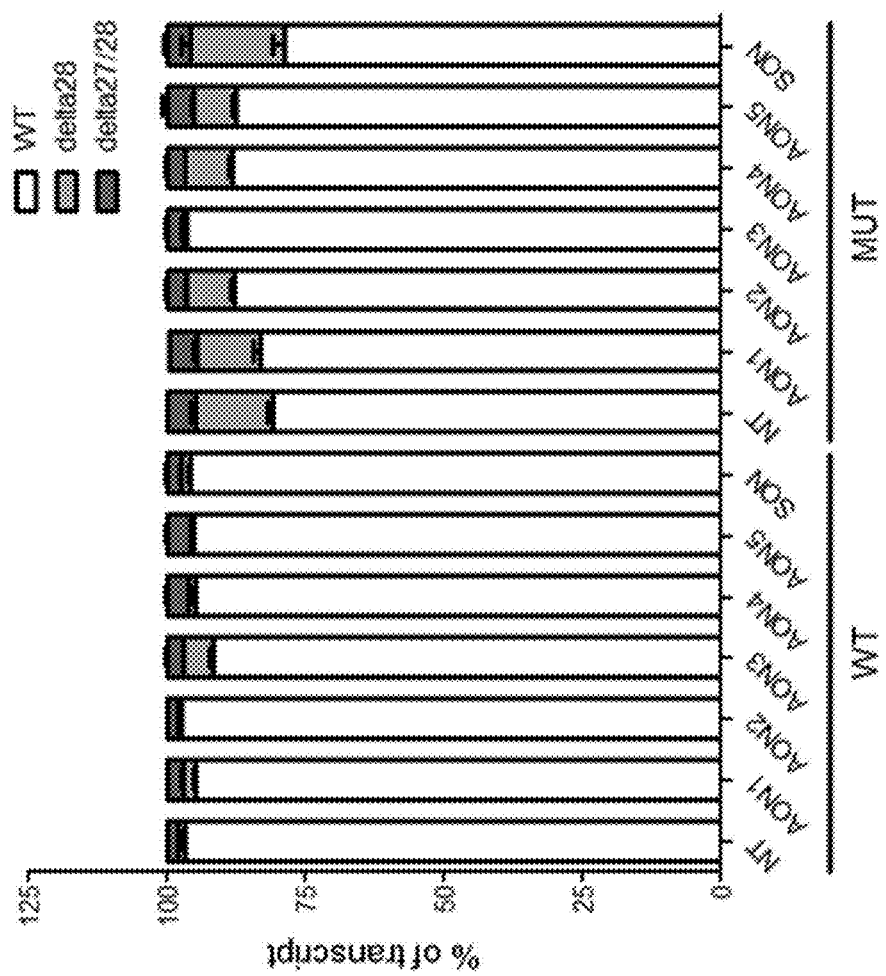
FIG. 3: Semi-quantification of the transcripts identified by RT-PCR. All ABCA4 transcripts detected in the gel were semi-quantified using FIJI software.

Following RT-PCR analysis of all replicates, the ratio of the bands was semi-quantified using Fiji software. Briefly, the intensity and area of all the bands in each lane were measured. Each of these bands represents a different transcript, and all transcripts together represent the 100% ABCA4 transcripts present in the sample. Subsequently, the measurement of each band was used to calculate the percentage of each transcript. Percentages are represented in FIG. 3.

Example 3

Generation of Photoreceptor Precursor Cells

Skin biopsies of a patient carrying the c.4253+43G>A in a heterozygous manner in a heterozygous were obtained and fibroblast cell lines were generated. Subsequently, induced pluripotent stem cells (iPSCs) were reprogrammed and differentiated to photoreceptor precursor cells (PPCs), as described previously (Sangermano et al., 2016). Differentiated cells were subjected to RT-PCR analysis.

RT-PCR Analysis Using Control and Patient-Derived PPCs

Total RNA was isolated from iPSC-derived PPCs using the NucleoSpin RNA Clean-up Kit (catalog no., 740955-50; Macherey-Nagel, Duren, Germany) according to the manufacturers protocol. One microgram was employed for cDNA synthesis using the SuperScript™ VILO™ Master Mix (catalog no., 11755050; ThermoFisher Scientific, Waltham, Mass., USA) following the manufacturer's instructions. In the RT-PCR, ABCA4 was amplified from exon 26 to 31 using the primers represented by SEQ ID NOs: 24 and 30.

Figure 4:
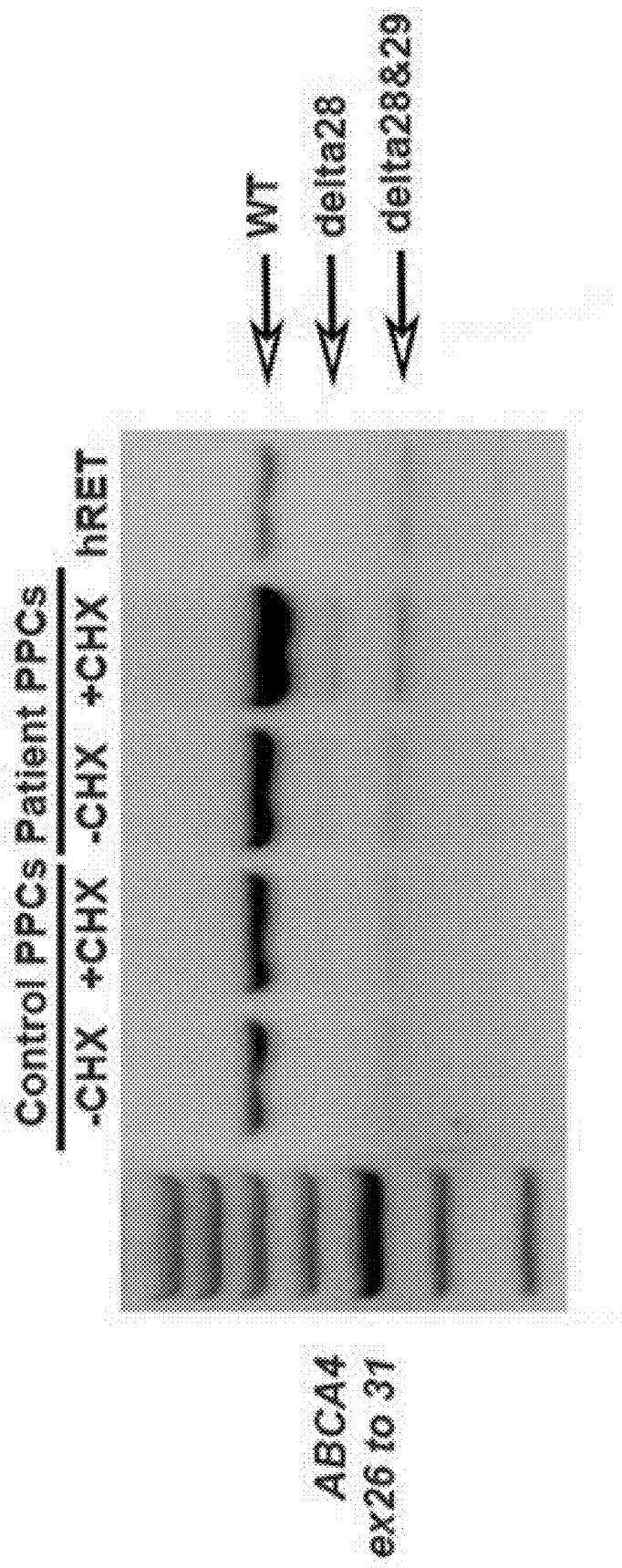
FIG. 4: RT-PCR analysis using control and patient-derived photoreceptor progenitor cells (PPCs).

RT-PCR using patient-derived differentiated cells to PPCs in the presence (+CHX) or absence (−CHX) of cycloheximide (an inhibitor of the nonsense-mediated decay, NMD), showed an increase on skipping of exon 28 (delta28). In addition, skipping of exon 28 and 29 was found in all samples, including human retina (hRET), suggesting that this is a naturally occurring event. The skipping of exon 28 was especially visible after CHX treatment, indicating that the transcript is subjected to NMD degradation (FIG. 4).

REFERENCES

Albert S, Garanto A, Sangermano R, Khan M, Bax N M, Hoyng C B, Zernant J, Lee W, Allikmets R, Collin R W J, Cremers F P M (2018) Identification and Rescue of Splice Defects Caused by Two Neighboring Deep-Intronic ABCA4 Mutations Underlying Stargardt Disease. *Am J Hum Genet*, 102(4):517-527.

Allikmets, R., Singh, N., Sun, H., Shroyer, N. F., Hutchinson, A., Chidambaram, A., Gerrard, B., Baird, L., Stauffer, D., Peiffer, A., Rattner, A., Smallwood, P., Li, Y., Anderson, K. L., Lewis, R. A., Nathans, J., Leppert, M., Dean, M. & Lupski, J. R. A photoreceptor cell-specific ATP-binding transporter gene (ABCR) is mutated in recessive Stargardt macular dystrophy. Nat. Genet. 15, 236-246 (1997), doi:10.1038/ng0397-236.

Bauwens, M., De Zaeytijd, J., Weisschuh, N., Kohl, S., Meire, F., Dahan, K., Depasse, F., De Jaegere, S., De Ravel, T., De Rademaeker, M., Loeys, B., Coppieters, F., Leroy, B. P. & De Baere, E. An augmented ABCA4 screen targeting noncoding regions reveals a deep intronic founder variant in Belgian Stargardt patients. *Hum. Mutat.* 36, 39-42 (2015), doi:10.1002/humu.22716.

Bax, N. M., Sangermano, R., Roosing, S., Thiadens, A. A., Hoefsloot, L. H., van den Born, L. I., Phan, M., Klevering, B. J., Westeneng-van Haaften, C., Braun, T. A., Zonneveld-Vrieling, M. N., de Wijs, I., Mutlu, M., Stone, E. M., den Hollander, A. I., Klaver, C. C., Hoyng, C. B. & Cremers, F. P. M. Heterozygous deep-intronic variants and deletions in ABCA4 in persons with retinal dystrophies and one exonic ABCA4 variant. *Hum. Mutat.* 36, 43-47 (2015), doi:10.1002/humu.22717.

Braun, T. A., Mullins, R. F., Wagner, A. H., Andorf, J. L., Johnston, R. M., Bakall, B. B., Deluca, A. P., Fishman, G. A., Lam, B. L., Weleber, R. G., Cideciyan, A. V., Jacobson, S. G., Sheffield, V. C., Tucker, B. A. & Stone, E. M. Non-exomic and synonymous variants in ABCA4 are an important cause of Stargardt disease. Hum. Mol. Genet. 22, 5136-5145 (2013), doi:10.1093/hmg/ddt367.

Collin R W J, den Hollander A I, van der Velde-Visser S, Bennicelli J, Bennett J, Cremers F P M (2012). Antisense oligonucleotide (AON)-based therapy for Leber Congenital Amaurosis caused by a frequent mutation in CEP290. Mol Ther Nucl Acids, e14.

Cremers, F. P. M., van de Pol, D. J., van Driel, M., den Hollander, A. I., van Haren, F. J., Knoers, N. V., Tijmes, N., Bergen, A. A., Rohrschneider, K., Blankenagel, A., Pinckers, A. J., Deutman, A. F. & Hoyng, C. B. Autosomal recessive retinitis pigmentosa and cone-rod dystrophy caused by splice site mutations in the Stargardt's disease gene ABCR. Hum. Mol. Gen. 7, 355-362 (1998).

Fujinami, K., Zernant, J., Chana, R. K., Wright, G. A., Tsunoda, K., Ozawa, Y., Tsubota, K., Webster, A. R., Moore, A. T., Allikmets, R. & Michaelides, M. ABCA4 gene screening by next-generation sequencing in a British cohort. Invest. Ophthalmol. Vis. Sci. 54, 6662-6674 (2013), doi:10.1167/iovs.13-12570.

Garanto A, Chung D C, Duijkers L, Corral-Serrano J C, Messchaert M, Xiao R, Bennett J, Vandenberghe L H, Collin R W J (2016). In vitro and in vivo rescue of aberrant splicing in CEP290-associated LCA by antisense oligonucleotide delivery. Hum Mol Genet, epub ahead of print.

Lee, W., Xie, Y., Zernant, J., Yuan, B., Bearelly, S., Tsang, S. H., Lupski, J. R. & Allikmets, R. Complex inheritance of ABCA4 disease: four mutations in a family with multiple macular phenotypes. Hum. Genet. 135, 9-19 (2016), doi:10.1007/s00439-015-1605-y.

Lewis, R. A., Shroyer, N. F., Singh, N., Allikmets, R., Hutchinson, A., Li, Y., Lupski, J. R., Leppert, M. & Dean, M. Genotype/Phenotype analysis of a photoreceptor-specific ATP-binding cassette transporter gene, ABCR, in Stargardt disease. Am. J. Hum. Genet. 64, 422-434 (1999), doi:10.1086/302251.

Maugeri, A., van Driel, M. A., van de Pol, D. J., Klevering, B. J., van Haren, F. J., Tijmes, N., Bergen, A. A., Rohrschneider, K., Blankenagel, A., Pinckers, A. J., Dahl, N., Brunner, H. G., Deutman, A. F., Hoyng, C. B. & Cremers, F. P. M. The 2588G-->C mutation in the ABCR gene is a mild frequent founder mutation in the Western European population and allows the classification of ABCR mutations in patients with Stargardt disease. Am. J. Hum. Genet. 64, 1024-1035 (1999).

Maugeri, A., Klevering, B. J., Rohrschneider, K., Blankenagel, A., Brunner, H. G., Deutman, A. F., Hoyng, C. B. & Cremers, F. P. M. Mutations in the ABCA4 (ABCR) gene are the major cause of autosomal recessive cone-rod dystrophy. Am. J. Hum. Genet. 67, 960-966 (2000), doi: 10.1086/303079.

Martinez-Mir, A., Paloma, E., Allikmets, R., Ayuso, C., del Rio, T., Dean, M., Vilageliu, L., Gonzalez-Duarte, R. & Balcells, S. Retinitis pigmentosa caused by a homozygous mutation in the Stargardt disease gene ABCR. Nat. Genet. 18, 11-12 (1998), doi:10.1038/ng0198-11.

Rivera, A., White, K., Stohr, H., Steiner, K., Hemmrich, N., Grimm, T., Jurklies, B., Lorenz, B., Scholl, H. P., Apfelstedt-Sylla, E. & Weber, B. H. A comprehensive survey of sequence variation in the ABCA4 (ABCR) gene in Stargardt disease and age-related macular degeneration. Am. J. Hum. Genet. 67, 800-813 (2000), doi:10.1086/303090.

Sangermano R, Bax N M, Bauwens M, van den Born L I, de Baere E, Garanto A, Collin R W J, Goercharn-Ramlal A S, den Engelsman-van Dijk A H, Rohrschneide K, Hoyng C B, Cremers F P M, Albert S (2016). Photoreceptor progenitor mRNA analysis reveals exon skipping resulting from the ABCA4 c.5461-10T>C mutation in Stargardt disease. Ophthalmology, 123: 1375-1385.

Sangermano R, Khan M, Cornelis S S, Richelle V, Albert S, Garanto A, Elmelik D, Qamar R, Lugtenberg D, van den Born L I, Collin R W J, Cremers F P M (2018) ABCA4 midigenes reveal the full splice spectrum of all reported noncanonical splice site variants in Stargardt disease. Genome Res, 28(1):100-110.

Schulz, H. L., Grassmann, F., Kellner, U., Spital, G., Ruther, K., Jagle, H., Hufendiek, K., Rating, P., Huchzermeyer, C., Baier, M. J., Weber, B. H. & Stohr, H. Mutation spectrum of the ABCA4 gene in 335 Stargardt disease patients from a multicenter German cohort-impact of selected deep intronic variants and common SNPs. Invest. Ophthalmol. Vis. Sci. 58, 394-403 (2017), doi:10.1167/iovs.16-19936.

van Driel, M. A., Maugeri, A., Klevering, B. J., Hoyng, C. B. & Cremers, F. P. M. ABCR unites what ophthalmologists divide(s). Ophthalmic Genet. 19, 117-122 (1998).

Webster, A. R., Heon, E., Lotery, A. J., Vandenburgh, K., Casavant, T. L., Oh, K. T., Beck, G., Fishman, G. A., Lam, B. L., Levin, A., Heckenlively, J. R., Jacobson, S. G., Weleber, R. G., Sheffield, V. C. & Stone, E. M. An analysis of allelic variation in the ABCA4 gene. Invest. Ophthal. Vis. Sci. 42, 1179-1189 (2001).

Zernant, J., Lee, W., Collison, F. T., Fishman, G. A., Sergeev, Y. V., Schuerch, K., Sparrow, J. R., Tsang, S. H. & Allikmets, R. Frequent hypomorphic alleles account for a significant fraction of ABCA4 disease and distinguish it from age-related macular degeneration. J. Med. Genet. 54, 404-412 (2017), doi:10.1136/jmedgenet-2017-104540.

Zernant, J., Schubert, C., Im, K. M., Burke, T., Brown, C. M., Fishman, G. A., Tsang, S. H., Gouras, P., Dean, M. & Allikmets, R. Analysis of the ABCA4 gene by next-generation sequencing. Invest. Ophthalmol. Vis. Sci. 52, 8479-8487 (2011), doi:10.1167/iovs.11-8182.

The invention claimed is:

1. An ABCA4 exon 28 retention molecule that binds to and/or is complementary to a polynucleotide with SEQ ID NO:5, wherein the ABCA4 exon 28 retention molecule comprises a 2'-O alkyl phosphorothioate antisense oligonucleotide.

2. The ABCA4 exon 28 retention molecule according to claim 1, wherein the molecule is a nucleic acid molecule.

3. The ABCA4 exon 28 retention molecule according to claim 2, wherein the nucleic acid molecule comprises or consists of an antisense oligonucleotide that is complementary to the polynucleotide, wherein the antisense oligonucleotide has a length of 8 to 100 nucleotides.

4. The ABCA4 exon 28 retention molecule according to claim 3, wherein the antisense oligonucleotide has a length of 10 to 40 nucleotides.

5. The ABCA4 exon 28 retention molecule according to claim 3, wherein the antisense oligonucleotide has a length 12 to 30 nucleotides.

6. The ABCA4 exon 28 retention molecule according to claim 3, wherein the antisense oligonucleotide has a length of 20 to 24 nucleotides.

7. The ABCA4 exon 28 retention molecule according to claim 3, wherein the antisense oligonucleotide comprises or consists of a sequence selected from the group consisting of SEQ ID NO: 17, SEQ ID NO: 18, SEQ ID NO: 19, SEQ ID NO: 20, and SEQ ID NO: 21.

8. The ABCA4 exon 28 retention molecule according to claim 4 wherein the antisense oligonucleotide comprises or consist of SEQ ID NO:19.

9. A set of ABCA4 exon 28 retention molecules comprising at least two ABCA4 exon 28 retention molecules as defined in claim 1.

10. The set of ABCA4 exon 28 retention molecules according to claim 9, wherein the set comprises or consists of at least two antisense oligonucleotides selected from the group consisting of SEQ ID NO: 17, SEQ ID NO: 18, SEQ ID NO: 19, SEQ ID NO: 20, and SEQ ID NO: 21.

11. A viral vector expressing an ABCA4 exon 28 retention molecule that binds to and/or is complementary to a polynucleotide with SEQ ID NO:5 when placed under conditions conducive to expression of the molecule.

12. A pharmaceutical composition comprising an ABCA4 exon 28 retention molecule according to claim 1 and a pharmaceutically acceptable excipient.

13. A method for modulating splicing of ABCA4 in a cell, said method comprising contacting said cell with an ABCA4 exon 28 retention molecule as defined claim 1.

14. The method according to claim 13, wherein the method is for treating an ABCA4-related disease or condition.

15. The ABCA4 exon 28 retention molecule according to claim 1, wherein the ABCA4 exon 28 retention molecule is complementary to a polynucleotide with SEQ ID NO:6.

16. The ABCA4 exon 28 retention molecule according to claim 1, wherein the 2'-O alkyl phosphorothioate antisense oligonucleotide is selected from the group consisting of a 2'-O-methyl modified ribose (RNA), 2'-O-ethyl modified ribose, 2'-O-propyl modified ribose, and substituted derivatives of these modifications.

17. The method according to claim 13, wherein the ABCA4-related disease or condition is Stargardt disease.

18. The method according to claim 13, wherein the pharmaceutical composition is administered by intravitreal administration in an amount ranged from 0.05 mg and 5 mg of total exon 28 retention molecule per eye.

19. The method according to claim 13, wherein the pharmaceutical composition is for intravitreal administration and is dosed in an amount ranged from 0.1 and 1 mg of total antisense oligonucleotides for redirecting splicing per eye.

* * * * *